(12) United States Patent
Ono et al.

(10) Patent No.: US 6,451,617 B1
(45) Date of Patent: Sep. 17, 2002

(54) METHOD OF SCREENING TGF-β INHIBITORY SUBSTANCES

(75) Inventors: Koichiro Ono; Toshihiko Ohtomo; Masayuki Tsuchiya, all of Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/529,279

(22) PCT Filed: Oct. 22, 1998

(86) PCT No.: PCT/JP98/04796

§ 371 (c)(1),
(2), (4) Date: Apr. 11, 2000

(87) PCT Pub. No.: WO99/21010

PCT Pub. Date: Apr. 29, 1999

(30) Foreign Application Priority Data

Oct. 22, 1997 (JP) .............................................. 9-290188

(51) Int. Cl.[7] ..................... G01N 33/566; G01N 33/53; C12P 21/06; A61K 38/00; C07K 1/00
(52) U.S. Cl. ....................... 436/501; 435/7.1; 435/69.1; 530/300; 530/350
(58) Field of Search ...................... 435/7.1, 7.2, 7.21, 435/7.6, 69.1, 69.2, 69.7, 71.1, 25.3, 320.1; 436/501; 530/300; 530/350

(56) References Cited

FOREIGN PATENT DOCUMENTS

| JP | 6-507245 | 8/1994 |
|---|---|---|
| JP | 7-505294 | 6/1995 |

OTHER PUBLICATIONS

Shibuya et al., Science 272, 1179–1182, May 1996.*

Maniatis et al., Molecular Cloning: a laboratory Manual (1982), pp. 458 and 459. Published by Cold Spring Harbor Laboratory, Box 100, Cold Spring Harbor, New York.*

Root et al., Calmodulin–sensitive interaction of human nebulin fragments with actin and myosin. Biochemistry 33, 12581–12591, 1994.*

Science, vol. 270, pp. 2008–2011, (Dec. 22, 1995).

Science, vol. 272, pp. 1179–1181, (May 24, 1996).

D. M. Kingsley; Genes and Development 8; pp. 133–146, (1994).

J. L. Wrana, et al.; Nature, vol. 370; pp. 341–347 (1994).

K. Yamaguchi et al.; Science, vol. 270, pp. 2008–2011 (1995).

H. Shibuya et al.; Science, vol. 272; pp. 1179–1182 (1996).

* cited by examiner

Primary Examiner—Ethan C. Whisenant
Assistant Examiner—Frank W Lu
(74) Attorney, Agent, or Firm—Foley & Lardner

(57) ABSTRACT

A method for screening substances that inhibit binding between a TAK1 polypeptide and a TAB1 polypeptide, which comprises contacting the TAB1 polypeptide to the TAK1 polypeptide and a test sample and then detecting or determining the TAK1 polypeptide that is bound to the TAB1 polypeptide.

50 Claims, 12 Drawing Sheets

A

B

Fig. 1
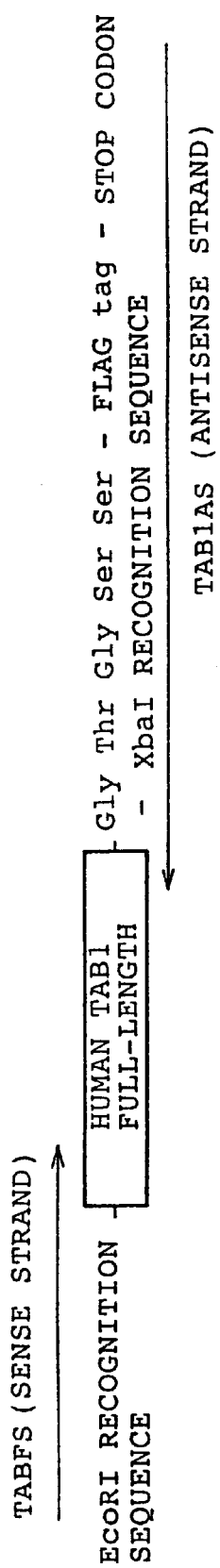
A
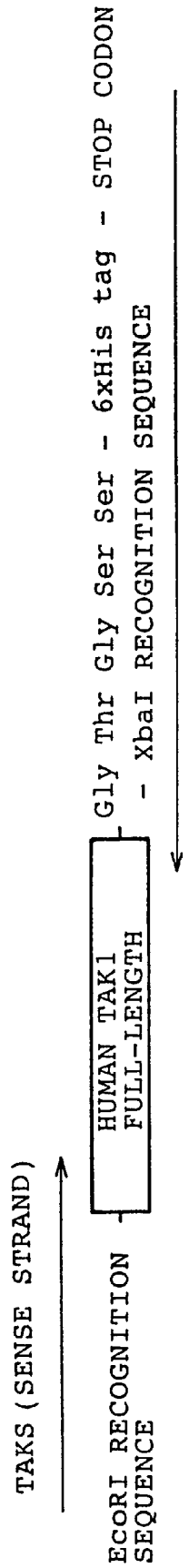
B 1. pM/pVP16
2. pM-TAK1/pVP16
3. pM-TAK1/pVP16-C68
4. pM-TAK1DN/pVP16
5. pM-TAK1DN/pVP16-C68

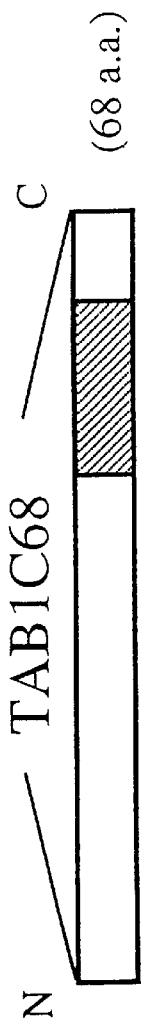
Fig. 11

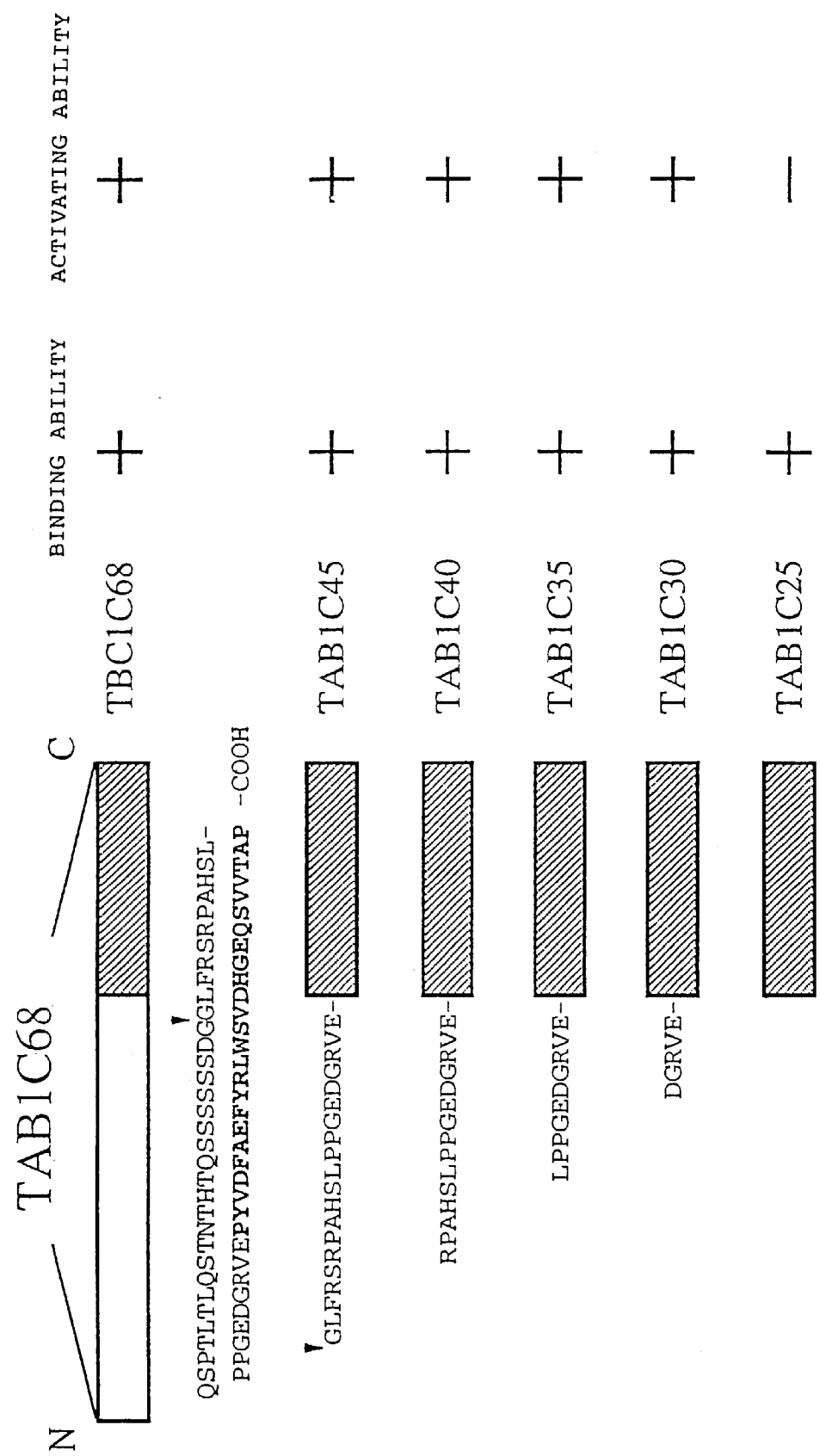

SEQUENCE LISTING

<160> NUMBER OF SEQ ID NOS: 48

<210> SEQ ID NO 1
<211> LENGTH: 1560
<212> TYPE: DNA
<213> ORGANISM: Homo sapiens
<220> FEATURE:
<221> NAME/KEY: CDS
<222> LOCATION: (30)..(1541)

<400> SEQUENCE: 1

| | | | | | | | | | | | | | | | | |
|---|---|---|---|---|---|---|---|---|---|---|---|---|---|---|---|---|
| gaattcgtgg | cccgcagggt | tcctccaag | atg | gcg | gcg | cag | agg | agg | agc | ttg | | | | | | 53 |
| | | | Met | Ala | Ala | Gln | Arg | Arg | Ser | Leu | | | | | | |
| | | | 1 | | | | 5 | | | | | | | | | |

```
ctg cag agt gag cag cag cca agc tgg aca gat gac ctg cct ctc tgc      101
Leu Gln Ser Glu Gln Gln Pro Ser Trp Thr Asp Asp Leu Pro Leu Cys
         10                  15                  20 cac ctc tct ggg gtt ggc tca gcc tcc aac cgc agc tac tct gct gat      149
His Leu Ser Gly Val Gly Ser Ala Ser Asn Arg Ser Tyr Ser Ala Asp
 25                  30                  35                  40 ggc aag ggc act gag agc cac ccg cca gag gac agc tgg ctc aag ttc      197
Gly Lys Gly Thr Glu Ser His Pro Pro Glu Asp Ser Trp Leu Lys Phe
             45                  50                  55 agg agt gag aac aac tgc ttc ctg tat ggg gtc ttc aac ggc tat gat      245
Arg Ser Glu Asn Asn Cys Phe Leu Tyr Gly Val Phe Asn Gly Tyr Asp
         60                  65                  70 ggc aac cga gtg acc aac ttc gtg gcc cag cgg ctg tcc gca gag ctc      293
Gly Asn Arg Val Thr Asn Phe Val Ala Gln Arg Leu Ser Ala Glu Leu
     75                  80                  85 ctg ctg ggc cag ctg aat gcc gag cac gcc gag gcc gat gtg cgg cgt      341
Leu Leu Gly Gln Leu Asn Ala Glu His Ala Glu Ala Asp Val Arg Arg
 90                  95                 100 gtg ctg ctg cag gcc ttc gat gtg gtg gag agg agc ttc ctg gag tcc      389
Val Leu Leu Gln Ala Phe Asp Val Val Glu Arg Ser Phe Leu Glu Ser
105                 110                 115                 120 att gac gac gcc ttg gct gag aag gca agc ctc cag tcg caa ttg cca      437
Ile Asp Asp Ala Leu Ala Glu Lys Ala Ser Leu Gln Ser Gln Leu Pro
             125                 130                 135 gag gga gtc cct cag cac cag ctg cct cct cag tat cag aag atc ctt      485
Glu Gly Val Pro Gln His Gln Leu Pro Pro Gln Tyr Gln Lys Ile Leu
         140                 145                 150 gag aga ctc aag acg tta gag agg gaa att tcg gga ggg gcc atg gcc      533
Glu Arg Leu Lys Thr Leu Glu Arg Glu Ile Ser Gly Gly Ala Met Ala
     155                 160                 165 gtt gtg gcg gtc ctt ctc aac aac aag ctc tac gtc gcc aat gtc ggt      581
Val Val Ala Val Leu Leu Asn Asn Lys Leu Tyr Val Ala Asn Val Gly
170                 175                 180 aca aac cgt gca ctt tta tgc aaa tcg aca gtg gat ggg ttg cag gtg      629
Thr Asn Arg Ala Leu Leu Cys Lys Ser Thr Val Asp Gly Leu Gln Val
            185                 190                 195                 200 aca cag ctg aac gtg gac cac acc aca gag aac gag gat gag ctc ttc      677
Thr Gln Leu Asn Val Asp His Thr Thr Glu Asn Glu Asp Glu Leu Phe
        205                 210                 215 cgt ctt tcg cag ctg ggc ttg gat gct gga aag atc aag cag gtg ggg      725
Arg Leu Ser Gln Leu Gly Leu Asp Ala Gly Lys Ile Lys Gln Val Gly
    220                 225                 230 atc atc tgt ggg cag gag agc acc cgg cgg atc ggg gat tac aag gtt      773
Ile Ile Cys Gly Gln Glu Ser Thr Arg Arg Ile Gly Asp Tyr Lys Val
235                 240                 245
```

| | | |
|---|---|---|
| aaa tat ggc tac acg gac att gac ctt ctc agc gct gcc aag tcc aaa<br>Lys Tyr Gly Tyr Thr Asp Ile Asp Leu Leu Ser Ala Ala Lys Ser Lys<br>250 255 260 | | 821 |
| cca atc atc gca gag cca gaa atc cat ggg gca cag ccg ctg gat ggg<br>Pro Ile Ile Ala Glu Pro Glu Ile His Gly Ala Gln Pro Leu Asp Gly<br>265 270 275 280 | | 869 |
| gtg acg ggc ttc ttg gtg ctg atg tcg gag ggg ttg tac aag gcc cta<br>Val Thr Gly Phe Leu Val Leu Met Ser Glu Gly Leu Tyr Lys Ala Leu<br>285 290 295 | | 917 |
| gag gca gcc cat ggg cct ggg cag gcc aac cag gag att gct gcg atg<br>Glu Ala Ala His Gly Pro Gly Gln Ala Asn Gln Glu Ile Ala Ala Met<br>300 305 310 | | 965 |
| att gac act gag ttt gcc aag cag acc tcc ctg gac gca gtg gcc cag<br>Ile Asp Thr Glu Phe Ala Lys Gln Thr Ser Leu Asp Ala Val Ala Gln<br>315 320 325 | | 1013 |
| gcc gtc gtg gac cgg gtg aag cgc atc cac agc gac acc ttc gcc agt<br>Ala Val Val Asp Arg Val Lys Arg Ile His Ser Asp Thr Phe Ala Ser<br>330 335 340 | | 1061 |
| ggt ggg gag cgt gcc agg ttc tgc ccc cgg cac gag gac atg acc ctg<br>Gly Gly Glu Arg Ala Arg Phe Cys Pro Arg His Glu Asp Met Thr Leu<br>345 350 355 360 | | 1109 |
| cta gtg agg aac ttt ggc tac ccg ctg ggc gaa atg agc cag ccc aca<br>Leu Val Arg Asn Phe Gly Tyr Pro Leu Gly Glu Met Ser Gln Pro Thr<br>365 370 375 | | 1157 |
| ccg agc cca gcc cca gct gca gga gga cga gtg tac cct gtg tct gtg<br>Pro Ser Pro Ala Pro Ala Ala Gly Gly Arg Val Tyr Pro Val Ser Val<br>380 385 390 | | 1205 |
| cca tac tcc agc gcc cag agc acc agc aag acc agc gtg acc ctc tcc<br>Pro Tyr Ser Ser Ala Gln Ser Thr Ser Lys Thr Ser Val Thr Leu Ser<br>395 400 405 | | 1253 |
| ctt gtc atg ccc tcc cag ggc cag atg gtc aac ggg gct cac agt gct<br>Leu Val Met Pro Ser Gln Gly Gln Met Val Asn Gly Ala His Ser Ala<br>410 415 420 | | 1301 |
| tcc acc ctg gac gaa gcc acc ccc acc ctc acc aac caa agc ccg acc<br>Ser Thr Leu Asp Glu Ala Thr Pro Thr Leu Thr Asn Gln Ser Pro Thr<br>425 430 435 440 | | 1349 |
| tta acc ctg cag tcc acc aac acg cac acg cag agc agc agc tcc agc<br>Leu Thr Leu Gln Ser Thr Asn Thr His Thr Gln Ser Ser Ser Ser Ser<br>445 450 455 | | 1397 |
| tct gac gga ggc ctc ttc cgc tcc cgg ccc gcc cac tcg ctc ccg cct<br>Ser Asp Gly Gly Leu Phe Arg Ser Arg Pro Ala His Ser Leu Pro Pro<br>460 465 470 | | 1445 |
| ggc gag gac ggt cgt gtt gag ccc tat gtg gac ttt gct gag ttt tac<br>Gly Glu Asp Gly Arg Val Glu Pro Tyr Val Asp Phe Ala Glu Phe Tyr<br>475 480 485 | | 1493 |
| cgc ctc tgg agc gtg gac cat ggc gag cag agc gtg gtg aca gca ccg<br>Arg Leu Trp Ser Val Asp His Gly Glu Gln Ser Val Val Thr Ala Pro<br>490 495 500 | | 1541 |
| tagggcagcc ggaggaatg | | 1560 |

<210> SEQ ID NO 2
<211> LENGTH: 504
<212> TYPE: PRT
<213> ORGANISM: Homo sapiens

<400> SEQUENCE: 2

Met Ala Ala Gln Arg Arg Ser Leu Leu Gln Ser Glu Gln Gln Pro Ser
1               5                   10                  15

Trp Thr Asp Asp Leu Pro Leu Cys His Leu Ser Gly Val Gly Ser Ala
            20                  25                  30

```
Ser Asn Arg Ser Tyr Ser Ala Asp Gly Lys Gly Thr Glu Ser His Pro
         35                  40                  45

Pro Glu Asp Ser Trp Leu Lys Phe Arg Ser Glu Asn Asn Cys Phe Leu
     50                  55                  60

Tyr Gly Val Phe Asn Gly Tyr Asp Gly Asn Arg Val Thr Asn Phe Val
 65              70                  75                      80

Ala Gln Arg Leu Ser Ala Glu Leu Leu Gly Gln Leu Asn Ala Glu
                 85                  90                  95

His Ala Glu Ala Asp Val Arg Arg Val Leu Leu Gln Ala Phe Asp Val
             100                 105                 110

Val Glu Arg Ser Phe Leu Glu Ser Ile Asp Asp Ala Leu Ala Glu Lys
         115                 120                 125

Ala Ser Leu Gln Ser Gln Leu Pro Glu Gly Val Pro Gln His Gln Leu
     130                 135                 140

Pro Pro Gln Tyr Gln Lys Ile Leu Glu Arg Leu Lys Thr Leu Glu Arg
145                 150                 155                 160

Glu Ile Ser Gly Gly Ala Met Ala Val Ala Val Leu Leu Asn Asn
                 165                 170                 175

Lys Leu Tyr Val Ala Asn Val Gly Thr Asn Arg Ala Leu Leu Cys Lys
             180                 185                 190

Ser Thr Val Asp Gly Leu Gln Val Thr Gln Leu Asn Val Asp His Thr
         195                 200                 205

Thr Glu Asn Glu Asp Glu Leu Phe Arg Leu Ser Gln Leu Gly Leu Asp
     210                 215                 220

Ala Gly Lys Ile Lys Gln Val Gly Ile Ile Cys Gly Gln Glu Ser Thr
225                 230                 235                 240

Arg Arg Ile Gly Asp Tyr Lys Val Lys Tyr Gly Tyr Thr Asp Ile Asp
                 245                 250                 255

Leu Leu Ser Ala Ala Lys Ser Lys Pro Ile Ile Ala Glu Pro Glu Ile
             260                 265                 270

His Gly Ala Gln Pro Leu Asp Gly Val Thr Gly Phe Leu Val Leu Met
         275                 280                 285

Ser Glu Gly Leu Tyr Lys Ala Leu Glu Ala Ala His Gly Pro Gly Gln
     290                 295                 300

Ala Asn Gln Glu Ile Ala Ala Met Ile Asp Thr Glu Phe Ala Lys Gln
305                 310                 315                 320

Thr Ser Leu Asp Ala Val Ala Gln Ala Val Asp Arg Val Lys Arg
                 325                 330                 335

Ile His Ser Asp Thr Phe Ala Ser Gly Gly Glu Arg Ala Arg Phe Cys
             340                 345                 350

Pro Arg His Glu Asp Met Thr Leu Leu Val Arg Asn Phe Gly Tyr Pro
         355                 360                 365

Leu Gly Glu Met Ser Gln Pro Thr Pro Ser Pro Ala Pro Ala Ala Gly
     370                 375                 380

Gly Arg Val Tyr Pro Val Ser Val Pro Tyr Ser Ser Ala Gln Ser Thr
385                 390                 395                 400

Ser Lys Thr Ser Val Thr Leu Ser Leu Val Met Pro Ser Gln Gly Gln
                 405                 410                 415

Met Val Asn Gly Ala His Ser Ala Ser Thr Leu Asp Glu Ala Thr Pro
             420                 425                 430

Thr Leu Thr Asn Gln Ser Pro Thr Leu Thr Leu Gln Ser Thr Asn Thr
         435                 440                 445
```

```
His Thr Gln Ser Ser Ser Ser Ser Asp Gly Gly Leu Phe Arg Ser
        450                 455                 460

Arg Pro Ala His Ser Leu Pro Pro Gly Glu Asp Gly Arg Val Glu Pro
465                 470                 475                 480

Tyr Val Asp Phe Ala Glu Phe Tyr Arg Leu Trp Ser Val Asp His Gly
                485                 490                 495

Glu Gln Ser Val Val Thr Ala Pro
            500

<210> SEQ ID NO 3
<211> LENGTH: 2656
<212> TYPE: DNA
<213> ORGANISM: Homo sapiens
<220> FEATURE:
<221> NAME/KEY: CDS
<222> LOCATION: (183)..(1919)

<400> SEQUENCE: 3
gtcgagatcc attgtgctct aaagacggct gtggccgctg cctctacccc cgccacggat      60
cgccgggtag taggactgcg cggctccagg ctgagggtcg gtccggaggc gggtgggcgc     120
gggtctcacc cggattgtcc gggtggcacc gttcccggcc ccaccgggcg ccgcgaggga     180 tc atg tct aca gcc tct gcc gcc tcc tcc tcc tcc tcg tct tcg gcc        227
   Met Ser Thr Ala Ser Ala Ala Ser Ser Ser Ser Ser Ser Ala
   1               5                   10                  15 ggt gag atg atc gaa gcc cct tcc cag gtc ctc aac ttt gaa gag atc        275
Gly Glu Met Ile Glu Ala Pro Ser Gln Val Leu Asn Phe Glu Glu Ile
            20                  25                  30 gac tac aag gag atc gag gtg gaa gag gtt gtt gga aga gga gcc ttt        323
Asp Tyr Lys Glu Ile Glu Val Glu Glu Val Val Gly Arg Gly Ala Phe
        35                  40                  45 gga gtt gtt tgc aaa gct aag tgg aga gca aaa gat gtt gct att aaa        371
Gly Val Val Cys Lys Ala Lys Trp Arg Ala Lys Asp Val Ala Ile Lys
    50                  55                  60 caa ata gaa agt gaa tct gag agg aaa gcg ttt att gta gag ctt cgg        419
Gln Ile Glu Ser Glu Ser Glu Arg Lys Ala Phe Ile Val Glu Leu Arg
65                  70                  75 cag tta tcc cgt gtg aac cat cct aat att gta aag ctt tat gga gcc        467
Gln Leu Ser Arg Val Asn His Pro Asn Ile Val Lys Leu Tyr Gly Ala
80                  85                  90                  95 tgc ttg aat cca gtg tgt ctt gtg atg gaa tat gct gaa ggg ggc tct        515
Cys Leu Asn Pro Val Cys Leu Val Met Glu Tyr Ala Glu Gly Gly Ser
                100                 105                 110 tta tat aat gtg ctg cat ggt gct gaa cca ttg cca tat tat act gct        563
Leu Tyr Asn Val Leu His Gly Ala Glu Pro Leu Pro Tyr Tyr Thr Ala
            115                 120                 125 gcc cac gca atg agt tgg tgt tta cag tgt tcc caa gga gtg gct tat        611
Ala His Ala Met Ser Trp Cys Leu Gln Cys Ser Gln Gly Val Ala Tyr
        130                 135                 140 ctt cac agc atg caa ccc aaa gcg cta att cac agg gac ctg aaa cca        659
Leu His Ser Met Gln Pro Lys Ala Leu Ile His Arg Asp Leu Lys Pro
    145                 150                 155 cca aac tta ctg ctg gtt gca ggg ggg aca gtt cta aaa att tgt gat        707
Pro Asn Leu Leu Leu Val Ala Gly Gly Thr Val Leu Lys Ile Cys Asp
160                 165                 170                 175 ttt ggt aca gcc tgt gac att cag aca cac atg acc aat aac aag ggg        755
Phe Gly Thr Ala Cys Asp Ile Gln Thr His Met Thr Asn Asn Lys Gly
                180                 185                 190 agt gct gct tgg atg gca cct gaa gtt ttt gaa ggt agt aat tac agt        803
Ser Ala Ala Trp Met Ala Pro Glu Val Phe Glu Gly Ser Asn Tyr Ser
```

-continued

| | | | | | | | | | | | | | | | | |
|---|---|---|---|---|---|---|---|---|---|---|---|---|---|---|---|---|
| | | | | 195 | | | | 200 | | | | 205 | | | | |
| gaa | aaa | tgt | gac | gtc | ttc | agc | tgg | ggt | att | att | ctt | tgg | gaa | gtg | ata | 851 |
| Glu | Lys | Cys | Asp | Val | Phe | Ser | Trp | Gly | Ile | Ile | Leu | Trp | Glu | Val | Ile | |
| | | 210 | | | | 215 | | | | 220 | | | | | | |
| acg | cgt | cgg | aaa | ccc | ttt | gat | gag | att | ggt | ggc | cca | gct | ttc | cga | atc | 899 |
| Thr | Arg | Arg | Lys | Pro | Phe | Asp | Glu | Ile | Gly | Gly | Pro | Ala | Phe | Arg | Ile | |
| | 225 | | | | 230 | | | | 235 | | | | | | | |
| atg | tgg | gct | gtt | cat | aat | ggt | act | cga | cca | cca | ctg | ata | aaa | aat | tta | 947 |
| Met | Trp | Ala | Val | His | Asn | Gly | Thr | Arg | Pro | Pro | Leu | Ile | Lys | Asn | Leu | |
| 240 | | | | | 245 | | | | 250 | | | | | 255 | | |
| cct | aag | ccc | att | gag | agc | ctg | atg | act | cgt | tgt | tgg | tct | aaa | gat | cct | 995 |
| Pro | Lys | Pro | Ile | Glu | Ser | Leu | Met | Thr | Arg | Cys | Trp | Ser | Lys | Asp | Pro | |
| | | | 260 | | | | 265 | | | | 270 | | | | | |
| tcc | cag | cgc | cct | tca | atg | gag | gaa | att | gtg | aaa | ata | atg | act | cac | ttg | 1043 |
| Ser | Gln | Arg | Pro | Ser | Met | Glu | Glu | Ile | Val | Lys | Ile | Met | Thr | His | Leu | |
| | | 275 | | | | 280 | | | | 285 | | | | | | |
| atg | cgg | tac | ttt | cca | gga | gca | gat | gag | cca | tta | cag | tat | cct | tgt | cag | 1091 |
| Met | Arg | Tyr | Phe | Pro | Gly | Ala | Asp | Glu | Pro | Leu | Gln | Tyr | Pro | Cys | Gln | |
| | 290 | | | | 295 | | | | 300 | | | | | | | |
| tat | tca | gat | gaa | gga | cag | agc | aac | tct | gcc | acc | agt | aca | ggc | tca | ttc | 1139 |
| Tyr | Ser | Asp | Glu | Gly | Gln | Ser | Asn | Ser | Ala | Thr | Ser | Thr | Gly | Ser | Phe | |
| 305 | | | | | 310 | | | | 315 | | | | | | | |
| atg | gac | att | gct | tct | aca | aat | acg | agt | aac | aaa | agt | gac | act | aat | atg | 1187 |
| Met | Asp | Ile | Ala | Ser | Thr | Asn | Thr | Ser | Asn | Lys | Ser | Asp | Thr | Asn | Met | |
| 320 | | | | 325 | | | | | 330 | | | | | 335 | | |
| gag | caa | gtt | cct | gcc | aca | aat | gat | act | att | aag | cgc | tta | gaa | tca | aaa | 1235 |
| Glu | Gln | Val | Pro | Ala | Thr | Asn | Asp | Thr | Ile | Lys | Arg | Leu | Glu | Ser | Lys | |
| | | | 340 | | | | 345 | | | | 350 | | | | | |
| ttg | ttg | aaa | aat | cag | gca | aag | caa | cag | agt | gaa | tct | gga | cgt | tta | agc | 1283 |
| Leu | Leu | Lys | Asn | Gln | Ala | Lys | Gln | Gln | Ser | Glu | Ser | Gly | Arg | Leu | Ser | |
| | | 355 | | | | 360 | | | | 365 | | | | | | |
| ttg | gga | gcc | tcc | cat | ggg | agc | agt | gtg | gag | agc | ttg | ccc | cca | acc | tct | 1331 |
| Leu | Gly | Ala | Ser | His | Gly | Ser | Ser | Val | Glu | Ser | Leu | Pro | Pro | Thr | Ser | |
| | 370 | | | | 375 | | | | 380 | | | | | | | |
| gag | ggc | aag | agg | atg | agt | gct | gac | atg | tct | gaa | ata | gaa | gct | agg | atc | 1379 |
| Glu | Gly | Lys | Arg | Met | Ser | Ala | Asp | Met | Ser | Glu | Ile | Glu | Ala | Arg | Ile | |
| 385 | | | | | 390 | | | | 395 | | | | | | | |
| gcc | gca | acc | aca | ggc | aac | gga | cag | cca | aga | cgt | aga | tcc | atc | caa | gac | 1427 |
| Ala | Ala | Thr | Thr | Gly | Asn | Gly | Gln | Pro | Arg | Arg | Arg | Ser | Ile | Gln | Asp | |
| 400 | | | | 405 | | | | | 410 | | | | | 415 | | |
| ttg | act | gta | act | gga | aca | gaa | cct | ggt | cag | gtg | agc | agt | agg | tca | tcc | 1475 |
| Leu | Thr | Val | Thr | Gly | Thr | Glu | Pro | Gly | Gln | Val | Ser | Ser | Arg | Ser | Ser | |
| | | | 420 | | | | 425 | | | | 430 | | | | | |
| agt | ccc | agt | gtc | aga | atg | att | act | acc | tca | gga | cca | acc | tca | gaa | aag | 1523 |
| Ser | Pro | Ser | Val | Arg | Met | Ile | Thr | Thr | Ser | Gly | Pro | Thr | Ser | Glu | Lys | |
| | | 435 | | | | 440 | | | | 445 | | | | | | |
| cca | act | cga | agt | cat | cca | tgg | acc | cct | gat | gat | tcc | aca | gat | acc | aat | 1571 |
| Pro | Thr | Arg | Ser | His | Pro | Trp | Thr | Pro | Asp | Asp | Ser | Thr | Asp | Thr | Asn | |
| | 450 | | | | 455 | | | | 460 | | | | | | | |
| gga | tca | gat | aac | tcc | atc | cca | atg | gct | tat | ctt | aca | ctg | gat | cac | caa | 1619 |
| Gly | Ser | Asp | Asn | Ser | Ile | Pro | Met | Ala | Tyr | Leu | Thr | Leu | Asp | His | Gln | |
| 465 | | | | | 470 | | | | 475 | | | | | | | |
| cta | cag | cct | cta | gca | ccg | tgc | cca | aac | tcc | aaa | gaa | tct | atg | gca | gtg | 1667 |
| Leu | Gln | Pro | Leu | Ala | Pro | Cys | Pro | Asn | Ser | Lys | Glu | Ser | Met | Ala | Val | |
| 480 | | | | 485 | | | | | 490 | | | | | 495 | | |
| ttt | gaa | cag | cat | tgt | aaa | atg | gca | caa | gaa | tat | atg | aaa | gtt | caa | aca | 1715 |
| Phe | Glu | Gln | His | Cys | Lys | Met | Ala | Gln | Glu | Tyr | Met | Lys | Val | Gln | Thr | |
| | | | | 500 | | | | 505 | | | | 510 | | | | |
| gaa | att | gca | ttg | tta | tta | cag | aga | aag | caa | gaa | cta | gtt | gca | gaa | ctg | 1763 |

```
                Glu Ile Ala Leu Leu Leu Gln Arg Lys Gln Glu Leu Val Ala Glu Leu
                            515                 520                 525 gac cag gat gaa aag gac cag caa aat aca tct cgc ctg gta cag gaa       1811
Asp Gln Asp Glu Lys Asp Gln Gln Asn Thr Ser Arg Leu Val Gln Glu
            530                 535                 540 cat aaa aag ctt tta gat gaa aac aaa agc ctt tct act tac tac cag       1859
His Lys Lys Leu Leu Asp Glu Asn Lys Ser Leu Ser Thr Tyr Tyr Gln
    545                 550                 555 caa tgc aaa aaa caa cta gag gtc atc aga agt cag cag cag aaa cga       1907
Gln Cys Lys Lys Gln Leu Glu Val Ile Arg Ser Gln Gln Gln Lys Arg
560                 565                 570                 575 caa ggc act tca tgattctctg ggaccgttac attttgaaat atgcaaagaa           1959
Gln Gly Thr Ser agactttttt tttaaggaaa ggaaaacctt ataatgacga ttcatgagtg ttagcttttt     2019
ggcgtgttct gaatgccaac tgcctatatt tgctgcattt ttttcattgt ttattttcct    2079
tttctcatgg tggacataca attttactgt ttcattgcat aacatggtag catctgtgac    2139
ttgaatgagc agcactttgc aacttcaaaa cagatgcagt gaactgtggc tgtatatgca    2199
tgctcattgt gtgaaggcta gcctaacaga acaggaggta tcaaactagc tgctatgtgc    2259
aaacagcgtc cattttttca tattagaggt ggaacctcaa gaatgacttt attcttgtat    2319
ctcatctcaa atattaata  attttttttcc caaaagatgg tatataccaa gttaaagaca   2379
gggtattata aatttagagt gattggtggt atattacgga aatacggaac ctttagggat    2439
agttccgtgt aagggctttg atgccagcat ccttggatca gtactgaact cagttccatc    2499
cgtaaaatat gtaaaggtaa gtggcagctg ctctatttaa tgaaagcagt tttaccggat    2559
tttgttagac taaaatttga ttgtgataca ttgaacaaaa tggaactcat ttttttttaag   2619 gagtaaagat tttctttaga gcacaatgga tctcgac                             2656

<210> SEQ ID NO 4
<211> LENGTH: 579
<212> TYPE: PRT
<213> ORGANISM: Homo sapiens

<400> SEQUENCE: 4

Met Ser Thr Ala Ser Ala Ala Ser Ser Ser Ser Ser Ser Ser Ala Gly
 1               5                  10                  15

Glu Met Ile Glu Ala Pro Ser Gln Val Leu Asn Phe Glu Glu Ile Asp
             20                  25                  30

Tyr Lys Glu Ile Glu Val Glu Glu Val Val Gly Arg Gly Ala Phe Gly
         35                  40                  45

Val Val Cys Lys Ala Lys Trp Arg Ala Lys Asp Val Ala Ile Lys Gln
     50                  55                  60

Ile Glu Ser Glu Ser Glu Arg Lys Ala Phe Ile Val Glu Leu Arg Gln
 65                  70                  75                  80

Leu Ser Arg Val Asn His Pro Asn Ile Val Lys Leu Tyr Gly Ala Cys
                 85                  90                  95

Leu Asn Pro Val Cys Leu Val Met Glu Tyr Ala Glu Gly Gly Ser Leu
            100                 105                 110

Tyr Asn Val Leu His Gly Ala Glu Pro Leu Pro Tyr Tyr Thr Ala Ala
        115                 120                 125

His Ala Met Ser Trp Cys Leu Gln Cys Ser Gln Gly Val Ala Tyr Leu
    130                 135                 140

His Ser Met Gln Pro Lys Ala Leu Ile His Arg Asp Leu Lys Pro Pro
145                 150                 155                 160
```

```
Asn Leu Leu Leu Val Ala Gly Gly Thr Val Leu Lys Ile Cys Asp Phe
                165                 170                 175
Gly Thr Ala Cys Asp Ile Gln Thr His Met Thr Asn Asn Lys Gly Ser
            180                 185                 190
Ala Ala Trp Met Ala Pro Glu Val Phe Glu Gly Ser Asn Tyr Ser Glu
        195                 200                 205
Lys Cys Asp Val Phe Ser Trp Gly Ile Ile Leu Trp Glu Val Ile Thr
    210                 215                 220
Arg Arg Lys Pro Phe Asp Glu Ile Gly Gly Pro Ala Phe Arg Ile Met
225                 230                 235                 240
Trp Ala Val His Asn Gly Thr Arg Pro Pro Leu Ile Lys Asn Leu Pro
                245                 250                 255
Lys Pro Ile Glu Ser Leu Met Thr Arg Cys Trp Ser Lys Asp Pro Ser
            260                 265                 270
Gln Arg Pro Ser Met Glu Glu Ile Val Lys Ile Met Thr His Leu Met
        275                 280                 285
Arg Tyr Phe Pro Gly Ala Asp Glu Pro Leu Gln Tyr Pro Cys Gln Tyr
    290                 295                 300
Ser Asp Glu Gly Gln Ser Asn Ser Ala Thr Ser Thr Gly Ser Phe Met
305                 310                 315                 320
Asp Ile Ala Ser Thr Asn Thr Ser Asn Lys Ser Asp Thr Asn Met Glu
                325                 330                 335
Gln Val Pro Ala Thr Asn Asp Thr Ile Lys Arg Leu Glu Ser Lys Leu
            340                 345                 350
Leu Lys Asn Gln Ala Lys Gln Gln Ser Glu Ser Gly Arg Leu Ser Leu
        355                 360                 365
Gly Ala Ser His Gly Ser Ser Val Glu Ser Leu Pro Pro Thr Ser Glu
    370                 375                 380
Gly Lys Arg Met Ser Ala Asp Met Ser Glu Ile Glu Ala Arg Ile Ala
385                 390                 395                 400
Ala Thr Thr Gly Asn Gly Gln Pro Arg Arg Arg Ser Ile Gln Asp Leu
                405                 410                 415
Thr Val Thr Gly Thr Glu Pro Gly Gln Val Ser Ser Arg Ser Ser Ser
            420                 425                 430
Pro Ser Val Arg Met Ile Thr Thr Ser Gly Pro Thr Ser Glu Lys Pro
        435                 440                 445
Thr Arg Ser His Pro Trp Thr Pro Asp Asp Ser Thr Asp Thr Asn Gly
    450                 455                 460
Ser Asp Asn Ser Ile Pro Met Ala Tyr Leu Thr Leu Asp His Gln Leu
465                 470                 475                 480
Gln Pro Leu Ala Pro Cys Pro Asn Ser Lys Glu Ser Met Ala Val Phe
                485                 490                 495
Glu Gln His Cys Lys Met Ala Gln Glu Tyr Met Lys Val Gln Thr Glu
            500                 505                 510
Ile Ala Leu Leu Leu Gln Arg Lys Gln Glu Leu Val Ala Glu Leu Asp
        515                 520                 525
Gln Asp Glu Lys Asp Gln Gln Asn Thr Ser Arg Leu Val Gln Glu His
    530                 535                 540
Lys Lys Leu Leu Asp Glu Asn Lys Ser Leu Ser Thr Tyr Tyr Gln Gln
545                 550                 555                 560
Cys Lys Lys Gln Leu Glu Val Ile Arg Ser Gln Gln Lys Arg Gln
                565                 570                 575
```

Gly Thr Ser

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Tyr Lys Asp Asp Asp Asp Lys
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His His His His His His
 1               5

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
ccggaattca tggcggcgca gaggagg                                        27

<210> SEQ ID NO 8
<211> LENGTH: 72
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
agctctagat cattatttat cgtcatcgtc tttgtagtca gaacctccgg tacccggtgc    60
tgtcaccacg ct                                                        72

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: Partial sequence of TAB 1 polypeptide

<400> SEQUENCE: 9

Gly Thr Gly Gly Ser
 1               5

<210> SEQ ID NO 10
<211> LENGTH: 1569
<212> TYPE: DNA
<213> ORGANISM: Homo sapiens
<220> FEATURE:

-continued

```
<221> NAME/KEY: CDS
<222> LOCATION: (7)..(1557)

<400> SEQUENCE: 10
```

| | | | | | | | | | | | | | | |
|---|---|---|---|---|---|---|---|---|---|---|---|---|---|---|
| gaattc | atg | gcg | gcg | cag | agg | agg | agc | ttg | ctg | cag | agt | gag | cag | cag | 48 |
| | Met | Ala | Ala | Gln | Arg | Arg | Ser | Leu | Leu | Gln | Ser | Glu | Gln | Gln | |
| | 1 | | | 5 | | | | | 10 | | | | | | |

| cca | agc | tgg | aca | gat | gac | ctg | cct | ctc | tgc | cac | ctc | tct | ggg | gtt | ggc | 96 |
|-----|-----|-----|-----|-----|-----|-----|-----|-----|-----|-----|-----|-----|-----|-----|-----|----|
| Pro | Ser | Trp | Thr | Asp | Asp | Leu | Pro | Leu | Cys | His | Leu | Ser | Gly | Val | Gly | |
| 15  |     |     |     | 20  |     |     |     |     | 25  |     |     |     |     | 30  |     | |

| tca | gcc | tcc | aac | cgc | agc | tac | tct | gct | gat | ggc | aag | ggc | act | gag | agc | 144 |
| Ser | Ala | Ser | Asn | Arg | Ser | Tyr | Ser | Ala | Asp | Gly | Lys | Gly | Thr | Glu | Ser | |
|     |     |     |     | 35  |     |     |     |     | 40  |     |     |     |     | 45  |     | |

| cac | ccg | cca | gag | gac | agc | tgg | ctc | aag | ttc | agg | agt | gag | aac | aac | tgc | 192 |
| His | Pro | Pro | Glu | Asp | Ser | Trp | Leu | Lys | Phe | Arg | Ser | Glu | Asn | Asn | Cys | |
|     |     | 50  |     |     |     |     | 55  |     |     |     |     | 60  |     |     |     | |

| ttc | ctg | tat | ggg | gtc | ttc | aac | ggc | tat | gat | ggc | aac | cga | gtg | acc | aac | 240 |
| Phe | Leu | Tyr | Gly | Val | Phe | Asn | Gly | Tyr | Asp | Gly | Asn | Arg | Val | Thr | Asn | |
|     |     |     |     | 65  |     |     |     |     | 70  |     |     |     |     | 75  |     | |

| ttc | gtg | gcc | cag | cgg | ctg | tcc | gca | gag | ctc | ctg | ctg | ggc | cag | ctg | aat | 288 |
| Phe | Val | Ala | Gln | Arg | Leu | Ser | Ala | Glu | Leu | Leu | Leu | Gly | Gln | Leu | Asn | |
|     | 80  |     |     |     |     | 85  |     |     |     |     | 90  |     |     |     |     | |

| gcc | gag | cac | gcc | gag | gcc | gat | gtg | cgg | cgt | gtg | ctg | ctg | cag | gcc | ttc | 336 |
| Ala | Glu | His | Ala | Glu | Ala | Asp | Val | Arg | Arg | Val | Leu | Leu | Gln | Ala | Phe | |
| 95  |     |     |     |     | 100 |     |     |     |     | 105 |     |     |     |     | 110 | |

| gat | gtg | gtg | gag | agg | agc | ttc | ctg | gag | tcc | att | gac | gac | gcc | ttg | gct | 384 |
| Asp | Val | Val | Glu | Arg | Ser | Phe | Leu | Glu | Ser | Ile | Asp | Asp | Ala | Leu | Ala | |
|     |     |     |     | 115 |     |     |     |     | 120 |     |     |     |     | 125 |     | |

| gag | aag | gca | agc | ctc | cag | tcg | caa | ttg | cca | gag | gga | gtc | cct | cag | cac | 432 |
| Glu | Lys | Ala | Ser | Leu | Gln | Ser | Gln | Leu | Pro | Glu | Gly | Val | Pro | Gln | His | |
|     |     |     | 130 |     |     |     |     | 135 |     |     |     |     | 140 |     |     | |

| cag | ctg | cct | cct | cag | tat | cag | aag | atc | ctt | gag | aga | ctc | aag | acg | tta | 480 |
| Gln | Leu | Pro | Pro | Gln | Tyr | Gln | Lys | Ile | Leu | Glu | Arg | Leu | Lys | Thr | Leu | |
|     |     |     | 145 |     |     |     |     | 150 |     |     |     |     | 155 |     |     | |

| gag | agg | gaa | att | tcg | gga | ggg | gcc | atg | gcc | gtt | gtg | gcg | gtc | ctt | ctc | 528 |
| Glu | Arg | Glu | Ile | Ser | Gly | Gly | Ala | Met | Ala | Val | Val | Ala | Val | Leu | Leu | |
|     | 160 |     |     |     |     | 165 |     |     |     |     | 170 |     |     |     |     | |

| aac | aac | aag | ctc | tac | gtc | gcc | aat | gtc | ggt | aca | aac | cgt | gca | ctt | tta | 576 |
| Asn | Asn | Lys | Leu | Tyr | Val | Ala | Asn | Val | Gly | Thr | Asn | Arg | Ala | Leu | Leu | |
| 175 |     |     |     |     | 180 |     |     |     |     | 185 |     |     |     |     | 190 | |

| tgc | aaa | tcg | aca | gtg | gat | ggg | ttg | cag | gtg | aca | cag | ctg | aac | gtg | gac | 624 |
| Cys | Lys | Ser | Thr | Val | Asp | Gly | Leu | Gln | Val | Thr | Gln | Leu | Asn | Val | Asp | |
|     |     |     |     | 195 |     |     |     |     | 200 |     |     |     |     | 205 |     | |

| cac | acc | aca | gag | aac | gag | gat | gag | ctc | ttc | cgt | ctt | tcg | cag | ctg | ggc | 672 |
| His | Thr | Thr | Glu | Asn | Glu | Asp | Glu | Leu | Phe | Arg | Leu | Ser | Gln | Leu | Gly | |
|     |     |     | 210 |     |     |     |     | 215 |     |     |     |     | 220 |     |     | |

| ttg | gat | gct | gga | aag | atc | aag | cag | gtg | ggg | atc | atc | tgt | ggg | cag | gag | 720 |
| Leu | Asp | Ala | Gly | Lys | Ile | Lys | Gln | Val | Gly | Ile | Ile | Cys | Gly | Gln | Glu | |
|     |     | 225 |     |     |     |     | 230 |     |     |     |     | 235 |     |     |     | |

| agc | acc | cgg | cgg | atc | ggg | gat | tac | aag | gtt | aaa | tat | ggc | tac | acg | gac | 768 |
| Ser | Thr | Arg | Arg | Ile | Gly | Asp | Tyr | Lys | Val | Lys | Tyr | Gly | Tyr | Thr | Asp | |
|     | 240 |     |     |     |     | 245 |     |     |     |     | 250 |     |     |     |     | |

| att | gac | ctt | ctc | agc | gct | gcc | aag | tcc | aaa | cca | atc | atc | gca | gag | cca | 816 |
| Ile | Asp | Leu | Leu | Ser | Ala | Ala | Lys | Ser | Lys | Pro | Ile | Ile | Ala | Glu | Pro | |
| 255 |     |     |     |     | 260 |     |     |     |     | 265 |     |     |     |     | 270 | |

| gaa | atc | cat | ggg | gca | cag | ccg | ctg | gat | ggg | gtg | acg | ggc | ttc | ttg | gtg | 864 |
| Glu | Ile | His | Gly | Ala | Gln | Pro | Leu | Asp | Gly | Val | Thr | Gly | Phe | Leu | Val | |
|     |     |     |     | 275 |     |     |     |     | 280 |     |     |     |     | 285 |     | |

| ctg | atg | tcg | gag | ggg | ttg | tac | aag | gcc | cta | gag | gca | gcc | cat | ggg | cct | 912 |
| Leu | Met | Ser | Glu | Gly | Leu | Tyr | Lys | Ala | Leu | Glu | Ala | Ala | His | Gly | Pro | |

-continued

```
            290                 295                 300
ggg cag gcc aac cag gag att gct gcg atg att gac act gag ttt gcc      960
Gly Gln Ala Asn Gln Glu Ile Ala Ala Met Ile Asp Thr Glu Phe Ala
            305                 310                 315 aag cag acc tcc ctg gac gca gtg gcc cag gcc gtc gtg gac cgg gtg     1008
Lys Gln Thr Ser Leu Asp Ala Val Ala Gln Ala Val Val Asp Arg Val
            320                 325                 330 aag cgc atc cac agc gac acc ttc gcc agt ggt ggg gag cgt gcc agg     1056
Lys Arg Ile His Ser Asp Thr Phe Ala Ser Gly Gly Glu Arg Ala Arg
335                 340                 345                 350 ttc tgc ccc cgg cac gag gac atg acc ctg cta gtg agg aac ttt ggc     1104
Phe Cys Pro Arg His Glu Asp Met Thr Leu Leu Val Arg Asn Phe Gly
                355                 360                 365 tac ccg ctg ggc gaa atg agc cag ccc aca ccg agc cca gcc cca gct     1152
Tyr Pro Leu Gly Glu Met Ser Gln Pro Thr Pro Ser Pro Ala Pro Ala
            370                 375                 380 gca gga gga cga gtg tac cct gtg tct gtg cca tac tcc agc gcc cag     1200
Ala Gly Gly Arg Val Tyr Pro Val Ser Val Pro Tyr Ser Ser Ala Gln
            385                 390                 395 agc acc agc aag acc agc gtg acc ctc tcc ctt gtc atg ccc tcc cag     1248
Ser Thr Ser Lys Thr Ser Val Thr Leu Ser Leu Val Met Pro Ser Gln
            400                 405                 410 ggc cag atg gtc aac ggg gct cac agt gct tcc acc ctg gac gaa gcc     1296
Gly Gln Met Val Asn Gly Ala His Ser Ala Ser Thr Leu Asp Glu Ala
415                 420                 425                 430 acc ccc acc ctc acc aac caa agc ccg acc tta acc ctg cag tcc acc     1344
Thr Pro Thr Leu Thr Asn Gln Ser Pro Thr Leu Thr Leu Gln Ser Thr
                435                 440                 445 aac acg cac acg cag agc agc agc tcc agc tct gac gga ggc ctc ttc     1392
Asn Thr His Thr Gln Ser Ser Ser Ser Ser Asp Gly Gly Leu Phe
            450                 455                 460 cgc tcc cgg ccc gcc cac tcg ctc ccg cct ggc gag gac ggt cgt gtt     1440
Arg Ser Arg Pro Ala His Ser Leu Pro Pro Gly Glu Asp Gly Arg Val
            465                 470                 475 gag ccc tat gtg gac ttt gct gag ttt tac cgc ctc tgg agc gtg gac     1488
Glu Pro Tyr Val Asp Phe Ala Glu Phe Tyr Arg Leu Trp Ser Val Asp
            480                 485                 490 cat ggc gag cag agc gtg gtg aca gca ccg ggt acc gga ggt tct gac     1536
His Gly Glu Gln Ser Val Val Thr Ala Pro Gly Thr Gly Gly Ser Asp
495                 500                 505                 510 tac aaa gac gat gac gat aaa taatgatcta ga                          1569
Tyr Lys Asp Asp Asp Asp Lys
                515
```

<210> SEQ ID NO 11
<211> LENGTH: 517
<212> TYPE: PRT
<213> ORGANISM: Homo sapiens

<400> SEQUENCE: 11

```
Met Ala Ala Gln Arg Arg Ser Leu Leu Gln Ser Glu Gln Gln Pro Ser
 1               5                  10                  15

Trp Thr Asp Asp Leu Pro Leu Cys His Leu Ser Gly Val Gly Ser Ala
                20                  25                  30

Ser Asn Arg Ser Tyr Ser Ala Asp Gly Lys Gly Thr Glu Ser His Pro
            35                  40                  45

Pro Glu Asp Ser Trp Leu Lys Phe Arg Ser Glu Asn Asn Cys Phe Leu
        50                  55                  60

Tyr Gly Val Phe Asn Gly Tyr Asp Gly Asn Arg Val Thr Asn Phe Val
```

-continued

```
             65                  70                  75                  80
    Ala Gln Arg Leu Ser Ala Glu Leu Leu Gly Gln Leu Asn Ala Glu
                     85                  90                  95
    His Ala Glu Ala Asp Val Arg Val Leu Leu Gln Ala Phe Asp Val
                    100                 105                 110
    Val Glu Arg Ser Phe Leu Glu Ser Ile Asp Asp Ala Leu Ala Glu Lys
                    115                 120                 125
    Ala Ser Leu Gln Ser Gln Leu Pro Glu Gly Val Pro Gln His Gln Leu
    130                 135                 140
    Pro Pro Gln Tyr Gln Lys Ile Leu Glu Arg Leu Lys Thr Leu Glu Arg
    145                 150                 155                 160
    Glu Ile Ser Gly Gly Ala Met Ala Val Ala Val Leu Leu Asn Asn
                    165                 170                 175
    Lys Leu Tyr Val Ala Asn Val Gly Thr Asn Arg Ala Leu Leu Cys Lys
                    180                 185                 190
    Ser Thr Val Asp Gly Leu Gln Val Thr Gln Leu Asn Val Asp His Thr
                    195                 200                 205
    Thr Glu Asn Glu Asp Glu Leu Phe Arg Leu Ser Gln Leu Gly Leu Asp
    210                 215                 220
    Ala Gly Lys Ile Lys Gln Val Gly Ile Ile Cys Gly Gln Glu Ser Thr
    225                 230                 235                 240
    Arg Arg Ile Gly Asp Tyr Lys Val Lys Tyr Gly Tyr Thr Asp Ile Asp
                    245                 250                 255
    Leu Leu Ser Ala Ala Lys Ser Lys Pro Ile Ile Ala Glu Pro Glu Ile
                    260                 265                 270
    His Gly Ala Gln Pro Leu Asp Gly Val Thr Gly Phe Leu Val Leu Met
                    275                 280                 285
    Ser Glu Gly Leu Tyr Lys Ala Leu Glu Ala Ala His Gly Pro Gly Gln
                    290                 295                 300
    Ala Asn Gln Glu Ile Ala Ala Met Ile Asp Thr Glu Phe Ala Lys Gln
    305                 310                 315                 320
    Thr Ser Leu Asp Ala Val Ala Gln Ala Val Val Asp Arg Val Lys Arg
                    325                 330                 335
    Ile His Ser Asp Thr Phe Ala Ser Gly Gly Glu Arg Ala Arg Phe Cys
                    340                 345                 350
    Pro Arg His Glu Asp Met Thr Leu Leu Val Arg Asn Phe Gly Tyr Pro
                    355                 360                 365
    Leu Gly Glu Met Ser Gln Pro Thr Pro Ser Pro Ala Pro Ala Ala Gly
    370                 375                 380
    Gly Arg Val Tyr Pro Val Ser Val Pro Tyr Ser Ser Ala Gln Ser Thr
    385                 390                 395                 400
    Ser Lys Thr Ser Val Thr Leu Ser Leu Val Met Pro Ser Gln Gly Gln
                    405                 410                 415
    Met Val Asn Gly Ala His Ser Ala Ser Thr Leu Asp Glu Ala Thr Pro
                    420                 425                 430
    Thr Leu Thr Asn Gln Ser Pro Thr Leu Thr Leu Gln Ser Thr Asn Thr
                    435                 440                 445
    His Thr Gln Ser Ser Ser Ser Ser Asp Gly Gly Leu Phe Arg Ser
                    450                 455                 460
    Arg Pro Ala His Ser Leu Pro Pro Gly Glu Asp Gly Arg Val Glu Pro
    465                 470                 475                 480
    Tyr Val Asp Phe Ala Glu Phe Tyr Arg Leu Trp Ser Val Asp His Gly
                    485                 490                 495
```

```
Glu Gln Ser Val Val Thr Ala Pro Gly Thr Gly Gly Ser Asp Tyr Lys
            500                 505                 510
Asp Asp Asp Asp Lys
        515

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
ccggaattca tgtctacagc ctctgcc                                         27

<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
agctctagat cattagtgat ggtgatggtg atgagatcca ccggtacctg aagtgccttg    60
tcgttt                                                               66

<210> SEQ ID NO 14
<211> LENGTH: 1788
<212> TYPE: DNA
<213> ORGANISM: Homo sapiens
<220> FEATURE:
<221> NAME/KEY: CDS
<222> LOCATION: (7)..(1776)

<400> SEQUENCE: 14
```

| | | | | | | | | | | | | | | | | |
|---|---|---|---|---|---|---|---|---|---|---|---|---|---|---|---|---|
| gaattc | atg | tct | aca | gcc | tct | gcc | gcc | tcc | tcc | tcc | tcc | tcg | tct | tcg | | 48 |
| | Met | Ser | Thr | Ala | Ser | Ala | Ala | Ser | Ser | Ser | Ser | Ser | Ser | Ser | | |
| | 1 | | | | 5 | | | | | 10 | | | | | | |
| gcc | ggt | gag | atg | atc | gaa | gcc | cct | tcc | cag | gtc | ctc | aac | ttt | gaa | gag | 96 |
| Ala | Gly | Glu | Met | Ile | Glu | Ala | Pro | Ser | Gln | Val | Leu | Asn | Phe | Glu | Glu | |
| 15 | | | | 20 | | | | | 25 | | | | | 30 | | |
| atc | gac | tac | aag | gag | atc | gag | gtg | gaa | gag | gtt | gtt | gga | aga | gga | gcc | 144 |
| Ile | Asp | Tyr | Lys | Glu | Ile | Glu | Val | Glu | Glu | Val | Val | Gly | Arg | Gly | Ala | |
| | | | 35 | | | | | 40 | | | | | 45 | | | |
| ttt | gga | gtt | gtt | tgc | aaa | gct | aag | tgg | aga | gca | aaa | gat | gtt | gct | att | 192 |
| Phe | Gly | Val | Val | Cys | Lys | Ala | Lys | Trp | Arg | Ala | Lys | Asp | Val | Ala | Ile | |
| | | 50 | | | | | 55 | | | | | 60 | | | | |
| aaa | caa | ata | gaa | agt | gaa | tct | gag | agg | aaa | gcg | ttt | att | gta | gag | ctt | 240 |
| Lys | Gln | Ile | Glu | Ser | Glu | Ser | Glu | Arg | Lys | Ala | Phe | Ile | Val | Glu | Leu | |
| | | | 65 | | | | | 70 | | | | | 75 | | | |
| cgg | cag | tta | tcc | cgt | gtg | aac | cat | cct | aat | att | gta | aag | ctt | tat | gga | 288 |
| Arg | Gln | Leu | Ser | Arg | Val | Asn | His | Pro | Asn | Ile | Val | Lys | Leu | Tyr | Gly | |
| | 80 | | | | | 85 | | | | | 90 | | | | | |
| gcc | tgc | ttg | aat | cca | gtg | tgt | ctt | gtg | atg | gaa | tat | gct | gaa | ggg | ggc | 336 |
| Ala | Cys | Leu | Asn | Pro | Val | Cys | Leu | Val | Met | Glu | Tyr | Ala | Glu | Gly | Gly | |
| 95 | | | | 100 | | | | | 105 | | | | | 110 | | |
| tct | tta | tat | aat | gtg | ctg | cat | ggt | gct | gaa | cca | ttg | cca | tat | tat | act | 384 |
| Ser | Leu | Tyr | Asn | Val | Leu | His | Gly | Ala | Glu | Pro | Leu | Pro | Tyr | Tyr | Thr | |
| | | | 115 | | | | | 120 | | | | | 125 | | | |
| gct | gcc | cac | gca | atg | agt | tgg | tgt | tta | cag | tgt | tcc | caa | gga | gtg | gct | 432 |

```
Ala Ala His Ala Met Ser Trp Cys Leu Gln Cys Ser Gln Gly Val Ala
        130                 135                 140 tat ctt cac agc atg caa ccc aaa gcg cta att cac agg gac ctg aaa      480
Tyr Leu His Ser Met Gln Pro Lys Ala Leu Ile His Arg Asp Leu Lys
        145                 150                 155 cca cca aac tta ctg ctg gtt gca ggg ggg aca gtt cta aaa att tgt      528
Pro Pro Asn Leu Leu Leu Val Ala Gly Gly Thr Val Leu Lys Ile Cys
160                 165                 170 gat ttt ggt aca gcc tgt gac att cag aca cac atg acc aat aac aag      576
Asp Phe Gly Thr Ala Cys Asp Ile Gln Thr His Met Thr Asn Asn Lys
175                 180                 185                 190 ggg agt gct gct tgg atg gca cct gaa gtt ttt gaa ggt agt aat tac      624
Gly Ser Ala Ala Trp Met Ala Pro Glu Val Phe Glu Gly Ser Asn Tyr
                195                 200                 205 agt gaa aaa tgt gac gtc ttc agc tgg ggt att att ctt tgg gaa gtg      672
Ser Glu Lys Cys Asp Val Phe Ser Trp Gly Ile Ile Leu Trp Glu Val
            210                 215                 220 ata acg cgt cgg aaa ccc ttt gat gag att ggt ggc cca gct ttc cga      720
Ile Thr Arg Arg Lys Pro Phe Asp Glu Ile Gly Gly Pro Ala Phe Arg
                225                 230                 235 atc atg tgg gct gtt cat aat ggt act cga cca cca ctg ata aaa aat      768
Ile Met Trp Ala Val His Asn Gly Thr Arg Pro Pro Leu Ile Lys Asn
        240                 245                 250 tta cct aag ccc att gag agc ctg atg act cgt tgt tgg tct aaa gat      816
Leu Pro Lys Pro Ile Glu Ser Leu Met Thr Arg Cys Trp Ser Lys Asp
255                 260                 265                 270 cct tcc cag cgc cct tca atg gag gaa att gtg aaa ata atg act cac      864
Pro Ser Gln Arg Pro Ser Met Glu Glu Ile Val Lys Ile Met Thr His
                275                 280                 285 ttg atg cgg tac ttt cca gga gca gat gag cca tta cag tat cct tgt      912
Leu Met Arg Tyr Phe Pro Gly Ala Asp Glu Pro Leu Gln Tyr Pro Cys
            290                 295                 300 cag tat tca gat gaa gga cag agc aac tct gcc acc agt aca ggc tca      960
Gln Tyr Ser Asp Glu Gly Gln Ser Asn Ser Ala Thr Ser Thr Gly Ser
                305                 310                 315 ttc atg gac att gct tct aca aat acg agt aac aaa agt gac act aat      1008
Phe Met Asp Ile Ala Ser Thr Asn Thr Ser Asn Lys Ser Asp Thr Asn
        320                 325                 330 atg gag caa gtt cct gcc aca aat gat act att aag cgc tta gaa tca      1056
Met Glu Gln Val Pro Ala Thr Asn Asp Thr Ile Lys Arg Leu Glu Ser
335                 340                 345                 350 aaa ttg ttg aaa aat cag gca aag caa cag agt gaa tct gga cgt tta      1104
Lys Leu Leu Lys Asn Gln Ala Lys Gln Gln Ser Glu Ser Gly Arg Leu
                355                 360                 365 agc ttg gga gcc tcc cat ggg agc agt gtg gag agc ttg ccc cca acc      1152
Ser Leu Gly Ala Ser His Gly Ser Ser Val Glu Ser Leu Pro Pro Thr
            370                 375                 380 tct gag ggc aag agg atg agt gct gac atg tct gaa ata gaa gct agg      1200
Ser Glu Gly Lys Arg Met Ser Ala Asp Met Ser Glu Ile Glu Ala Arg
                385                 390                 395 atc gcc gca acc aca ggc aac gga cag cca aga cgt aga tcc atc caa      1248
Ile Ala Ala Thr Thr Gly Asn Gly Gln Pro Arg Arg Arg Ser Ile Gln
        400                 405                 410 gac ttg act gta act gga aca gaa cct ggt cag gtg agc agt agg tca      1296
Asp Leu Thr Val Thr Gly Thr Glu Pro Gly Gln Val Ser Ser Arg Ser
415                 420                 425                 430 tcc agt ccc agt gtc aga atg att act acc tca gga cca acc tca gaa      1344
Ser Ser Pro Ser Val Arg Met Ile Thr Thr Ser Gly Pro Thr Ser Glu
                435                 440                 445
```

| | |
|---|---|
| aag cca act cga agt cat cca tgg acc cct gat gat tcc aca gat acc<br>Lys Pro Thr Arg Ser His Pro Trp Thr Pro Asp Asp Ser Thr Asp Thr<br>          450                       455                     460 | 1392 |
| aat gga tca gat aac tcc atc cca atg gct tat ctt aca ctg gat cac<br>Asn Gly Ser Asp Asn Ser Ile Pro Met Ala Tyr Leu Thr Leu Asp His<br>465                       470                     475 | 1440 |
| caa cta cag cct cta gca ccg tgc cca aac tcc aaa gaa tct atg gca<br>Gln Leu Gln Pro Leu Ala Pro Cys Pro Asn Ser Lys Glu Ser Met Ala<br>   480                     485                     490 | 1488 |
| gtg ttt gaa cag cat tgt aaa atg gca caa gaa tat atg aaa gtt caa<br>Val Phe Glu Gln His Cys Lys Met Ala Gln Glu Tyr Met Lys Val Gln<br>495                       500                     505                     510 | 1536 |
| aca gaa att gca ttg tta tta cag aga aag caa gaa cta gtt gca gaa<br>Thr Glu Ile Ala Leu Leu Leu Gln Arg Lys Gln Glu Leu Val Ala Glu<br>               515                     520                     525 | 1584 |
| ctg gac cag gat gaa aag gac cag caa aat aca tct cgc ctg gta cag<br>Leu Asp Gln Asp Glu Lys Asp Gln Gln Asn Thr Ser Arg Leu Val Gln<br>         530                     535                     540 | 1632 |
| gaa cat aaa aag ctt tta gat gaa aac aaa agc ctt tct act tac tac<br>Glu His Lys Lys Leu Leu Asp Glu Asn Lys Ser Leu Ser Thr Tyr Tyr<br>545                       550                     555 | 1680 |
| cag caa tgc aaa aaa caa cta gag gtc atc aga agt cag cag cag aaa<br>Gln Gln Cys Lys Lys Gln Leu Glu Val Ile Arg Ser Gln Gln Gln Lys<br>   560                     565                     570 | 1728 |
| cga caa ggc act tca ggt acc ggt gga tct cat cac cat cac cat cac<br>Arg Gln Gly Thr Ser Gly Thr Gly Gly Ser His His His His His His<br>575                       580                     585                     590 | 1776 |
| taatgatcta ga | 1788 |

<210> SEQ ID NO 15
<211> LENGTH: 590
<212> TYPE: PRT
<213> ORGANISM: Homo sapiens

<400> SEQUENCE: 15

Met Ser Thr Ala Ser Ala Ala Ser Ser Ser Ser Ser Ser Ser Ala Gly
1                 5                     10                   15

Glu Met Ile Glu Ala Pro Ser Gln Val Leu Asn Phe Glu Glu Ile Asp
               20                     25                     30

Tyr Lys Glu Ile Glu Val Glu Val Val Gly Arg Gly Ala Phe Gly
        35                     40                     45

Val Val Cys Lys Ala Lys Trp Arg Ala Lys Asp Val Ala Ile Lys Gln
     50                     55                     60

Ile Glu Ser Glu Ser Glu Arg Lys Ala Phe Ile Val Glu Leu Arg Gln
65                  70                     75                   80

Leu Ser Arg Val Asn His Pro Asn Ile Val Lys Leu Tyr Gly Ala Cys
                   85                     90                     95

Leu Asn Pro Val Cys Leu Val Met Glu Tyr Ala Glu Gly Gly Ser Leu
              100                     105                    110

Tyr Asn Val Leu His Gly Ala Glu Pro Leu Pro Tyr Tyr Thr Ala Ala
         115                     120                    125

His Ala Met Ser Trp Cys Leu Gln Cys Ser Gln Gly Val Ala Tyr Leu
   130                     135                     140

His Ser Met Gln Pro Lys Ala Leu Ile His Arg Asp Leu Lys Pro Pro
145                  150                     155                   160

Asn Leu Leu Leu Val Ala Gly Gly Thr Val Leu Lys Ile Cys Asp Phe
              165                     170                    175

```
Gly Thr Ala Cys Asp Ile Gln Thr His Met Thr Asn Asn Lys Gly Ser
                180                 185                 190

Ala Ala Trp Met Ala Pro Glu Val Phe Glu Gly Ser Asn Tyr Ser Glu
            195                 200                 205

Lys Cys Asp Val Phe Ser Trp Gly Ile Ile Leu Trp Glu Val Ile Thr
        210                 215                 220

Arg Arg Lys Pro Phe Asp Glu Ile Gly Pro Ala Phe Arg Ile Met
225                 230                 235                 240

Trp Ala Val His Asn Gly Thr Arg Pro Leu Ile Lys Asn Leu Pro
                245                 250                 255

Lys Pro Ile Glu Ser Leu Met Thr Arg Cys Trp Ser Lys Asp Pro Ser
            260                 265                 270

Gln Arg Pro Ser Met Glu Glu Ile Val Lys Ile Met Thr His Leu Met
        275                 280                 285

Arg Tyr Phe Pro Gly Ala Asp Glu Pro Leu Gln Tyr Pro Cys Gln Tyr
        290                 295                 300

Ser Asp Glu Gly Gln Ser Asn Ser Ala Thr Ser Thr Gly Ser Phe Met
305                 310                 315                 320

Asp Ile Ala Ser Thr Asn Thr Ser Asn Lys Ser Asp Thr Asn Met Glu
                325                 330                 335

Gln Val Pro Ala Thr Asn Asp Thr Ile Lys Arg Leu Glu Ser Lys Leu
            340                 345                 350

Leu Lys Asn Gln Ala Lys Gln Gln Ser Glu Ser Gly Arg Leu Ser Leu
        355                 360                 365

Gly Ala Ser His Gly Ser Ser Val Glu Ser Leu Pro Pro Thr Ser Glu
        370                 375                 380

Gly Lys Arg Met Ser Ala Asp Met Ser Glu Ile Glu Ala Arg Ile Ala
385                 390                 395                 400

Ala Thr Thr Gly Asn Gly Gln Pro Arg Arg Arg Ser Ile Gln Asp Leu
                405                 410                 415

Thr Val Thr Gly Thr Glu Pro Gly Gln Val Ser Ser Arg Ser Ser Ser
            420                 425                 430

Pro Ser Val Arg Met Ile Thr Thr Ser Gly Pro Thr Ser Glu Lys Pro
        435                 440                 445

Thr Arg Ser His Pro Trp Thr Pro Asp Asp Ser Thr Asp Thr Asn Gly
        450                 455                 460

Ser Asp Asn Ser Ile Pro Met Ala Tyr Leu Thr Leu Asp His Gln Leu
465                 470                 475                 480

Gln Pro Leu Ala Pro Cys Pro Asn Ser Lys Glu Ser Met Ala Val Phe
                485                 490                 495

Glu Gln His Cys Lys Met Ala Gln Glu Tyr Met Lys Val Gln Thr Glu
            500                 505                 510

Ile Ala Leu Leu Leu Gln Arg Lys Gln Glu Leu Val Ala Glu Leu Asp
        515                 520                 525

Gln Asp Glu Lys Asp Gln Gln Asn Thr Ser Arg Leu Val Gln Glu His
        530                 535                 540

Lys Lys Leu Leu Asp Glu Asn Lys Ser Leu Ser Thr Tyr Tyr Gln Gln
545                 550                 555                 560

Cys Lys Lys Gln Leu Glu Val Ile Arg Ser Gln Gln Lys Arg Gln
                565                 570                 575

Gly Thr Ser Gly Thr Gly Gly Ser His His His His His
            580                 585                 590
```

```
<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
ttctgaaggg cttccaccct ggacgaagcc accccaccc t                        41

<210> SEQ ID NO 17
<211> LENGTH: 69
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tataagcttt tattatttat cgtcatcgtc tttgtagtcc ggtgctgtca ccacgctctg   60
ctcgccatg                                                           69

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
ccggaattcc accatggagc ttcggcagtt atcc                               34

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
ccggaattcc tactgacaag gatactgt                                      28

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
tcttcagctg gggtattat                                                19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gctttatttc catgctgggc                                               20
```

```
<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
cggaattcga gctccggcag tgtcgcg                                         27

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
aactgcaggc tactgacaag gatactgtaa                                      30

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
ccgctcgagg aggcctcttc cgctcccggc c                                    31

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
ccgaattcct attacggtgc tgtcaccacg ctctg                                35

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
ccgctcgagg accctatgtg gactttgctg a                                    31

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
ccgctcgagg atatgtggac tttgctgagt t                                    31
```

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
ccgctcgagg agtggacttt gctgagtttt a                                      31

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
ccgctcgagg agactttgct gagttttacc g                                      31

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
ccgctcgagg atttgctgag ttttaccgcc t                                      31

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
ccgctcgagg agctgagttt taccgcctct g                                      31

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
ccgaattcct attagaggcg gtaaaactca gcaaagtc                               38

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
ccgaattcct attaagcaaa gtccacatag ggctc                                  35

<210> SEQ ID NO 34

<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
ccgaattcct attaaaagtc cacatagggc tc                                    32

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
ccgaattcct attagtccac atagggctca ac                                    32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
ccgaattcct attacacata gggctcaaca cg                                    32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
ccgaattcct attaataggg ctcaacacga cc                                    32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
ccgaattcct attagggctc aacacgaccg tc                                    32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
ccgaattcct attactcaac acgaccgtcc tc                                    32

<210> SEQ ID NO 40
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Val Glu Pro Tyr Val Asp Phe Ala Glu Phe Tyr Arg Gly Arg Lys
  1               5                  10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Gln Ser Pro Thr Leu Thr Leu Gln Ser Thr Asn Thr His Thr Gln
  1               5                  10                  15

<210> SEQ ID NO 42
<211> LENGTH: 1568
<212> TYPE: DNA
<213> ORGANISM: Homo sapiens
<220> FEATURE:
<221> NAME/KEY: CDS
<222> LOCATION: (11)..(1549)

<400> SEQUENCE: 42
gaattccacc atg gac tac aag gat gac gac gac aag atg gcg gcg cag         49
           Met Asp Tyr Lys Asp Asp Asp Asp Lys Met Ala Ala Gln
             1               5                  10 agg agg agc ttg ctg cag agt gag cag cag cca agc tgg aca gat gac         97
Arg Arg Ser Leu Leu Gln Ser Glu Gln Gln Pro Ser Trp Thr Asp Asp
 15                  20                  25 ctg cct ctc tgc cac ctc tct ggg gtt ggc tca gcc tcc aac cgc agc        145
Leu Pro Leu Cys His Leu Ser Gly Val Gly Ser Ala Ser Asn Arg Ser
 30                  35                  40                  45 tac tct gct gat ggc aag ggc act gag agc cac ccg cca gag gac agc        193
Tyr Ser Ala Asp Gly Lys Gly Thr Glu Ser His Pro Pro Glu Asp Ser
                 50                  55                  60 tgg ctc aag ttc agg agt gag aac aac tgc ttc ctg tat ggg gtc ttc        241
Trp Leu Lys Phe Arg Ser Glu Asn Asn Cys Phe Leu Tyr Gly Val Phe
             65                  70                  75 aac ggc tat gat ggc aac cga gtg acc aac ttc gtg gcc cag cgg ctg        289
Asn Gly Tyr Asp Gly Asn Arg Val Thr Asn Phe Val Ala Gln Arg Leu
         80                  85                  90 tcc gca gag ctc ctg ctg ggc cag ctg aat gcc gag cac gcc gag gcc        337
Ser Ala Glu Leu Leu Leu Gly Gln Leu Asn Ala Glu His Ala Glu Ala
 95                 100                 105 gat gtg cgg cgt gtg ctg ctg cag gcc ttc gat gtg gtg gag agg agc        385
Asp Val Arg Arg Val Leu Leu Gln Ala Phe Asp Val Val Glu Arg Ser
110                 115                 120                 125 ttc ctg gag tcc att gac gac gcc ttg gct gag aag gca agc ctc cag        433
Phe Leu Glu Ser Ile Asp Asp Ala Leu Ala Glu Lys Ala Ser Leu Gln
                130                 135                 140 tcg caa ttg cca gag gga gtc cct cag cac cag ctg cct cct cag tat        481
Ser Gln Leu Pro Glu Gly Val Pro Gln His Gln Leu Pro Pro Gln Tyr
            145                 150                 155 cag aag atc ctt gag aga ctc aag acg tta gag agg gaa att tcg gga        529
Gln Lys Ile Leu Glu Arg Leu Lys Thr Leu Glu Arg Glu Ile Ser Gly
        160                 165                 170
```

-continued

| | | |
|---|---|---|
| ggg gcc atg gcc gtt gtg gcg gtc ctt ctc aac aac aag ctc tac gtc<br>Gly Ala Met Ala Val Val Ala Val Leu Leu Asn Asn Lys Leu Tyr Val<br>175                    180                    185 | 577 |
| gcc aat gtc ggt aca aac cgt gca ctt tta tgc aaa tcg aca gtg gat<br>Ala Asn Val Gly Thr Asn Arg Ala Leu Leu Cys Lys Ser Thr Val Asp<br>190                    195                    200                    205 | 625 |
| ggg ttg cag gtg aca cag ctg aac gtg gac cac acc aca gag aac gag<br>Gly Leu Gln Val Thr Gln Leu Asn Val Asp His Thr Thr Glu Asn Glu<br>                    210                    215                    220 | 673 |
| gat gag ctc ttc cgt ctt tcg cag ctg ggc ttg gat gct gga aag atc<br>Asp Glu Leu Phe Arg Leu Ser Gln Leu Gly Leu Asp Ala Gly Lys Ile<br>            225                    230                    235 | 721 |
| aag cag gtg ggg atc atc tgt ggg cag gag agc acc cgg cgg atc ggg<br>Lys Gln Val Gly Ile Ile Cys Gly Gln Glu Ser Thr Arg Arg Ile Gly<br>        240                    245                    250 | 769 |
| gat tac aag gtt aaa tat ggc tac acg gac att gac ctt ctc agc gct<br>Asp Tyr Lys Val Lys Tyr Gly Tyr Thr Asp Ile Asp Leu Leu Ser Ala<br>255                    260                    265 | 817 |
| gcc aag tcc aaa cca atc atc gca gag cca gaa atc cat ggg gca cag<br>Ala Lys Ser Lys Pro Ile Ile Ala Glu Pro Glu Ile His Gly Ala Gln<br>270                    275                    280                    285 | 865 |
| ccg ctg gat ggg gtg acg ggc ttc ttg gtg ctg atg tcg gag ggg ttg<br>Pro Leu Asp Gly Val Thr Gly Phe Leu Val Leu Met Ser Glu Gly Leu<br>                    290                    295                    300 | 913 |
| tac aag gcc cta gag gca gcc cat ggg cct ggg cag gcc aac cag gag<br>Tyr Lys Ala Leu Glu Ala Ala His Gly Pro Gly Gln Ala Asn Gln Glu<br>            305                    310                    315 | 961 |
| att gct gcg atg att gac act gag ttt gcc aag cag acc tcc ctg gac<br>Ile Ala Ala Met Ile Asp Thr Glu Phe Ala Lys Gln Thr Ser Leu Asp<br>                320                    325                    330 | 1009 |
| gca gtg gcc cag gcc gtc gtg gac cgg gtg aag cgc atc cac agc gac<br>Ala Val Ala Gln Ala Val Val Asp Arg Val Lys Arg Ile His Ser Asp<br>335                    340                    345 | 1057 |
| acc ttc gcc agt ggt ggg gag cgt gcc agg ttc tgc ccc cgg cac gag<br>Thr Phe Ala Ser Gly Gly Glu Arg Ala Arg Phe Cys Pro Arg His Glu<br>350                    355                    360                    365 | 1105 |
| gac atg acc ctg cta gtg agg aac ttt ggc tac ccg ctg ggc caa atg<br>Asp Met Thr Leu Leu Val Arg Asn Phe Gly Tyr Pro Leu Gly Gln Met<br>                370                    375                    380 | 1153 |
| agc cag ccc aca ccg agc cca gcc cca gct gca gga gga cga gtg tac<br>Ser Gln Pro Thr Pro Ser Pro Ala Pro Ala Ala Gly Gly Arg Val Tyr<br>            385                    390                    395 | 1201 |
| cct gtg tct gtg cca tac tcc agc gcc cag agc acc agc aag acc agc<br>Pro Val Ser Val Pro Tyr Ser Ser Ala Gln Ser Thr Ser Lys Thr Ser<br>        400                    405                    410 | 1249 |
| gtg acc ctc tcc ctt gtc atg ccc tcc cag ggc cag atg gtc aac ggg<br>Val Thr Leu Ser Leu Val Met Pro Ser Gln Gly Gln Met Val Asn Gly<br>415                    420                    425 | 1297 |
| gct cac agt gct tcc acc ctg gac gaa gcc acc ccc acc ctc acc aac<br>Ala His Ser Ala Ser Thr Leu Asp Glu Ala Thr Pro Thr Leu Thr Asn<br>430                    435                    440                    445 | 1345 |
| caa agc ccg acc tta acc ctg cag tcc acc aac acg cac acg cag agc<br>Gln Ser Pro Thr Leu Thr Leu Gln Ser Thr Asn Thr His Thr Gln Ser<br>                450                    455                    460 | 1393 |
| agc agc tcc agc tct gac gga ggc ctc ttc cgc tcc cgg ccc gcc cac<br>Ser Ser Ser Ser Ser Asp Gly Gly Leu Phe Arg Ser Arg Pro Ala His<br>            465                    470                    475 | 1441 |
| tcg ctc ccg cct ggc gag gac ggt cgt gtt gag ccc tat gtg gac ttt<br>Ser Leu Pro Pro Gly Glu Asp Gly Arg Val Glu Pro Tyr Val Asp Phe | 1489 |

```
                    480             485             490
gct gag ttt tac cgc ctc tgg agc gtg gac cat ggc gag cag agc gtg      1537
Ala Glu Phe Tyr Arg Leu Trp Ser Val Asp His Gly Glu Gln Ser Val
        495                 500                 505 gtg aca gca ccg tgatgagcgg ccgcatcgt                                 1568
Val Thr Ala Pro
510
```

<210> SEQ ID NO 43
<211> LENGTH: 513
<212> TYPE: PRT
<213> ORGANISM: Homo sapiens

<400> SEQUENCE: 43

```
Met Asp Tyr Lys Asp Asp Asp Lys Met Ala Ala Gln Arg Arg Ser
 1               5                  10                  15

Leu Leu Gln Ser Glu Gln Gln Pro Ser Trp Thr Asp Leu Pro Leu
                20                  25                  30

Cys His Leu Ser Gly Val Gly Ser Ala Ser Asn Arg Ser Tyr Ser Ala
                35                  40                  45

Asp Gly Lys Gly Thr Glu Ser His Pro Pro Glu Asp Ser Trp Leu Lys
         50                 55                  60

Phe Arg Ser Glu Asn Asn Cys Phe Leu Tyr Gly Val Phe Asn Gly Tyr
 65                  70                  75                  80

Asp Gly Asn Arg Val Thr Asn Phe Val Ala Gln Arg Leu Ser Ala Glu
                 85                  90                  95

Leu Leu Leu Gly Gln Leu Asn Ala Glu His Ala Glu Ala Asp Val Arg
                100                 105                 110

Arg Val Leu Leu Gln Ala Phe Asp Val Val Glu Arg Ser Phe Leu Glu
            115                 120                 125

Ser Ile Asp Asp Ala Leu Ala Glu Lys Ala Ser Leu Gln Ser Gln Leu
    130                 135                 140

Pro Glu Gly Val Pro Gln His Gln Leu Pro Pro Gln Tyr Gln Lys Ile
145                 150                 155                 160

Leu Glu Arg Leu Lys Thr Leu Glu Arg Glu Ile Ser Gly Gly Ala Met
                165                 170                 175

Ala Val Val Ala Val Leu Leu Asn Asn Lys Leu Tyr Val Ala Asn Val
                180                 185                 190

Gly Thr Asn Arg Ala Leu Leu Cys Lys Ser Thr Val Asp Gly Leu Gln
            195                 200                 205

Val Thr Gln Leu Asn Val Asp His Thr Thr Glu Asn Glu Asp Glu Leu
    210                 215                 220

Phe Arg Leu Ser Gln Leu Gly Leu Asp Ala Gly Lys Ile Lys Gln Val
225                 230                 235                 240

Gly Ile Ile Cys Gly Gln Glu Ser Thr Arg Arg Ile Gly Asp Tyr Lys
                245                 250                 255

Val Lys Tyr Gly Tyr Thr Asp Ile Asp Leu Leu Ser Ala Ala Lys Ser
            260                 265                 270

Lys Pro Ile Ile Ala Glu Pro Glu Ile His Gly Ala Gln Pro Leu Asp
        275                 280                 285

Gly Val Thr Gly Phe Leu Val Leu Met Ser Glu Gly Leu Tyr Lys Ala
    290                 295                 300

Leu Glu Ala Ala His Gly Pro Gly Gln Ala Asn Gln Glu Ile Ala Ala
305                 310                 315                 320

Met Ile Asp Thr Glu Phe Ala Lys Gln Thr Ser Leu Asp Ala Val Ala
```

```
                        325                 330                 335
Gln Ala Val Val Asp Arg Val Lys Arg Ile His Ser Asp Thr Phe Ala
                340                 345                 350
Ser Gly Gly Glu Arg Ala Arg Phe Cys Pro Arg His Glu Asp Met Thr
            355                 360                 365
Leu Leu Val Arg Asn Phe Gly Tyr Pro Leu Gly Gln Met Ser Gln Pro
        370                 375                 380
Thr Pro Ser Pro Ala Pro Ala Ala Gly Gly Arg Val Tyr Pro Val Ser
385                 390                 395                 400
Val Pro Tyr Ser Ser Ala Gln Ser Thr Ser Lys Thr Ser Val Thr Leu
                405                 410                 415
Ser Leu Val Met Pro Ser Gln Gly Gln Met Val Asn Gly Ala His Ser
                420                 425                 430
Ala Ser Thr Leu Asp Glu Ala Thr Pro Thr Leu Thr Asn Gln Ser Pro
            435                 440                 445
Thr Leu Thr Leu Gln Ser Thr Asn Thr His Thr Gln Ser Ser Ser Ser
        450                 455                 460
Ser Ser Asp Gly Gly Leu Phe Arg Ser Arg Pro Ala His Ser Leu Pro
465                 470                 475                 480
Pro Gly Glu Asp Gly Arg Val Glu Pro Tyr Val Asp Phe Ala Glu Phe
                485                 490                 495
Tyr Arg Leu Trp Ser Val Asp His Gly Glu Gln Ser Val Val Thr Ala
                500                 505                 510
Pro

<210> SEQ ID NO 44
<211> LENGTH: 51
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
cccgaattcc accatggact acaaggatga cgacgacaag atggcggcgc a         51

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
gatgcggccg ctcatcacgg tgctgtcacc acgct                            35

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
ccgctcgagg acggcccgcc cactcgctcc cgcc                             34

<210> SEQ ID NO 47
<211> LENGTH: 34
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
ccgctcgagg actcccgcct ggcgaggacg gtcg                          34

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
ccgctcgagg agacggtcgt gttgagccct atgt                          34
```

METHOD OF SCREENING TGF-β INHIBITORY SUBSTANCES

TECHNICAL FIELD

The present invention relates to a method for screening substances that inhibit binding between TAK1 and TAB1. The present invention also relates to a method for screening substances that inhibit the signal transduction of transforming growth factor-β (TGF-β). The present invention further relates to substances and uses thereof obtainable by the method for screening substances that inhibit binding between TAK1 and TAB1.

BACKGROUND ART

Transforming growth factor-β (TGF-β) is a multilfunctional factor that controls various aspects of cell functions. As one such function, TGF-β is responsible for the repair and regeneration of tissues associated with various injuries (Border, W. A. & Noble, N. A., The New England Journal of Medicine (1994) 331, 1286–1292).

An abnormal production of TGF-β in chronic injuries can sometimes disturb balances in the repair and regeneration of tissues resulting in pathological fibrosis. As a pathological condition in which the balance of TGF-β production has been disturbed, hepatic fibrosis is known. It has been elucidated that TGF-β acts as a main causative agent of fibrosis of various organs such as the liver, by enhancing the production of extracellular matrix protein that can cause fibrosis, inhibiting the synthesis of proteolytic enzymes of extracellular matrix, and by inducing substances that inhibit proteolytic enzymes of extracellular matrix (Border, W. A. & Noble, N. A., The New England Journal of Medicine (1994) 331, 1286–1292).

Other known functions of TGF-β include the activity of inhibiting cellular growth (Moses, H. L. et al., Cell (1990) 63, 245–247), the activity of migrating monocytes (Wahl, S. M. et al., Proc. Natl. Acad. Sci. U.S.A. (1987) 84, 5788–5792), the activity of inducing biologically active substances (Wahl, S. M. et al., Proc. Natl. Acad. Sci. U.S.A. (1987) 84, 5788–5792), the activity of facilitating the deposition of amyloid β protein (Wyss-Coray, T. et al., Nature (1997) 389, 603–606), and the like.

TGF-β transduces its signals through heteromer complexes of type I and type II TGF-β receptors and transmembrane proteins containing the serine- and threonine-specific kinase domains at the side of cytoplasm (Wrana, J. L. et al., Nature (1994) 370, 341; Kingsley, D. M. et al., Genes Dev. (1994) 8, 133). However, much of the mechanism of signaling downward from the TGF-β receptor into the cell on the molecular level remains to be elucidated.

As a series of systems involved in the signal transduction of the TGF-β superfamily, mitogen-activated protein kinase (MAPK) is known.

The MAPK system is a conserved eukaryotic signaling system that converts signals of a receptor into various functions. The MAPK system contains three types of protein kinases, i.e. mitogen-activated protein kinase kinase kinase (MAPKKK), mitogen-activated protein kinase kinase (MAPKK), and mitogen-activated protein kinase (MAPK). MAPK is activated through phosphorylation by MAPKK. MAPKK is activated through phosphorylation by MAP-KKK (Nishida, E. et al., Trends Biochem. Sci. (1993) 18, 128; Blumer, K. J. et al., Trends Biochem. Sci. (1993) 19, 236; David R. J. et al., Trends Biochem. Sci. (1993) 19, 470; Marchall, C. J. et al., Cell (1995) 80, 179).

TAK1 (TGF-β-activated kinase 1), that is a member of the MAPKKK family that functions in the signaling system of biologically active substances and that belongs to the TGF-β superfamily, was identified by Yamaguchi, K. et al. (Yamaguchi, K. et al., Science (1995) 270, 2008).

TAB1 (TAK1 binding protein 1), a protein involved in the signaling system of TGF-β that binds to and activates TAK1, was identified by Shibuya, H. et al. (Shibuya, H. et al., Science (1996) 272, 1179–1182).

Although TAB1 transduces the signal of TGF-β by binding to TAK1 and activating TAK1 kinase activity, no attempts have been made so far to search for substances that inhibit binding between TAK1 and TAB1 in order to suppress or activate signal transduction of TGF-β by focusing on the binding between TAK1 and TAB1.

DISCLOSER OF THE INVENTION

The present invention is intended to provide a method for screening substances that inhibit binding between TAK1 and TAB1. The present invention is also intended to provide a method for screening substances that suppress or activate the signal transduction of TGF-β. The present invention further is intended to provide substances that are obtainable by a method for screening substances that inhibit binding between TAK1 and TAB1.

Thus, the present invention provides (1) a method for screening substances that inhibit binding between a TAK1 polypeptide and a TAB1 polypeptide, which method comprises contacting the TAB1 polypeptide to the TAK1 polypeptide and a test sample and then detecting or determining the TAK1 polypeptide that is bound to the TAB1 polypeptide. Preferably, the TAB1 polypeptide is a TAB1 polypeptide that has been bound to a support. A preferred support is beads or a plate. In another preferred embodiment, the contact between a TAK1 polypeptide, a TAB1 polypeptide and a test sample is carried out in a homogeneous system.

The present invention also provides (2) a method for screening substances that inhibit binding between a TAK1 polypeptide and a TAB1 polypeptide, which method comprises contacting the TAK1 polypeptide to the TAB1 polypeptide and a test sample, and then detecting or determining the TAB1 polypeptide that is bound to the TAK1 polypeptide. Preferably, the TAK1 polypeptide is a TAK1 polypeptide that has been bound to a support. A preferred support is beads or a plate. In another preferred embodiment, the contact between a TAK1 polypeptide, a TAB1 polypeptide and a test sample is carried out in a homogeneous system.

The present invention also provides (3) a screening method described in the above (1) and (2), which method comprises using a TAB1 polypeptide having an amino acid sequence comprising Met at amino acid position 1 to Pro at amino acid position 504 of the amino acid sequence as set forth in SEQ ID NO: 2, or having an amino acid sequence modified by the substitution, deletion and/or addition of one or a plurality of amino acid residues of the amino acid sequence as set forth in SEQ ID NO: 2 and maintaining the biological activity of the TAB1 polypeptide; and/or a TAK1 polypeptide having an amino acid sequence comprising Met at amino acid position 1 to Ser at amino acid position 579 of the amino acid sequence as set forth in SEQ ID NO: 4, or having an amino acid sequence modified by the substitution, deletion and/or addition of one or a plurality of amino acid residues of the amino acid sequence as set forth in SEQ ID NO: 4 and maintaining the biological activity of the TAK1 polypeptide.

The present invention also provides (4) a screening method described in the above (1) to (3), which comprises using a TAK1 polypeptide fused to another peptide or polypeptide and/or a TAB1 polypeptide fused to another peptide or polypeptide.

The present invention also provides (5) a method for screening substances that inhibit binding between a TAK1 polypeptide and a TAB1 polypeptide, which method comprises contacting the TAB1 polypeptide to the labeled TAK1 polypeptide and a test sample, and then detecting or determining the labeled TAK1 polypeptide that is bound to the TAB1 polypeptide. Preferably, the TAB1 polypeptide is a TAB1 polypeptide that has been bound to a support. A preferred support is beads or a plate. In another preferred embodiment, the contact between a TAK1 polypeptide, a TAB1 polypeptide and a test sample is carried out in a homogeneous system.

The present invention also provides (6) a method for screening substances that inhibit binding between a TAK1 polypeptide and a TAB1 polypeptide, which method comprises contacting the TAK1 polypeptide to the labeled TAB1 polypeptide and a test sample, and then detecting or determining the labeled TAB1 polypeptide that is bound to the TAK1 polypeptide. Preferably, the TAK1 polypeptide is a TAK1 polypeptide that has been bound to a support. A preferred support is beads or a plate. In another preferred embodiment, the contact between a TAK1 polypeptide, a TAB1 polypeptide and a test sample is carried out in a homogeneous system.

The present invention also provides (7) a screening method described in the above (5) and (6), which method comprises using a TAB1 polypeptide having an amino acid sequence comprising Met at amino acid position 1 to Pro at amino acid position 504 of the amino acid sequence as set forth in SEQ ID NO: 2 or having an amino acid sequence modified by the substitution, deletion and/or addition of one or a plurality of amino acid residues of the amino acid sequence as set forth in SEQ ID NO: 2 and maintaining the biological activity of the TAB1 polypeptide; and/or a TAK1 polypeptide having an amino acid sequence comprising Met at amino acid position 1 to Ser at amino acid position 579 of the amino acid sequence as set forth in SEQ ID NO: 4 or having an amino acid sequence modified by the substitution, deletion and/or addition of one or a plurality of amino acid residues of the amino acid sequence as set forth in SEQ ID NO: 4 and maintaining the biological activity of the TAK1 polypeptide.

The present invention also provides (8) a screening method described in the above (5) to (7), which method comprises using a TAK1 polypeptide fused to another peptide or polypeptide and/or a TAB1 polypeptide fused to another peptide or polypeptide. Preferably, said labeled TAK1 polypeptide or said labeled TAB1 polypeptide is a TAK1 polypeptide or a TAB1 polypeptide that is labeled with a radioisotope, an enzyme or a fluorescent substance.

The present invention also provides (9) a method for screening substances that inhibit binding between a TAK1 polypeptide and a TAB1 polypeptide, which method comprises contacting the TAB1 polypeptide to the TAK1 polypeptide and a test sample, and then detecting or determining the TAK1 polypeptide that is bound to the TAB1 polypeptide by a primary antibody against the TAK1 polypeptide. Preferably, the TAB1 polypeptide is a TAB1 polypeptide that has been bound to a support. A preferred support is beads or a plate. Preferably, the primary antibody is a primary antibody that is labeled with a radioisotope or an enzyme. In another preferred embodiment, the contact between a TAK1 polypeptide, a TAB1 polypeptide and a test sample is carried out in a homogeneous system.

The present invention also provides (10) a method for screening substances that inhibit binding between a TAK1 polypeptide and a TAB1 polypeptide, which method comprises contacting the TAK1 polypeptide to the TAB1 polypeptide and a test sample, and then detecting or determining the TAB1 polypeptide that is bound to the TAK1 polypeptide by a primary antibody against the TAB1 polypeptide. Preferably, the TAK1 polypeptide is a TAK1 polypeptide that has been bound to a support. A preferred support is beads or a plate. Preferably, the primary antibody is a primary antibody that is labeled with a radioisotope, an enzyme or a fluorescent substance. In another preferred embodiment, the contact between a TAK1 polypeptide, a TAB1 polypeptide and a test sample is carried out in a homogeneous system.

The present invention also provides (11) a screening method described in the above (9) and (10), which method comprises using a TAB1 polypeptide having an amino acid sequence comprising Met at amino acid position 1 to Pro at amino acid position 504 of the amino acid sequence as set forth in SEQ ID NO: 2 or having an amino acid sequence modified by the substitution, deletion and/or addition of one or a plurality of amino acid residues of the amino acid sequence as set forth in SEQ ID NO: 2 and maintaining the biological activity of the TAB1 polypeptide.

a TAK1 polypeptide having an amino acid sequence comprising Met at amino acid position 1 to Ser at amino acid position 579 of the amino acid sequence as set forth in SEQ ID NO: 4 or having an amino acid sequence modified by the substitution, deletion and/or addition of one or a plurality of amino acid residues of the amino acid sequence as set forth in SEQ ID NO: 4 and maintaining the biological activity of the TAK1 polypeptide.

The present invention also provides (12) a screening method described in the above (9) to (11), which method comprises using a TAK1 polypeptide fused to another peptide or polypeptide and/or a TAB1 polypeptide fused to another peptide or polypeptide.

The present invention also provides (13) a method for screening substances that inhibit binding between a TAK1 polypeptide and a TAB1 polypeptide, which method comprises contacting the TAB1 polypeptide or the TAB1 polypeptide fused to another peptide or polypeptide to the TAK1 polypeptide fused to another peptide or polypeptide and a test sample, and then detecting or determining the TAK1 polypeptide fused to another peptide or polypeptide said TAK1 polypeptide being bound to the TAB1 polypeptide or the TAB1 polypeptide fused to another peptide or polypeptide by a primary antibody against the other peptide or polypeptide. Preferably, the TAB1 polypeptide or the TAB1 polypeptide fused to another peptide or polypeptide is a TAB1 polypeptide or a TAB1 polypeptide fused to another peptide or polypeptide, that has been bound to a support. A preferred support is beads or a plate. Preferably, the primary antibody is a primary antibody that is labeled with a radioisotope or an enzyme. In another preferred embodiment, the contact between a TAK1 polypeptide, a TAB1 polypeptide and a test sample is carried out in a homogeneous system.

The present invention also provides (14) a method for screening substances that inhibit binding between a TAK1 polypeptide and a TAB1 polypeptide, which method comprises contacting the TAK1 polypeptide or the TAK1 polypeptide fused to another peptide or polypeptide to the TAB1 polypeptide fused to another peptide or polypeptide and a test sample, and then detecting or determining the TAB1 polypeptide fused to another peptide or polypeptide said TAB1 polypeptide being bound to the TAK1 polypeptide or the TAK1 polypeptide fused to another peptide or polypeptide, by a primary antibody against the other peptide or polypeptide. Preferably, the TAK1 polypeptide or the TAK1 polypeptide fused to another peptide or polypeptide is a TAK1 polypeptide or a TAK1 polypeptide fused to another peptide or polypeptide, that has been bound to a support. A preferred support is beads or a plate. Preferably, the primary antibody is a primary antibody that is labeled with a radioisotope, an enzyme a fluorescent substance. In another preferred embodiment, the contact between a TAK1 polypeptide, a TAB1 polypeptide and a test sample is carried out in a homogeneous system.

The present invention also provides (15) a screening method described in the above (13) and (14), which method comprises using a TAB1 polypeptide having an amino acid sequence comprising Met at amino acid position 1 to Pro at amino acid position 504 of the amino acid sequence as set forth in SEQ ID NO: 2 or having an amino acid sequence modified by the substitution, deletion and/or addition of one or a plurality of amino acid residues of the amino acid sequence as set forth in SEQ ID NO: 2 and maintaining the biological activity of the TAB1 polypeptide; and/or a TAK1 polypeptide having an amino acid sequence comprising Met at amino acid position 1 to Ser at amino acid position 579 of the amino acid sequence as set forth in SEQ ID NO: 4 or having an amino acid sequence modified by the substitution, deletion and/or addition of one or a plurality of amino acid residues of the amino acid sequence as set forth in SEQ ID NO: 4 and maintaining the biological activity of the TAK1 polypeptide.

The present invention also provides (16) a method for screening substances that inhibit binding between a TAK1 polypeptide and a TAB1 polypeptide, which method comprises contacting the TAB1 polypeptide to the TAK1 polypeptide and a test sample, and then detecting or determining the TAK1 polypeptide that is bound to the TAB1 polypeptide by a primary antibody against the TAK1 polypeptide and a secondary antibody against the primary antibody. Preferably, the TAB1 polypeptide is a TAB1 polypeptide that has been bound to a support. A preferred support is beads or a plate. Preferably, the secondary antibody is a secondary antibody that is labeled with a radioisotope, an enzyme or a fluorescent substance. In another preferred embodiment, the contact between a TAK1 polypeptide, a TAB1 polypeptide and a test sample is carried out in a homogeneous system.

The present invention also provides (17) a method for screening substances that inhibit binding between a TAK1 polypeptide and a TAB1 polypeptide, which method comprises contacting the TAK1 polypeptide to the TAB1 polypeptide and a test sample, and then detecting or determining the TAB1 polypeptide that is bound to the TAK1 polypeptide by a primary antibody against the TAB1 polypeptide and a secondary antibody against the primary antibody. Preferably, the TAK1 polypeptide is a TAK1 polypeptide that has been bound to a support. A preferred support is beads or a plate. Preferably, the secondary antibody is a secondary antibody that is labeled with a radioisotope, an enzyme or a fluorescent substance. In another preferred embodiment, the contact between a TAK1 polypeptide, a TAB1 polypeptide and a test sample is carried out in a homogeneous system.

The present invention also provides (18) a screening method described in the above (16) and (17), which method comprises using a TAB1 polypeptide having an amino acid sequence comprising Met at amino acid position 1 to Pro at amino acid position 504 of the amino acid sequence as set forth in SEQ ID NO: 2 or having an amino acid sequence modified by the substitution, deletion and/or addition of one or a plurality of amino acid residues of the amino acid sequence as set forth in SEQ ID NO: 2 and maintaining the biological activity of the TAB1 polypeptide; and/or a TAK1 polypeptide having an amino acid sequence comprising Met at amino acid position 1 to Ser at amino acid position 579 of the amino acid sequence as set forth in SEQ ID NO: 4 or having an amino acid sequence modified by the substitution, deletion and/or addition of one or a plurality of amino acid residues of the amino acid sequence as set forth in SEQ ID NO: 4 and maintaining the biological activity of the TAK1 polypeptide.

The present invention also provides (19) a screening method described in the above (16) to (18), which method comprises using a TAK1 polypeptide fused to another peptide or polypeptide and/or a TAB1 polypeptide fused to another peptide or polypeptide.

The present invention also provides (20) a method for screening substances that inhibit binding between a TAK1 polypeptide and a TAB1 polypeptide, which method comprises contacting the TAB1 polypeptide or the TAB1 polypeptide fused to another peptide or polypeptide to the TAK1 polypeptide fused to another peptide or polypeptide and a test sample, and then detecting or determining the TAK1 polypeptide fused to another peptide or polypeptide said TAK1 polypeptide being bound to the TAB1 polypeptide or the TAB1 polypeptide fused to another peptide or polypeptide, by a primary antibody against the other peptide or polypeptide and a secondary antibody against the primary antibody. Preferably, the TAB1 polypeptide or the TAB1 polypeptide fused to another peptide or polypeptide is a TAB1 polypeptide or the TAB1 polypeptide fused to another peptide or polypeptide, that has been bound to a support. A preferred support is beads or a plate. Preferably, the secondary antibody is a primary antibody that is labeled with a radioisotope, an enzyme or a fluorescent substance. In another preferred embodiment, the contact between a TAK1 polypeptide, a TAB1 polypeptide and a test sample is carried out in a homogeneous system.

The present invention also provides (21) a method for screening substances that inhibit binding between a TAK1 polypeptide and a TAB1 polypeptide, which method comprises contacting the TAK1 polypeptide or the TAK1 polypeptide fused to another peptide or polypeptide to the TAB1 polypeptide fused to another peptide or polypeptide and a test sample, and then detecting or determining the TAB1 polypeptide fused to another peptide or polypeptide said TAB1 polypeptide being bound to the TAK1 polypeptide or the TAK1 polypeptide fused to another peptide or polypeptide, by a primary antibody against the other peptide or polypeptide and a secondary antibody against the primary antibody. Preferably, the TAK1 polypeptide or the TAK1 polypeptide fused to another peptide or polypeptide is a TAK1 polypeptide or the TAK1 polypeptide fused to another peptide or polypeptide, that has been bound to a support. A preferred support is beads or a plate. Preferably, the secondary antibody is a secondary antibody that is labeled with a radioisotope, an enzyme a fluorescent substance. In another preferred embodiment, the contact between a TAK1 polypeptide, a TAB1 polypeptide and a test sample is carried out in a homogeneous system.

The present invention also provides (22) a screening method described in the above (20) and (21), which method comprises using a TAB1 polypeptide having an amino acid sequence comprising Met at amino acid position 1 to Pro at amino acid position 504 of the amino acid sequence as set forth in SEQ ID NO: 2 or having an amino acid sequence modified by the substitution, deletion and/or addition of one or a plurality of amino acid residues of the amino acid sequence as set forth in SEQ ID NO: 2 and maintaining the biological activity of the TAB1 polypeptide; and/or a TAK1 polypeptide having an amino acid sequence comprising Met at amino acid position 1 to Ser at amino acid position 579 of the amino acid sequence as set forth in SEQ ID NO: 4 or having an amino acid sequence modified by the substitution, deletion and/or addition of one or a plurality of amino acid residues of the amino acid sequence as set forth in SEQ ID NO: 4 and maintaining the biological activity of the TAK1 polypeptide.

The present invention also provides a kit for conducting the screening method as set forth in any of the above (1) to (22).

The present invention also provides a substance that is obtainable by the screening method as set forth in any of the above (1) to (22).

The present invention also provides a substance that inhibits binding between a TAK1 polypeptide and a TAB1 polypeptide obtainable by the screening method as set forth in any of the above (1) to (22).

The present invention also provides an inhibitor of signal transduction of TGF-β, said inhibitor comprising a substance that inhibits binding between a TAK1 polypeptide and a TAB1 polypeptide, obtainable by the screening method as set forth in any of the above (1) to (22).

The present invention also provides an activator of signal transduction of TGF-β, said activator comprising a substance that inhibits binding between a TAK1 polypeptide and a TAB1 polypeptide, obtainable by the screening method as set forth in any of the above (1) to (22).

The present invention also provides a suppressor of the enhancement of extracellular matrix protein production, said suppressor comprising, as an active ingredient, a substance that inhibits binding between a TAK1 polypeptide and a TAB1 polypeptide, obtainable by the screening method as set forth in any of the above (1) to (22).

The present invention also provides an activator of the enhancement of extracellular matrix protein production, said activator comprising, as an active ingredient, a substance that inhibits binding between a TAK1 polypeptide and a TAB1 polypeptide, obtainable by the screening method as set forth in any of the above (1) to (22).

The present invention also provides a suppressor of the inhibition of cellular growth, said suppressor comprising, as an active ingredient, a substance that inhibits binding between a TAK1 polypeptide and a TAB1 polypeptide, obtainable by the screening method as set forth in any of the above (1) to (22).

The present invention also provides an activator of the inhibition of cellular growth, said activator comprising, as an active ingredient, a substance that inhibits binding between a TAK1 polypeptide and a TAB1 polypeptide, obtainable by the screening method as set forth in any of the above (1) to (22).

The present invention also provides a suppressor of monocyte migration, said suppressor comprising, as an active ingredient, a substance that inhibits binding between a TAK1 polypeptide and a TAB1 polypeptide, obtainable by the screening method as set forth in any of the above (1) to (22).

The present invention also provides an activator of monocyte migration, said activator comprising, as an active ingredient, a substance that inhibits binding between a TAK1 polypeptide and a TAB1 polypeptide, obtainable by the screening method as set forth in any of the above (1) to (22).

The present invention also provides a suppressor of the induction of a biologically active substance, said suppressor comprising, as an active ingredient, a substance that inhibits binding between a TAK1 polypeptide and a TAB1 polypeptide, obtainable by the screening method as set forth in any of the above (1) to (22).

The present invention also provides an activator of a biologically active substance, said activator comprising, as an active ingredient, a substance that inhibits binding between a TAK1 polypeptide and a TAB1 polypeptide, obtainable by the screening method as set forth in any of the above (1) to (22).

The present invention also provides a suppressor of an immunosuppressive action, said suppressor comprising, as an active ingredient, a substance that inhibits binding between a TAK1 polypeptide and a TAB1 polypeptide, obtainable by the screening method as set forth in any of the above (1) to (22).

The present invention also provides an activator of an immunosuppressive action, said activator comprising, as an active ingredient, a substance that inhibits binding between a TAK1 polypeptide and a TAB1 polypeptide, obtainable by the screening method as set forth in any of the above (1) to (22).

The present invention also provides a suppressor of the deposition of amyloid β protein, said suppressor comprising, as an active ingredient, a substance that inhibits binding between a TAK1 polypeptide and a TAB1 polypeptide, obtainable by the screening method as set forth in any of the above (1) to (22).

The present invention also provides an activator of the deposition of amyloid β protein, said activator comprising, as an active ingredient, a substance that inhibits binding between a TAK1 polypeptide and a TAB1 polypeptide, obtainable by the screening method as set forth in any of the above (1) to (22).

BRIEF EXPLANATION OF DRAWINGS

FIGS. 1A and 1B (SEQ ID NO: 9) is a diagram showing the construction of human TAB1-FLAG and human TAK1-6×His.

FIG. 11 (encompassed by positions 437–504 of SEQ ID NO: 2) is the activity in Miller Units of β-galactosidase of a yeast L40 that was transformed with an amino terminal-truncated TAB1 mutants (TAB1C45–TAB1C20) and the yeast 2-hybrid expression plasmid of TAK1. The measurement was conducted three times and the result is expressed in the mean+/−S.D. The values represent a ratio based on the β-galactosidase activity of the yeast L40 that was transformed with TAB1C68 and the yeast 2-hybrid expression plasmid of TAK1.

FIG. 14 (encompassed by positions 437–504 of SEQ ID NO: 2) shows the ability of the TAB1 deletion mutants (TAB1C68, TAB1C45, TAB1C40, TAB1C35, TAB1C30 and TAB1C25) to bind to and activate TAK1

EMBODIMENT FOR CARRYING OUT THE INVENTION

Figure 2:
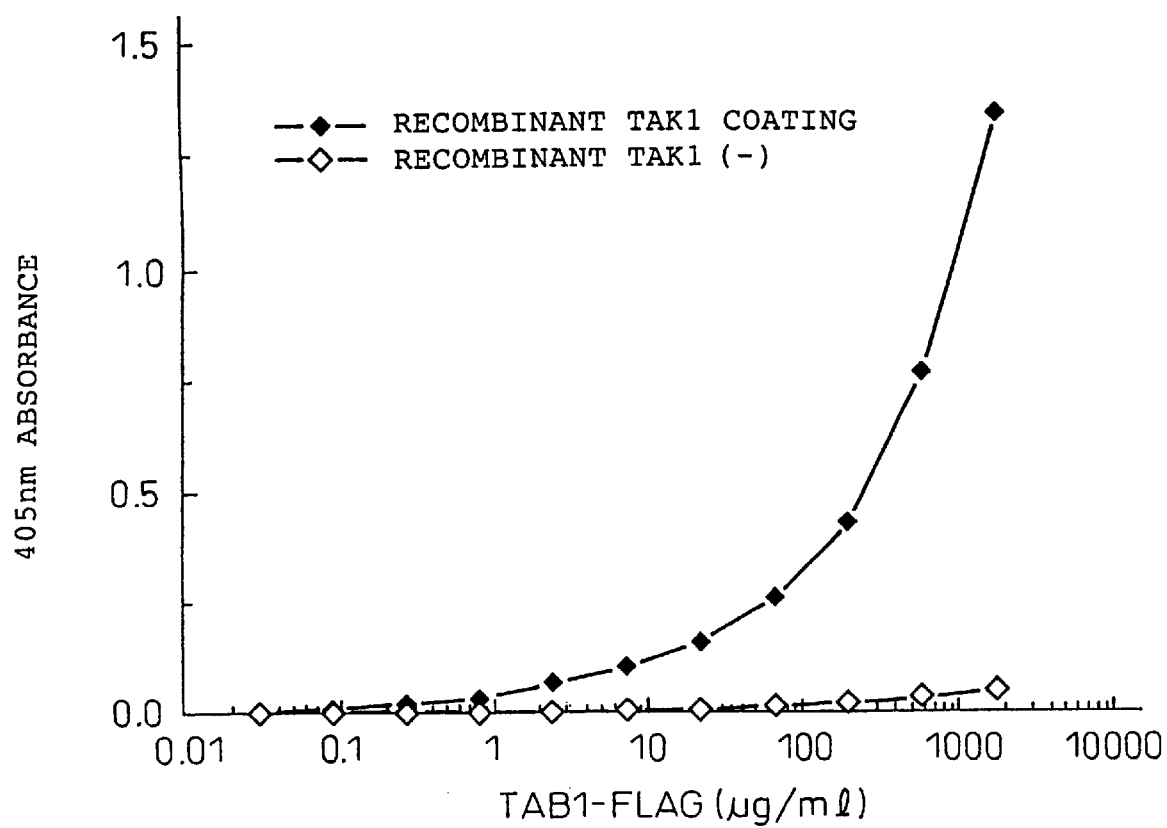
FIG. 2 is a graph showing binding between human TAK1-FLAG and human MBP-TAB1C-FLAG.

The TAB1 polypeptide for use in the present invention may be any TAB1 polypeptide, as long as it has an amino acid sequence comprising Met at amino acid position 1 to Pro at amino acid position 504 of the amino acid sequence as set forth in SEQ ID NO: 2 and the biological activity of the TAB1. It has been demonstrated that the biological activity of the TAB1 polypeptide is the activity of binding to and activating the TAK1 polypeptide.

More specifically, it has been demonstrated that the biological activity of the TAB1 polypeptide is the activity of binding to a region containing the catalytic domain of the TAK1 polypeptide having an amino acid sequence comprising an amino acid Met at position 1 to an amino acid Glu at position 303 of the TAK1 polypeptide and activating the kinase activity of the TAK1 polypeptide to the MAPKK. In the present invention, however, the TAB1 polypeptide is only required to have the activity of binding to the TAK1 polypeptide and may be a TAB1 polypeptide that has lost the activity of activating the TAK1 polypeptide. Accordingly, the biological activity of the TAB1 polypeptide as used herein may be the activity of binding to the TAK1 polypeptide.

The TAB1 polypeptide for use in the present invention may be a TAB1 polypeptide that has the biological activity of the TAB1 polypeptide and that has an amino acid sequence modified by the substitution, deletion and/or addition of one or a plurality of amino acid residues of the amino acid sequence as set forth in SEQ ID NO: 2. More specifically, the TAB1 polypeptide for use in the present invention may have an amino acid sequence in which one or more than one, preferably one or not greater than 20, and more preferably one or not greater than 10 amino acid residues are substituted in the amino acid sequence as set forth in SEQ ID NO: 2, as long as it has the biologically activity of the TAB1 polypeptide.

Alternatively, the amino acid sequence as set forth in SEQ ID NO: 2 may be modified by deletion of one or more than one, preferably one or not greater than 436, and more preferably one or not greater than 10 amino acid residues. The amino acid sequence as set forth in SEQ ID NO: 2 may also be modified by addition of one or more than one, preferably one or not greater than 30, and more preferably one or not greater than 20 amino acid residues. The TAB1 polypeptide for use in the present invention may also be modified by simultaneous substitution, deletion, and/or addition of the above amino acids.

It has been elucidated that the TAB1 polypeptide exhibits its biological activity as long as it has an amino acid sequence comprising amino acid Gln at position 437 to amino acid Pro at position 504 in SEQ ID NO: 2. Thus, the TAB1 polypeptide for use in the present invention may be a TAB1 polypeptide that has an amino acid sequence comprising amino acid Gln at position 437 to amino acid Pro at position 504 in SEQ ID NO: 2, or has an amino acid sequence modified by the substitution, deletion and/or addition of one or a plurality of amino acid residues in the amino acid sequence comprising amino acid Met at position 1 to amino acid Asn at position 436.

The TAB1 polypeptide may be a TAB1 polypeptide that has an amino acid sequence modified by the substitution, deletion and/or addition of one or a plurality of amino acid residues in the amino acid sequence comprising amino acid Gln at position 437 to amino acid Pro at position 504 in SEQ ID NO: 2, as long as it has the biological activity of the TAB1 polypeptide.

As a TAB1 polypeptide that has an amino acid sequence modified by the substitution, deletion and/or addition of one or a plurality of amino acid residues in the amino acid sequence as set forth in SEQ ID NO: 2, there can be mentioned a TAB1 polypeptide in which amino acid Ser at position 52 has been replaced with Arg and a TAB1 polypeptide that has an amino acid sequence comprising amino acid Gln at position 437 to amino acid Pro at position 504.

It is already known that a polypeptide that has an amino acid sequence modified by the substitution, deletion and/or addition of one or a plurality of amino acid residues of an amino acid sequence retains its biological activity (Mark, D. F. et al., Proc. Natl. Acad. Sci. U.S.A. (1984) 81, 5662–5666; zoller, M. J. & Smith, M. Nucleic Acids Research (1982) 10, 6487–6500; Wang, A. et al., Science 224, 1431–1433; Dalbadie-McFarland, G. et al., Proc. Natl. Acad. Sci. U.S.A. (1982) 79, 6409–6413).

The TAK1 polypeptide for use in the present invention may be any TAK1 polypeptide al long as it has an amino acid sequence comprising Met at amino acid position 1 to Ser at amino acid position 579 in the amino acid sequence as set forth in SEQ ID NO: 4 and the biological activity of TAK1. It has been demonstrated that the biological activity of the TAK1 polypeptide is the activity of binding to the TAB1 polypeptide and the kinase activity to MAPKK at an activated state.

More specifically, it has been demonstrated that it is the activity of activating the kinase activity of MAPKK by exhibiting the kinase activity at an activated state thereby phosphorylating MAPKK, for example MKK3 (Moriguchi, T. et al., J. Biol. Chem. (1996) 271, 13675–13679) and XMEK2/SEKI (Shibuya, H. et al., Science (1996) 272, 1179–1182). In the present invention, however, the TAK1 polypeptide is only required to have the activity of binding to the TAB1 polypeptide and may be a TAK1 polypeptide that has lost the kinase activity of the TAK1 polypeptide. Accordingly, the biological activity of the TAK1 polypeptide as used herein may be the activity of binding to the TAB1 polypeptide.

It has been elucidated that the TAK1 polypeptide exhibits its biological activity as long as it has an amino acid sequence comprising amino acid Met at position 1 to amino acid Gln at position 303 in SEQ ID NO: 4. Thus, the TAK1 polypeptide for use in the present invention may be a TAK1 polypeptide that has an amino acid sequence comprising amino acid Met at position 1 to amino acid Gln at position 303 in SEQ ID NO: 4, and an amino acid sequence modified by the substitution, deletion and/or addition of one or a plurality of amino acid residues in the amino acid sequence comprising amino acid Tyr at position 304 from amino acid Tyr to amino acid Ser at position 579. The TAK1 polypeptide may be a TAK1 polypeptide that has an amino acid sequence modified by the substitution, deletion and/or addition of one or a plurality of amino acid residues in the amino acid sequence comprising amino acid Met at position 1 to amino acid Gln at position 303, as long as it has the biological activity of the TAK1 polypeptide.

The TAK1 polypeptide is activated by the binding of the TAB1 polypeptide to a region containing a catalytic domain of a TAK1 polypeptide that has an amino acid sequence comprising amino acid Met at position 1 to amino acid Glu at position 303 of the TAK1 polypeptide as set forth in SEQ ID NO: 4. In accordance with the present invention, it has been disclosed that the TAK1 polypeptide binds to the TAB1 polypeptide at the amino acid sequence comprising amino acid Val at position 76 to amino acid Gln at position 303 of the TAK1 polypeptide as set forth in SEQ ID NO: 4. Although the TAK1 polypeptide that has an amino acid sequence comprising amino acid Val at position 76 to amino acid Gln at position 303 of the TAK1 polypeptide as set forth in SEQ ID NO: 4 did not exhibit any kinase activity, it has the activity of binding to the TAB1 polypeptide, and therefore it can be used in the present invention.

Thus, it may be a TAK1 polypeptide that has an amino acid sequence comprising amino acid Val at position 76 to amino acid Gln at position 303 in SEQ ID NO: 4 and an amino acid sequence modified by the substitution, deletion and/or addition of one or a plurality of amino acid residues in the amino acid sequence comprising amino acid Met at position 1 to amino acid Ile at position 75 and amino acid Tyr at position 304.

The TAK1 polypeptide may be a TAK1 polypeptide that has an amino acid sequence modified by the substitution, deletion and/or addition of one or a plurality of amino acid residues in the amino acid sequence comprising amino acid Val at position 76 to amino acid Gln at position 303 in SEQ ID NO: 4, as long as it has the activity of binding to the TAB1 polypeptide. The biological activity of the TAK1 polypeptide may also be activated by deleting at least 21 amino acid residues at the amino group-side terminal (N-terminal) of the TAK1 polypeptide.

The TAK1 polypeptide for use in the present invention may be a TAK1 polypeptide that has the biological activity of TAK1 polypeptide and an amino acid sequence modified by the substitution, deletion and/or addition of one or a plurality of amino acid residues in the amino acid sequence as set forth in SEQ ID NO: 4. More specifically, the TAK1 polypeptide for use in the present invention may have amino acids that are substituted with one or more than one, preferably one or not greater than 20, and more preferably one or not greater than 10 amino acid residues in the amino acid sequence as set forth in SEQ ID NO: 4, as long as it has the biologically activity of the TAK1 polypeptide.

Alternatively, the amino acid sequence as set forth in SEQ ID NO: 4 may have amino acids in which one or more than one, preferably one or not greater than 276, and more preferably one or not greater than 10 amino acid residues are deleted. Or, the amino acid sequence as set forth in SEQ ID NO: 4 may have amino acids in which one or more than one, preferably one or not greater than 30, and more preferably one or not greater than 20 amino acid residues are added.

As a TAK1 polypeptide that has an amino acid sequence modified by the substitution, deletion and/or addition of one or a plurality of amino acid residues in the amino acid sequence as set forth in SEQ ID NO: 4, there can be mentioned a TAK1 polypeptide of a mouse origin in which amino acid Gly at position 16 is replaced with Ser, amino acid His at position 372 is replaced with Arg, amino acid Ala at position 400 is replaced with Val, amino acid Thr at position 403 is replaced with Ala, and amino acid Thr at position 449 is replaced with Ala.

It is already known that a polypeptide that has an amino acid sequence modified by the substitution, deletion and/or addition of one or a plurality of amino acid residues of an amino acid sequence retains its biological activity (Mark, D. F. et al., Proc. Natl. Acad. Sci. U.S.A. (1984) 81, 5662–5666; Zoller, M. J. & Smith, M. Nucleic Acids Research (1982) 10, 6487–6500; Wang, A. et al., Science 224, 1431–1433; Dalbadie-McFarland, G. et al., Proc. Natl. Acad. Sci. U.S.A. (1982) 79, 6409–6413).

The polypeptides for use in the present invention differ in the amino acid sequence, molecular weight, isoelectric point, the presence or absence of an added sugar chain, the position of an added sugar chain, the structure of a sugar chain, the state of phosphorylation, and/or the presence or absence of a disulfide bond depending on the species from which they are derived, the host that produces them, and/or the method of purification. However, polypeptides having any structure may be used as long as they can be suitably used in the present invention. Preferably, the species from which the polypeptide is derived is human.

AS DNA encoding the TAB1 polypeptide for use in the present invention, there may be mentioned a nucleotide sequence comprising base A at nucleotide position 30 to nucleotide G at position 1541 of the nucleotide sequence as set forth in SEQ ID NO: 1. Furthermore, DNA encoding the TAB1 polypeptide for use in the present invention can be of any origin as long as it has the base sequence as set forth in SEQ ID NO: 1. Such DNA includes, for example, genomic DNA, cDNA, and synthetic DNA. They may be DNA obtained from a cDNA library and a genomic library obtained from various cells, tissues, or organs, or from species other than humans, and they may be a commercially available DNA library. Vectors for use in such libraries may be plasmids, bacteriophages, YAC vectors, and the like.

DNA encoding the TAB1 polypeptide for use in the present invention may be DNA that hybridizes to the nucleotide sequence as set forth in SEQ ID NO: 1 and encodes a polypeptide having the biological activity of TAB1. As a condition under which DNA encoding the TAB1 polypeptide hybridizes, there may be mentioned a stringent condition.

Such conditions include, for example, a low stringent condition. By way of example, a low stringent condition is a washing condition provided at room temperature in 2×SSC and 0.1% sodium dodecyl sulfate. More preferably, there may be mentioned a high stringent condition. By way of example, a high stringent condition is a washing condition provided at 60° C in 0.1×SSC and 0.1% sodium dodecyl sulfate. It is already known that a polypeptide encoded by a DNA that hybridizes under a suitable condition to a base sequence encoding a polypeptide has the same biological activity as the polypeptide.

*E. coli* that has the plasmid TAB1-f-4 containing DNA encoding the human TAB1 polypeptide having an amino acid sequence comprising amino acid Met at amino acid position 1 to amino acid Pro at amino acid position 504 of the amino acid sequence as set forth in SEQ ID NO: 2 was designated as *Escherichia coli* DH5α (TAB1-f-4) and has been internationally deposited under the provisions of the Budapest Treaty on Jul. 19, 1996, with the National Institute of Bioscience and Human Technology, Agency of Industrial Science and Technology, of 1–3, Higashi 1-chome, Tsukuba-shi, Ibaraki, Japan, as the accession number FERM BP-5599.

*E. coli* that has the plasmid pBS-TAB1 containing DNA encoding the above human TAB1 polypeptide that comprises amino acid Met at amino acid position 1 to amino acid Pro at amino acid position 504 of the amino acid sequence as set forth in SEQ ID NO: 2 and in which amino acid Ser at position 52 has been replaced with Arg was designated as *Escherichia coli* HB101 (pBS-TAB1) and has been internationally deposited under the provisions of the Budapest Treaty on Apr. 19, 1996, with the National Institute of Bioscience and Human Technology, Agency of Industrial Science and Technology, of 1–3, Higashi 1-chome, Tsukuba-shi, Ibaraki, Japan, as the accession number FERM BP-5508.

As DNA encoding the TAK1 polypeptide for use in the present invention, there may be mentioned a nucleotide sequence comprising nucleotide A at nucleotide position 183 to nucleotide G at position 1919 of the nucleotide sequence as set forth in SEQ ID NO: 2. Furthermore, DNA encoding the TAK1 polypeptide for use in the present invention can be of any origin as long as it has the nucleotide sequence as set forth in SEQ ID NO: 3. Such a DNA includes, for example, genomic DNA, cDNA, and synthetic DNA.

They may be DNA obtained from a cDNA library and a genomic library obtained from various cells, tissues, or organs, or from species other than human, and they may be a commercially available DNA library. Vectors for use in such libraries may be plasmids, bacteriophages, YAC vectors, and the like.

DNA encoding the TAK1 polypeptide for use in the present invention may be DNA that hybridizes to the nucleotide sequence as set forth in SEQ ID NO: 3 and encodes a polypeptide having the biological activity of TAK1. As a condition under which the DNA encoding the TAB1 polypeptide hybridizes, there may be mentioned a stringent condition.

Such conditions include, for example, a low stringent condition. By way of example, a low stringent condition is a washing condition provided at room temperature in 2×SSC and 0.1% sodium dodecyl sulfate. More preferably, there may be mentioned a high stringent condition. By way of example, a high stringent condition is a washing condition provided at 60° C in 0.1×SSC and 0.1% sodium dodecyl sulfate. It is already known that a polypeptide encoded by a DNA that hybridizes under a suitable condition to a nucleotide sequence encoding a polypeptide has the same biological activity as the polypeptide.

*E. coli* that has the plasmid pEF-TAK1 containing DNA encoding the above mouse TAK1 polypeptide was designated as *Escherichia coli* MC1061/P3 (pEF-TAK1) and has been internationally deposited under the provisions of the Budapest Treaty on Sep. 28, 1995, with the National Institute of Bioscience and Human Technology, Agency of Industrial Science and Technology, of 1–3, Higashi 1-chome, Tsukuba-shi, Ibaraki, Japan, as the accession number FERM BP-5246.

*E. coli* that has the plasmid pEF-TAK1DN containing DNA encoding the mouse TAK1 polypeptide that has a deletion of 21 amino acids at the N-terminal was designated as *Escherichia coli* MC1061/P3 (pEF-TAK1DN) and has been internationally deposited under the provisions of the Budapest Treaty on Sep. 28, 1995, with the National Institute of Bioscience and Human Technology, Agency of Industrial Science and Technology, of 1–3, Higashi 1-chome, Tsukuba-shi, Ibaraki, Japan, as the accession number FERM BP-5245.

*E. coli* that has the plasmid phTAK1 containing DNA encoding the human TAK1 polypeptide that has an amino acid sequence comprising amino acid Met at amino acid position 1 to amino acid Ser at amino acid position 579 of the amino acid sequence as set forth in SEQ ID NO: 4 and was designated as *Escherichia coli* JM109 (phTAK1) and has been internationally deposited under the provisions of the Budapest Treaty on Jul. 19, 1996, with the National Institute of Bioscience and Human Technology, Agency of Industrial Science and Technology, of 1–3, Higashi 1-chome, Tsukuba-shi, Ibaraki, Japan, as the accession number FERM BP-5598.

Polypeptides for use in the present invention may be the above polypeptides that are fused to another peptide or polypeptide. Such fusion polypeptides may be produced by a known method. Another peptide or polypeptide subjected to fusion with the polypeptide may be any peptide or polypeptide as long as it can be advantageously used in the present invention. As such peptides, for example, known peptides may be used including FLAG (Hopp, T. P. et al., BioTechnology (1988) 6, 1204–1210), 6×His comprising 6 His (histidine) residues, 10×His, influenza hemaglutinin (HA), fragments of human c-myc, fragments of VSV-GP, fragments of p18HIV, T7-tag, HSV-tag, E-tag, fragments of SV40T antigen, lck tag, fragments of a-tubulin, B-tag, fragments of Protein C, and the like.

As polypeptides, there may be mentioned, for example, GST (glutathione S-transferase), HA, the constant regions of immunoglobulin, β-galactosidase, MBP (maltose-binding protein), and the like. They may be commercially available polypeptides.

DNA encoding the polypeptide for use in the present invention may be generated by constructing the above-mentioned DNA using commercially available kits or by known methods. There may be mentioned, for example, digestion with a restriction enzyme, addition of a linker, insertion of an initiation codon (ATG) and/or a stop codon (ATT, TGA or TAG), and the like.

Expression vectors for use in the present invention may be any expression vectors as long as they can be suitably used in the present invention. As expression vectors, there may be mentioned expression vectors derived from a mammal such as pEF and pCDM8, expression vectors derived from an insect such as pBacPAK8, expression vectors derived from a plant such as pMH1 and pMH2, expression vectors derived from an animal virus such as PHSV and pMV, expression vectors derived from a yeast such as pNV11, expression vectors derived from *Bacillus subtilis* such as pPL608 and pKTH50 and expression vectors derived from *Escherichia coli* such as pGEX, PGEMEX and pMALp2.

Expression vectors of polypeptides for use in the present invention may be produced by linking DNA encoding the TAB1 polypeptide or the TAK1 polypeptide downstream to the promoter. As promoters/enhancers, promoters/enhancers derived from a mammal such as the EF1-α promoter/enhancer and γ-actin promoter/enhancer, promoters/enhancers derived from an insect such as polyhedrin virus promoter/enhancer, promoters/enhancers derived from a plant such as tabacco mosaic virus promoter/enhancer, promoters/enhancers derived from a plant such as SV40 promoter/enhancer and human CMV promoter/enhancer, promoters/enhancers derived from yeast such as alcohol dehydrogenase promoter/enhancer, promoters/enhancers derived from *Escherichia coli* such as Lac promoter/enhancer, Trp promoter/enhancer and Tac Promoter/enhancer.

For the expression of polypeptide for use in the present invention, a signal sequence suitable for the host to be used in the expression may be added. As the signal sequence, there may be mentioned a signal sequence for secretary proteins. As a signal sequence for secretary proteins, there may be mentioned a signal sequence for secretary proteins derived from a mammal such as a signal sequence for immunoglobulins. As a signal sequence for secretary proteins, there may be mentioned a signal sequence for secretary proteins derived from *E. coli* such as periplasm secretary signal sequence such as OmpA and the like.

An expression vector produced as mentioned above can be introduced into a host by a known method. Methods for introduction into the host includes, for example, electropolation, the calcium phosphate method, and the liposome method.

Polypeptides for use in the present invention can be obtained as recombinant polypeptides produced using gene recombinant technology as described above. For example, recombinant polypeptides may be produced by cloning the base sequence of a gene described herein from a cell, tissue, or an organ that expresses the polypeptide and integrating the gene into a suitable vector, which is introduced into a host to allow the host to produce said polypeptide. The recombinant polypeptides can be used in the present invention.

Specifically, mRNA encoding the gene can be isolated from the cell, tissue, or organ that expresses polypeptides to be used in the present invention. The isolation of mRNA is conducted by preparing total RNA using a known method such as the guanidine ultracentrifugation method (Chirgwin, J. M. et al., Biochemistry (1979) 18, 5294–5299), the AGPC method (Chomzynski, P. and Sacci, N., Anal. Biochem. (1987) 162, 156–159), and then purifying mRNA from the total RNA using the mRNA Purification Kit (Pharmacia) and the like. Alternatively, mRNA can be prepared directly using the QuickPrep mRNA Purification kit (Pharmacia).

The mRNA obtained is used to synthesize the cDNA of the gene using a reverse transcriptase. The synthesis of cDNA can be effected using the AMV Reverse Transcriptase First-strand cDNA Synthesis Kit (Seikagaku Kogyo), and the like. Alternatively, for the synthesis and amplification of cDNA, the Marathon cDNA Amplification kit (manufactured by CLONTECH) and the 5'-RACE method (Frohman, M. A. et al., Proc. Natl. Acad. Sci. U.S.A. (1988) 85, 8998–9002; Belyavsky, A. et al., Nucleic Acids Res. (1989) 17, 2919–2932) that employs the polymerase chain reaction (PCR) may be used.

A DNA fragment of interest may be prepared from the PCR product thus obtained and ligated to a vector DNA. Furthermore, a recombinant vector is constructed from this and is then introduced into *E. coli* for selection of colonies to prepare the desired recombinant vector. The nucleotide sequence of the desired DNA may be confirmed by a known method such as the dideoxy nucleotide chain termination method. Once the desired DNA has been obtained, it may be integrated into an expression vector.

More specifically, the DNA constructed as described above may be expressed to obtain polypeptides. When mammalian cells are used, expression may be accomplished using a vector containing a commonly used useful promoter/enhancer, the gene to be expressed, and DNA in which the poly A signal has been operably linked at 3' downstream thereof or a vector containing said DNA. Examples of the promoter/enhancer include the human cytomegalovirus immediate early promoter/enhancer.

Additionally, as the promoter/enhancer which can be used for expression thereof, there are viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when the SV40 promoter/enhancer is used, or by the method of Mizushima et al. (Nucleic Acids Res. (1990) 18, 5322) when the HEF1α promoter/enhancer is used.

In the case of *E. coli*, expression may be conducted by operably linking a commonly used useful promoter, a signal sequence for polypeptide secretion, and the gene to be expressed, followed by expression thereof. As the promoter, for example, there can be mentioned the lacz promoter and the araB promoter. The method of Ward et al. (Nature (1098) 341, 544–546; FASEB J. (1992) 6, 2422–2427) may be used when the lacz promoter is used, and the method of Better et al. (Science (1988) 240, 1041–1043) may be used when the araB promoter is used.

As a signal sequence for polypeptide secretion, when produced in the periplasm of E. coli, the pelB signal sequence (Lei, S. P. et al., J. Bacteriol. (1987) 169, 4379) can be used.

As a origin of replication, there can be used those derived from SV40, polyoma virus, adenovirus, bovine papilloma virus (BPV) and the like. Furthermore, for the amplification of gene copy number in the host cell system, expression vectors can include as selectable markers the aminoglycoside transferase (APH) gene, the thymidine kinase (TK) gene, E. coli xanthine guaninephosphoribosyl transferase (Ecogpt) gene, the dihydrofolate reductase (dhfr) gene and the like.

For the production of polypeptides for use in the present invention, any production system can be used. The production system of polypeptide preparation comprises the in vitro or the in vivo production system. As the in vitro production system, there can be mentioned a production system which employs eukaryotic cells and the production system which employs prokaryotic cells.

When the eukaryotic cells are used, there are the production systems which employ the animal cells, the plant cells, and the fungal cells. Known animal cells include (1) mammalian cells such as CHO cells (J. Exp. Med. (1995) 108, 945), COS cells, myeloma cells, baby hamster kidney (BHK) cells, HeLa cells, and Vero cells, (2) amphibian cells such as *Xenopus oocytes* (Valle, et al., Nature (1981) 291, 358–340), or (3) insect cells such as sf9, sf21, and Tn5. As the CHO cells, dhfr-CHO (Proc. Natl. Acad. Sci. U.S.A. (1968) 77, 4216–4220), a CHO cell that is deficient in the DHFR gene, and CHO K-1 (Proc. Natl. Acad. Sci. U.S.A. (1968) 60, 1275) can be preferably used.

Known plant cells include, for example, those derived from *Nicotiana tabacum*, which is subjected to callus culture. Known fungal cells include yeasts such as the genus Saccharomyces, more specifically *Saccharomyces cereviceae*, or filamentous fungi such as the genus Aspergillus, more specifically *Aspergillus niger.*

When the prokaryotic cells are used, there are the production systems which employ bacterial cells. Known bacterial cells include *Escherichia coli* (E. coli), and *Bacillus subtilis.*

By transforming these cells with the desired DNA and culturing the transformed cells in vitro, polypeptides can be obtained. Culturing is conducted in the known methods. For example, as the culture liquid, DMEM, MEM, RPMI1640, and IMDM can be used, and serum supplements such as fetal calf serum (FCS) may be used in combination, or serum-free medium can be used. pH during the culture is preferably about 6 to 8. Culture is usually carried out at 30 to 40° C. for about 15 to 200 hours with, as desired, medium changes, aeration, and agitation.

As in vivo production systems, there can be mentioned those which employ animals and those which employ plants. DNA of interest is introduced into these animals or plants, and the polypeptides are produced in such animals or plants, and recovered.

When animals are used, there are the production systems which employ mammals and insects.

As mammals, goat, pigs, sheep, mice, and cattle can be used (Vicki Glaser, SPECTRUM Biotechnology Applications, 1993). When mammals are used, transgenic animals can be used.

For example, a DNA of interest is inserted into the middle of the gene encoding protein which is inherently produced in the milk such as goat β casein to prepare fusion genes. DNA fragments containing the fusion gene into which the DNA has been inserted are injected into a goat embryo, and the embryo is introduced into a female goat. The polypeptide is obtained from the milk produced by the transgenic goat born to the goat who received the embryo or offsprings thereof. In order to increase the amount of milk containing the polypeptide produced by the transgenic goat, hormones may be given to the transgenic goat as appropriate. (Ebert, K. M. et al., Bio/Technology (1994) 12, 699–702).

As an insect, silkworms may be used. When silkworms are used, baculovirus into which the DNA of interest has been inserted is infected to the silkworm, and the desired polypeptide can be obtained from the body fluid of the silkworm (Susumu, M. et al., Nature (1985) 315, 592–594).

Moreover, when plants are used, tabacco, for example, can be used. When tabacco is used, the DNA of interest is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired polypeptide from the leaves of the tabacco (Julian, K. -C. Ma et al., Eur. J. Immunol. (1994) 24, 131–138).

As methods of introducing an expression vector into a host, there can be used a known method such as the calcium phosphate method (Virolgoy (1973) 52, 456–467), the electropolation method (EMBO J. (1982) 1, 841–845), and the like. Considering the frequency of use of the host's codon for use in the present invention, a sequence having a better efficiency of expression can be designed (Grantham, R. et al., Nucleic Acids Research (1981) 9, r43–r74).

Gene is introduced as described above into these animals or plants, and polypeptides are produced in the body of the animals or the plants and recovered. Polypeptides expressed and produced as described above can be separated from the inside or outside of the host cell and then may be purified to homogeneity. Separation and purification of the antibody for use in the present invention may be accomplished by, but not limited to, the separation and the purification methods conventionally used for protein purification.

Polypeptides can be separated and purified by selecting and combining, as appropriate, methods including, but not limited to, chromatography columns such as affinity chromatography, filtration, ultrafiltration, salting-out, dialysis, SDS-polyacrylamide gel electrophoresis, isoelectric focusing, and the like (Antibodies: A Laboratory Manual, Ed Harlow and David Lane, Cold Spring Harbor Laboratory, 1988).

As chromatography, there may be mentioned, for example, affinity chromatography, ion exchange chromatography, hydrophobic chromatography, gel-filtration, reverse phase chromatography, adsorption chromatography, and the like (Strategies for Protein Purification and Characterization: A Laboratory Course Manual. Ed Daniel R. Marshak et al., Cold Spring Harbor Laboratory Press, 1986). These chromatographies can be carried out using a liquid chromatography such as HPLC and FPLC.

Polypeptides can be determined using a known method. For example, measurement of absorbance or the Bradford method can be used.

The present invention provides a method for screening substances that inhibit binding between a TAK1 polypeptide and a TAB1 polypeptide, which method comprises contacting the TAB1 polypeptide to the TAK1 polypeptide and a test sample, and then detecting or determining the TAK1 polypeptide that is bound to the TAB1 polypeptide; or a method for screening substances that inhibit binding between a TAK1 polypeptide and a TAB1 polypeptide, which method comprises contacting the TAK1 polypeptide to the TAB1 polypeptide and a test sample and then detecting or determining the TAB1 polypeptide that is bound to the TAK1 polypeptide.

The screening system for use in the present invention may be conducted as an in vitro assay system.

The in vitro assay system may be conducted in a non-cellular system. Specifically, one of the TAB1 polypeptide and the TAK1 polypeptide may be previously bound to a support, to which polypeptide are then added the other polypeptide and the test sample, incubated and then washed followed by detection or determination of binding of the polypeptide to the other polypeptide bound to the support. Alternatively, the test sample may be added under a homogeneous condition without binding any of the TAB1 polypeptide and the TAK1 polypeptide to the support, incubated, and then immunoprecipitated using antibody to either of the TAB1 polypeptide and the TAK1 polypeptide followed by detection or determination of the amount of the conjugate.

The TAB1 polypeptide or the TAK1 polypeptide may be a polypeptide produced by cells that inherently express them, cells into which DNA encoding a polypeptide for use in the present invention has been introduced, or animals or plants into which DNA encoding a polypeptide for use in the present invention has been introduced, which may be used in a purified or crude-purified form.

One of the purified or semi-purified TAB1 polypeptide or the TAK1 polypeptide is allowed to bind to the support. The polypeptide may be immobilized onto the support by a standard method in biding the polypeptides to a support. As supports to which polypeptides are bound, there may be mentioned, for example, insoluble polysaccharides such as agarose, dextran, cellulose, synthetic resin such as polystyrene, polyacrylamide and silicone. More specifically, commercially available beads or plates that are produced using the above as a raw material are used. In the case of beads, there may be used columns that are packed with them. In the case of plates, there may be mentioned multiwell plates (96-well multiwell plates, etc.) or biosensor chips.

Binding between polypeptides and supports may be effected using conventionally known methods such as chemical bonding, and physical adsorption. Alternatively, it is be possible to bind an antibody that specifically recognizes the polypeptide to a support in advance so that the antibody and the polypeptide become joined. Furthermore, avidin/biotin can also be bound.

The binding between the TAB1 polypeptide and the TAK1 polypeptide may be usually effected in buffer solutions. As buffer solutions, for example, phosphate buffers, Tris buffers and the like may be used. Incubation conditions may be any conditions that are conventionally used, including the incubation at 4° C. to room temperature for 1 hour to 24 hours. Washing after the incubation may be effected in any solution that does not prevent binding between the TAB1 polypeptide and the TAK1 polypeptide including, for example, a buffer solution containing a surfactant. As surfactants, 0.05% Tween 20 may be used.

Test specimens to be screened according to the present invention include, for example, peptides, polypeptides, synthetic compounds, microbial fermentation products, marine organism extracts, plant extracts, prokaryotic cell extracts, eukaryotic unicellular extracts, or animal cell extracts, or libraries thereof. Substances included in these test specimens are ones that are expected to act in an inhibitory manner on binding between the TAK1 polypeptide and the TAB1 polypeptide. These inhibiting substances inhibit the binding of the TAK1 polypeptide to the TAB1 polypeptide and the binding of the TAB1 polypeptide to the TAK1 polypeptide.

In order to select substances contained in these test specimens that inhibit the binding of the TAK1 polypeptide to the TAB1 polypeptide and the binding of the TAB1 polypeptide to the TAK1 polypeptide, they are incubated and washed under an appropriated condition to separate the specific binding from the non-specific binding. Then the status of binding of the polypeptides for use in the present invention can be evaluated.

In the screening method of the present invention, the control group can be set up together with the group in which the test specimens are contacted to the polypeptides. As the control group, the negative control group having no test specimens, the positive control group having a substance that clearly inhibits binding between the TAB1 polypeptide and the TAK1 polypeptide, or both of the groups can be set up.

When the bound polypeptide is detected or determined in accordance with the present invention, the bound polypeptide can only be detected, or the bound polypeptide may be determined in a quantitative manner. In these cases, the result obtained for the negative control group having no test specimens, the result obtained for the group having a test specimen, and/or the result obtained for the positive control group having a substance that clearly inhibits binding between the TAB1 polypeptide and the TAK1 polypeptide can be compared to detect a substance that inhibits binding between the TAB1 polypeptide and the TAK1 polypeptide of interest.

Alternatively, these results may be obtained in numerical values, which values may be compared to determine quantitatively the activity of the substance that inhibits binding between the TAB1 polypeptide and the TAK1 polypeptide of interest. When quantitative determinations are made, the numerical value obtained with the negative control group having no test specimens and those obtained with the group in which a test specimen was applied may be compared to detect the substance that inhibits binding between the TAB1 polypeptide and the TAK1 polypeptide of interest. The presence of a substance that inhibits binding between the TAB1 polypeptide and the TAK1 polypeptide of interest in the test specimen would decrease the bound polypeptide, thereby enabling to determine the specimen that contains the binding-inhibiting substance.

When quantitative determinations are also made, quantitation may be made based on a standard curve generated from the numerical values obtained with the positive control group containing known amounts of the substance that clearly inhibits binding between the TAB1 polypeptide and the TAK1 polypeptide. When the amount of the bound polypeptide is large, the activity of the substance contained in the test specimen that inhibits binding between the TAB1 polypeptide and the TAK1 polypeptide is expected to be low, whereas when the amount of the bound polypeptide is small, the activity of the substance contained in the test specimen that inhibits binding between the TAB1 polypeptide and the TAK1 polypeptide is expected to be high.

In a screening method of a substance that inhibits binding between the TAB1 polypeptide and the TAK1 polypeptide, biosensors may be used that utilize a surface plasmon resonance phenomenon as a means to detect or determine the bound polypeptide. Biosensors that utilize a surface plasmon resonance phenomenon permit a real time observation of protein-protein interaction as a surface plasmon resonance signal using and without labeling a trace amount of protein (for example BIAcore; manufactured by Pharmacia). Thus, by using biosensors such as BIAcore, binding between the TAB1 polypeptide and the TAK1 polypeptide can be evaluated.

Accordingly, it is intended to contact the TAB1 polypeptide or the TAK1 polypeptide to a sensor chip on which is immobilized the TAK1 polypeptide or the TAB1 polypeptide and then to detect as resonance signals the TAB1 polypeptide or the TAK1 polypeptide that are bound to the TAK1 polypeptide or the TAB1 polypeptide.

Specifically it may be carried out as follows. First a sensor chip CM5 (Biosensor) is activated and then the TAK1 polypeptide or the TAB1 polypeptide is immobilized thereon. Thus, after the sensor chip is activated with an aqueous solution of EDC/NHS (200 mM EDC (N-ethyl-N'-(3-dimethylaminopropyl)carbonate, hydrochloride), 50 mM NHS (N-hydroxysuccinimide)), it is washed with an HBS buffer (10 mM HEPES, pH 7.4, 150 mM NaCl, 3.4 mM EDTA, 0.05% Tween 20).

Then an appropriate amount of TAK1 polypeptide or TAB1 polypeptide dissolved in the HBS buffer is contacted to the sensor chip and immobilized thereon. After washing the sensor chip with the HBS buffer, the active groups remaining on the sensor chip are blocked with an ethanolamine solution (1M ethanolamine hydrochloride, pH 8.5). The sensor chip is washed again with the HBS buffer for use in the binding evaluation.

Then an appropriate amount of TAB1 polypeptide or TAK1 polypeptide dissolved in the HBS buffer is injected, whereupon the amount of the TAB1 polypeptide or the TAK1 polypeptide that is bound to the TAK1 polypeptide or the TAB1 polypeptide immobilized on the sensor chip is observed as an increment in the value of resonance signal.

In the above binding-evaluation system, furthermore, a test specimen is injected after the TAB1 polypeptide or the TAK1 polypeptide. Alternatively, control groups may be set up together with the injection of the test specimen. As the control groups, the negative control group having no test specimens, the positive control group having a substance that clearly inhibits binding between the TAB1polypeptide and the TAK1 polypeptide, or both of the groups, can be set up.

The bound polypeptide is quantitatively determined as a change in the value of resonance signal. In these cases, the result obtained for the negative control group having no test specimens, the result obtained for the group having a test specimen, and/or the result obtained for the positive control group having a substance that clearly inhibits binding between the TAB1 polypeptide and the TAK1 polypeptide can be compared to detect and determine a substance that inhibits binding between the TAB1 polypeptide and the TAK1 polypeptide of interest.

As a means of detecting or determining the bound polypeptide in the method of screening substances that inhibit binding between the TAK1 polypeptide and the TAB1 polypeptide of the present invention, either of the polypeptides is labeled and the label of the bound polypeptide can be detected or determined.

For example, in the above screening method, one polypeptide that is to be contacted to the other polypeptide together with the test specimen is labeled beforehand and incubated with the test specimen, washed, and then the bound polypeptide is detected or determined by means of the label. Thus, preferably to one polypeptide that has been bound to a support are contacted the test specimen and the other labeled polypeptide. After incubating and washing, the label of the bound polypeptide can be detected or determined.

The TAK1 polypeptide or the TAB1 polypeptide can be labeled by commonly known methods. As labels, there may be used, for example, radioisotopes, enzymes, fluorescent substances, biotin/avidin, and the like. These labels may be commercially available ones. As radioisotopes, there may be mentioned, for example, $^{32}P$, $^{33}P$, $^{131}I$, $^{125}I$, $^{3}H$, $^{14}C$, and $^{35}S$. As enzymes, there may be mentioned, for example, alkaline phosphatase, horseradish peroxidase, β-galactosidase, β-glucosidase, and the like. As fluorescent substances, there may be mentioned, for example, fluorescein isocyanate (FITC) and rhodamine. These are commercially available and may be labeled by known methods.

Specifically, the following procedure may be used. Thus, a solution containing one polypeptide is added to a plate, which is then allowed to stand overnight. After washing the plate, it is blocked with, for example, BSA to prevent non-specific binding of polypeptides. The plate is washed again, and a test specimen and the other polypeptide that has been labeled are added to the plate. At the same time, a group (the negative control) containing no test specimens and/or a group (the positive control) to which a known concentration of a binding-inhibiting substance has been added are set up and incubated. After incubation, the washed and bound polypeptide is detected or determined. For the detection or determination, in the case of a radioisotope, liquid scintillation is used.

In the case of an enzyme, a substrate therefor is added and the enzymatic changes, for example color development of the substrate, are detected or determined. Comparison of these results with the numerical value obtained for the control group permits the identification of the test specimen containing the inhibiting substance.

As a means for detecting or determining the bound polypeptide in the method of screening substances that inhibit binding between the TAK1 polypeptide and the TAB1 polypeptide of the present invention, a primary antibody that specifically recognizes one polypeptide can be used.

For example, in the above screening method, to one polypeptide are contacted the other polypeptide together with the test specimen, incubated with the test specimen, washed, and then the bound polypeptide is detected or determined by means of a primary antibody that specifically recognizes the polypeptide. Thus, preferably to one polypeptide that has been bound to a support are contacted the test specimen and the other polypeptide. After incubating and washing, the bound polypeptide may be detected or determined by means of a primary antibody that specifically recognizes the polypeptide. Preferably, the primary antibody has been labeled with a label. The method of producing the antibody is described below.

The antibody can be labeled by commonly known methods. As labels, there may be used, for example, radioisotopes, enzymes, fluorescent substances, and the like. These labels may be commercially available ones. As radioisotopes, there may be mentioned, for example, $^{32}P$, $^{33}P$, $^{131}I$, $^{125}I$, $^{3}H$, $^{14}C$, and $^{35}S$. As enzymes, there may be mentioned, for example, alkaline phosphatase, horseradish peroxidase, β-galactosidase, β-glucosidase, and the like. As fluorescent substances, there may be mentioned, for example, fluorescein isocyanate (FITC) and rhodamine. These are commercially available and may be labeled in known methods.

Specifically, the following procedure may be used. Thus, a solution containing one polypeptide is added to a plate, which is then allowed to stand overnight. After washing the plate, it is blocked with, for example, BSA to prevent non-specific binding of polypeptides. The plate is washed again, and a test specimen and the other polypeptide are added to the plate. At the same time, a group (the negative control) containing no test specimens and/or a group (the positive control) to which a known concentration of a binding-inhibiting substance has been added are set up and incubated.

After incubation, the plate is washed and an antibody, against the polypeptide that was added together with the test specimen, is added. After an appropriate incubation, the plate is washed and the polypeptide is detected or determined by means of a primary antibody that specifically recognizes the polypeptide. For the detection or determination, in the case of a radioisotope, liquid scintillation is used. In the case of an enzyme, a substrate therefor is added and the enzymatic changes, for example color development of the substrate, are detected or determined by means of a photometer. In the case of a fluorescent substance, detection and determination may be effected by means of a fluorophotometer. Comparison of these results with the numerical value obtained for the control group permits the identification of the test specimen containing the inhibiting substance.

As a means of detecting or determining the bound polypeptide in the method of screening substances that inhibit binding between the TAK1 polypeptide and the TAB1 polypeptide of the present invention, a primary antibody that specifically recognizes the other peptide or polypeptide fused to the TAB1 polypeptide or the TAK1 polypeptide can be used.

For example, in the above screening method, to one polypeptide are contacted another polypeptide together with a test specimen, incubated with the test specimen, washed, and then the bound polypeptide is detected or determined by means of a primary antibody that specifically recognizes the other peptide or polypeptide fused to the polypeptide.

Thus, preferably to one polypeptide that has been bound to a support are contacted the test specimen and another polypeptide. After incubating and washing, the bound polypeptide may be detected or determined by means of a primary antibody that specifically recognizes the other peptide or polypeptide fused to the polypeptide. Preferably, the primary antibody has been labeled with a label. The method of producing the antibody is described below.

The antibody can be labeled by commonly known methods.

Specifically, the following procedure may be used. Thus, a solution containing one polypeptide is added to a plate, which is then allowed to stand overnight. After washing the plate, it is blocked with, for example, BSA to prevent non-specific binding of polypeptides. The plate is washed again, and a test specimen and a polypeptide fused to another peptide or polypeptide are added to the plate. At the same time, a group (the negative control) containing no test specimens and/or a group (the positive control) to which a known concentration of a binding-inhibiting substance has been added are set up and incubated.

After incubation, the plate is washed and an antibody against the other peptide or polypeptide fused to the polypeptide that was added together with the test specimen is added. After an appropriate incubation, the plate is washed and the polypeptide is detected or determined by means of a primary antibody that specifically recognizes the other polypeptide fused to the polypeptide. For the detection or determination, in the case of a radioisotope, liquid scintillation is used. In the case of an enzyme, a substrate therefor is added and the enzymatic changes, for example color development of the substrate, are detected or determined by means of a photometer. In the case of a fluorescent substance, detection and determination may be effected by means of a fluorophotometer. Comparison of these results with the numerical value obtained for the control group permits the identification of the test specimen containing the inhibiting substance.

As a means of detecting or determining the bound polypeptide in the method of screening substances that inhibit binding between the TAK1 polypeptide and the TAB1 polypeptide of the present invention, a primary antibody that specifically recognizes the TAB1 polypeptide or the TAK1 polypeptide and a secondary antibody that specifically recognizes the primary antibody can be used.

For example, in the above screening method, to one polypeptide are contacted another polypeptide together with a test specimen, incubated with the test specimen, washed, and then the bound polypeptide is detected or determined by means of a primary antibody that specifically recognizes the polypeptide and a secondary antibody that specifically recognizes the primary antibody.

Thus, preferably to one polypeptide that has been bound to a support are contacted a test specimen and another polypeptide. After incubating and washing, the bound polypeptide may be detected or determined by means of a primary antibody that specifically recognizes the polypeptide and a secondary antibody that specifically recognizes the primary antibody. Preferably, the secondary antibody has been labeled with a label.

The method of producing the antibody is described below.

The antibody can be labeled by commonly known methods.

Specifically, the following procedure may be used. Thus, a solution containing one polypeptide is added to a plate, which is then allowed to stand overnight. After washing the plate, it is blocked with, for example, BSA to prevent non-specific binding of polypeptides. The plate is washed again, and a test specimen and the polypeptide are added to the plate. At the same time, a group (the negative control) containing no test specimens and/or a group (the positive control) to which a known concentration of a binding-inhibiting substance has been added are set up and incubated.

After incubation, the plate is washed and a primary antibody against another peptide or polypeptide fused to the polypeptide that was added together with the test specimen is added. After an appropriate incubation, the plate is washed and the polypeptide is detected or determined by means of the secondary antibody that specifically recognizes the primary antibody that specifically recognizes the polypeptide. For the detection or determination, in the case of a radioisotope, liquid scintillation is used. In the case of an enzyme, a substrate therefor is added and the enzymatic changes, for example color development of the substrate, are detected or determined by means of a photometer. In the case of a fluorescent substance, detection and determination may be effected by means of a fluorophotometer. Comparison of these results with the numerical value obtained for the control group permits the identification of the test specimen containing the inhibiting substance.

As a means of detecting or determining the bound polypeptide in the method of screening substances that inhibit binding between the TAK1 polypeptide and the TAB1 polypeptide of the present invention, a primary antibody that specifically recognizes the other peptide or polypeptide fused to the TAB1 polypeptide or the TAK1 polypeptide and a secondary antibody that specifically recognizes the primary antibody can be used.

For example, in the above screening method, to one polypeptide are contacted another polypeptide together with a test specimen, incubated with the test specimen, washed, and then the bound polypeptide is detected or determined by means of a primary antibody that specifically recognizes the other peptide or polypeptide fused to the polypeptide and a secondary antibody that specifically recognizes the primary antibody. Thus, preferably, to one polypeptide that has been bound to a support are contacted the test specimen and the other polypeptide. After incubating and washing, the bound polypeptide may be detected or determined by means of a primary antibody that specifically recognizes the other peptide or polypeptide fused to the polypeptide and a secondary antibody that specifically recognizes the primary antibody. Preferably, the secondary antibody has been labeled with a label. The method of producing the antibody is described below.

The antibody can be labeled by commonly known methods.

Specifically, the following procedure may be used. Thus, a solution containing one polypeptide is added to a plate, which is then allowed to stand overnight. After washing the plate, it is blocked with, for example, BSA to prevent non-specific binding of polypeptides. The plate is washed again, and a test specimen and another polypeptide fused to the other peptide or polypeptide are added to the plate. At the same time, a group (the negative control) containing no test specimens and/or a group (the positive control) to which a known concentration of a binding-inhibiting substance has been added are set up and incubated.

After incubation, the plate is washed and a primary antibody against the other peptide or polypeptide fused to the polypeptide that was added together with the test specimen is added. After an appropriate incubation, the plate is washed and a secondary antibody that specifically recognizes the primary antibody is added. After an appropriate incubation, the plate is washed and the polypeptide is detected or determined by means of the secondary antibody that specifically recognizes the primary antibody that specifically recognizes the other polypeptide fused to the polypeptide. For the detection or determination, in the case of a radioisotope, liquid scintillation is used. In the case of an enzyme, a substrate therefor is added and the enzymatic changes, for example color development of the substrate, are detected or determined by means of a photometer. In the case of a fluorescent substance, detection and determination may be effected by means of a fluorophotometer. Comparison of these results with the numerical value obtained for the control group permits the identification of the test specimen containing the inhibiting substance.

More specifically, the present invention may be conducted by, most specifically, an ELISA (enzyme-linked immunosorbent assay). Thus, the TAK1 polypeptide fused to another peptide or polypeptide, for example 6×His, is diluted in an immobilization buffer (0.1 M $NaHCO_3$, 0.02% $NaN_3$, pH 9.6). A suitable amount of an aqueous solution that was diluted is added to each well of a 96-well immunoplate (manufactured by Nunc), which is then incubated overnight at 4° C.

After each well is washed three times with the wash buffer (prepared to 0.05% Tween 20 in PBS), 200 µl of a 5% solution of BSA (manufactured by SIGMA) dissolved in PBS is added to block overnight at 4° C.

Then, each well is washed three times with the wash buffer, and appropriate amounts of the TAB1 polypeptide fused to another peptide or polypeptide, for example FALG, and a test specimen are added thereto and incubated at room temperature for one hour. Each well is washed three times with the wash buffer, and 100 µl of mouse anti-FLAG M2 antibody (manufactured by IBI) dissolved to 3 mg/ml in a dilution buffer is added to each well and incubated at room temperature for one hour.

Each well is washed three times with a wash buffer, and 100 µl of alkaline phosphatase-labeled goat anti-mouse IgG antibody (manufactured by ZYMED) diluted 1000-fold in the dilution buffer is added to each well and incubated at room temperature for one hour. Each well is washed five times with the wash buffer, and 100 µl of the color development solution (substrate buffer; p-nitrophenyl phosphate dissolved to 1 mg/ml in 50 mM $NaHCO_3$, 10 mM $MgCl_2$, pH 9,8, manufactured by Sigma) is added to each well and incubated at room temperature. Subsequently, absorbance at 405 nm is measured using a microplate reader (Model 3550, manufactured by BIO-RAD). Comparison of these results with the numerical value obtained for the negative control group and/or positive control group permits the identification of the test specimen containing the inhibiting substance.

The screening method of the present invention may also be used for the High Throughput Screening (HTS). Specifically, steps up to the blocking may be conducted manually, and the subsequent reactions can be automated by robotization to realize High Throughput Screening.

Thus, the TAK1 polypeptide fused to another peptide or polypeptide, for example 6×His, is diluted in the immobilization buffer (0.1 M $NaHCO_3$, 0.02% $NaN_3$, pH 9.6). A suitable amount of the aqueous solution that was diluted to each well of a 96-well immunoplate (manufactured by Nunc) is added and then incubated overnight at 4° C.

After each well is washed three times with the wash buffer (prepared to 0.05% Tween 20 in PBS), 200 µl of a 5% solution of BSA (manufactured by SIGMA) dissolved in PBS is added to block overnight at 4° C.

Subsequently, an immunoplate after blocking is mounted to, for example, the Biomek 2000 HTS system (manufactured by Beckman) and the control program of the system is executed. At this time the delivery of the solution to each well of the immunoplate and the removal thereof can be carried out using the Biomek 2000 HTS system (manufactured by Beckman) and the Multipipette 96-well simultaneous dispenser (manufactured by Sagian) as a dispensing instrument. Washing of each well of the immunoplate can also be carried out using the EL404 microplate washer (Bio Tek). Measurement of absorbance can be made using the SPECTRAmax250 plate reader (manufactured by Molecular Devices).

The program is set so as to perform the following steps. Thus, each well is washed three times with the wash buffer, appropriate amounts of the test specimen and the other peptide or polypeptide diluted in the dilution buffer (1% BSA, 0.5% Tween 20, PBS) such as the TAB polypeptide fused to MBP (maltose-binding protein) are added. At the same time, a group (the negative control) containing no test specimens and a group (the positive control) to which a known concentration of a binding-inhibiting substance has been added are set up and incubated at room temperature for one hour.

Each well is washed three times with the wash buffer, 100 µl of rabbit anti-MBP antiserum (manufactured by New England Biolabs) is added to each well, and incubated at room temperature for one hour. Each well is washed three times with the wash buffer, 100 µl of alkaline phosphatase-labeled goat anti-mouse IgG antibody (manufactured by TAGO) diluted 5000-fold in the dilution buffer is added to each well, and incubated at room temperature for one hour.

Each well is then washed five times with the wash buffer, 100 µl of the color development solution (substrate buffer; p-nitrophenyl phosphate dissolved to 1 mg/ml in 50 mM $NaHCO_3$, 10 mM $MgCl_2$, pH 9,8, manufactured by Sigma) is added to each well, and incubated at room temperature. Subsequently, absorbance at 405 nm is measured using a microplate reader, the Biomek plate reader (manufactured by Beckman/Molecular Devices). Comparison of these results with the numerical value obtained for the control group permits the identification of the test specimen containing the inhibiting substance.

Antibodies for use in the present invention may be those that are commercially available or that are contained in commercially available kits, or they can be obtained as monoclonal or polyclonal antibodies using known methods.

Monoclonal antibodies can be obtained by using the desired sensitizing antigen, which is immunized in a conventional method for immunization, by fusing the immune cells thus obtained with known parent cells, and screening monoclonal antibody-producing cells using a known screening method.

Specifically, monoclonal or polyclonal antibodies may be generated as follows.

Though the sensitizing antigen for generation of antibodies is not limited by the animal species from which the antibodies are obtained, it is preferably derived from a mammal from which peptides or polypeptides actually used in the present invention are derived, such as humans, mice, or rats. Among them, sensitizing antigens derived from humans are preferred. When, for example, a human TAB1 polypeptide or human TAK1 polypeptide is used as the sensitizing antigen, the nucleotide sequence and the amino acid sequence thereof can be obtained using the gene sequence disclosed in the present invention. Furthermore, when other peptides or polypeptides that are fused with the human TAB1 polypeptide or human TAK1 polypeptide are used as the sensitizing antigen, the peptides and the polypeptides can be chemically synthesized or can be obtained using genetic engineering technology.

Peptides or polypeptides that are used as the sensitizing antigen may be full-length or fragments thereof. As fragments, for example, C-terminal fragments or N-terminal fragments may be mentioned.

Mammals to be immunized with the sensitizing antigen are not specifically limited, and they are preferably selected in consideration of their compatibility with the parent cell for use in cell fusion. They generally include rodents, lagomorphs, and primates.

Rodents include, for example, mice, rats, hamsters, and the like. Lagomorphs include, for example, rabbits. Primates include, for example, monkeys. As monkeys, catarrhines (Old-World monkeys) such as cynomolgi (crab-eating macaque), rhesus monkeys, sacred baboons, chimpanzees etc. are used.

Immunization of animals with a sensitizing antigen is carried out using a known method. A general method, for example, involves the intraperitoneal or subcutaneous administration of a sensitizing antigen to the mammal. Specifically, a sensitizing antigen which has been diluted and suspended in an appropriate amount of phosphate buffered saline (PBS) or physiological saline etc. is mixed, as desired, with an appropriate amount of a conventional adjuvant, for example Freund's complete adjuvant. After being emulsified, it is preferably administered to the mammal for several times every 4 to 21 days. Alternatively a suitable carrier may be used at the time of immunization of the sensitizing antigen. After such immunization, the increase in the desired antibody levels in the serum is confirmed by a conventional method.

In order to obtain polyclonal antibodies, the blood of the mammal that was sensitized with the antigen is removed after the increase in the desired antibody levels in the serum has been confirmed. Serum is separated from the blood. As polyclonal antibodies, serum containing the polyclonal antibodies may be used, or, as desired, the fraction containing the polyclonal antibodies may be isolated from the serum.

In order to obtain monoclonal antibodies, immune cells of the mammal that was sensitized with the antigen are removed and are subjected to cell fusion after the increase in the desired antibody levels in the serum has been confirmed. At this time preferred immune cells that are subjected to cell fusion include, in particular, the spleen cells.

The mammalian myeloma cells as other parent cells which are subjected to cell fusion with the above-mentioned immune cells preferably include various known cell lines such as P3 (P3X63Ag8.653) (Kearney, J. F. et al., J. Immunol. (1979) 123: 1548–1550), P3X63Ag8.U1 (Yelton, D. E., et al., Current Topics in Microbiology and Immunology (1978) 81: 1–7), NS-1 (Kohler, G. and Milstein, C., Eur. J. Immunol. (1976) 6: 511–519), MPC-11 (Margulies, D. H. et al., Cell (1976) 8: 405–415), SP2/0 (Shulman, M. et al., Nature (1978) 276: 269–270), OF (de St. Groth, S. F. and Scheidegger, D., J. Immunol. Methods (1980) 35: 1–21), S194 (Trowbridge, I. S., J. Exp. Med. (1978) 148: 313–323), R210 (Galfre, G. et al., Nature (1979) 277: 131–133) and the like.

Cell fusion between the above immune cells and the myeloma cells may be essentially conducted in accordance with a known method such as is described in Milstein et al. (Kohler, G. and Milstein, C., Methods Enzymol. (1981) 73: 3–46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v), and mixed to obtain the desired fusion cells (hybridomas). Then by repeating the sequential addition of a suitable culture liquid and centrifugation to remove the supernatant, cell fusion agents etc. which are undesirable for the growth of the hybridoma can be removed.

Said hybridoma is selected by culturing in a conventional selection medium, for example, the HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally several days to several weeks. Then, the conventional limiting dilution method is conducted in which the hybridomas that produce the desired antibody are screened and cloned.

In addition to obtaining the above hybridoma by immunizing an animal other than the human with an antigen, it is also possible to sensitize human lymphocytes infected with EB virus with a peptide or polypeptide, cells expressing them, or their lysates in vitro, and to allow the resulting sensitized lymphocytes to be fused with a human-derived myeloma cell having a permanent division potential, for example U266, and thereby to obtain a hybridoma producing the desired human antibody having the activity of binding the peptide or the polypeptide (see Japanese Unexamined Patent Publication (Kokai) No. 63(1988)-17688).

Furthermore, a transgenic animal having a repertoire of human antibody genes is immunized with the antigen peptide or polypeptide, cells expressing them or lysates thereof to obtain the antibody-producing cells, which are used to obtain human antibody against the peptide or polypeptide for use in the present invention using hybrodomas fused to myeloma cells (see International Patent Application WO 92-03918, WO 93-2227, WO 94-02602, WO 94-25585, WO 96-33735 and WO 96-34096).

The monoclonal antibody-producing hybridomas thus constructed can be subcultured in the conventional culture liquid, or can be stored for a prolonged period of time in liquid nitrogen.

In order to obtain monoclonal antibodies from said hybridoma, there may be employed a method in which said hybridoma is cultured in the conventional method and the antibodies are obtained as the culture supernatant, or a method in which the hybridoma is administered to and grown in a mammal compatible with said hybridoma and the antibodies are obtained as the ascites. The former method is suitable for obtaining high-purity antibodies, whereas the latter is suitable for a large scale production of antibodies.

In addition to using a hybridoma to produce antibody, immune cells that produce the desired antibody, for example the sensitized lymphocytes that have been immortalized with an oncogene, may be used to obtain the antibody.

A monoclonal antibody thus produced can also be obtained as a recombinant antibody by recombinant gene technology. For example, an antibody gene may be cloned from the hybridoma or an immune cell such as sensitized lymphocytes that produce antibodies, and is integrated into a suitable vector which is then introduced into a host to produce said antibody. Recombinant antibodies may also be used in the present invention (see, for example, Borrebaeck, C. A. K., and Larrick, J. W., THERAPEUTIC MONOCLONAL ANTIBODIES, published in the United Kingdom by MACMILLAN PUBLISHERS LTD. 1990).

Antibodies for use in the present invention may be antibody fragments or modified versions thereof as long as they have the desired binding activity. For example, as fragments of antibody, there may be mentioned Fab, F(ab')$_2$, Fv or single-chain Fv (scFv) in which Fv or Fv's of the H chain and the L chain were ligated via a suitable linker. Specifically antibodies are treated with an enzyme such as papain or pepsin, to produce antibody fragments, or genes encoding these antibody fragments are constructed and then introduced into an expression vector, which is expressed in a suitable host cell (see, for example, Co, M. S. et al., J. Immunol. (1994) 152, 2968–2976; Better, M. and Horwitz, A. H., Methods in Enzymology (1989) 178, 476–496; Plucktrun, A. and Skerra, A., Methods in Enzymol. (1989) 178, 497–515; Lamoyi, E., Methods in Enzymol. (1986) 121, 652–663; Rousseaux, J. et al., Methods in Enzymol. (1986) 121, 663–669; Bird, R. E. and Walker, B. W., Trends Biotechnol. (1991) 9, 132–137).

Antibodies produced and expressed as described above can be separated from the inside or outside of the host cell and then may be purified to homogeneity. Separation and purification of the antibody for use in the present invention may be accomplished by, but is not limited to, the separation and the purification methods conventionally used for proteins.

These methods include chromatography columns such as affinity chromatography, filtration, ultrafiltration, salting-out, dialysis, SDS polyacrylamide gel electrophoresis, isoelectric focusing, and the like, from which methods can be selected and combined as appropriate for separation and purification of antibodies (Antibodies: A Laboratory Manual, Ed Harlow and David Lane, Cold Spring Harbor Laboratory, 1988).

As columns for use in affinity chromatography, there can be mentioned Protein A column and Protein G column. Examples of the carriers used in the Protein A column are Hyper D, POROS, Sepharose F. F. (Pharmacia) and the like.

As chromatography other than the above-mentioned affinity chromatography, there can be mentioned, for example, ion exchange chromatography, hydrophobic chromatography, gel-filtration, reverse phase chromatography, adsorption chromatography, and the like (Strategies for Protein Purification and Characterization: A Laboratory Course Manual, Ed Daniel R. Marshak et al., Cold Spring Harbor Laboratory Press, 1986). These chromatographies can be carried out using a liquid chromatography such as HPLC and FPLC.

The concentration measurement and activity confirmation of the antibody obtained as above can be made by known methods such as enzyme-linked immunosorbent assay (ELISA), radioimmunoassay (RIA), or fluorescent antibody assay.

Substances that inhibit binding between the TAB1 polypeptide and the TAK1 polypeptide that were obtained using the screening method of the present invention can be obtained by screening the test compounds such as peptides, proteins, non-peptide compounds, synthetic compounds, microbial fermentation products, marine organism extracts, plant extracts, cell extracts, or animal cell extracts by screening methods. These test compounds may be novel compounds, or existing compounds.

These binding-inhibiting substances are compounds that inhibit binding between the TAB1 polypeptide and the TAK1 polypeptide. Compounds that were changed by addition, deletion, or substitution of part of the structure of substances that inhibit binding between the TAB1 polypeptide and the TAK1 polypeptide obtained by the screening method of the present invention are included in the substances that inhibit binding between the TAB1 polypeptide and the TAK1 polypeptide obtained by the screening method of the present invention.

Substances that inhibit binding between the TAB1 polypeptide and the TAK1 polypeptide obtained by the screening method of the present invention may be substances that activate signal transduction of TGF-$\beta$ or substances that suppress signal transduction of TGF-$\beta$. TGF-$\beta$ is known to have the effect of enhancing extracellular matrix protein production, inhibiting cellular growth, causing monocyte migration, inducing biologically active substances, suppressing immunity, depositing amyloid β protein, and the like. Both of the TAB1 polypeptide and the TAK1 polypeptide are responsible for signal transduction of TGF-β each by binding thereto. Thus, substances that inhibit binding between the TAB1 polypeptide and the TAK1 polypeptide obtained by the screening method of the present invention can be obtained as a substance that activates or suppresses signal transduction of TGF-β.

When substances that inhibit binding between the TAB1 polypeptide and the TAK1 polypeptide obtained by the screening method of the present invention are used as medicaments for humans and mammals such as mice, rats, guinea pigs, rabbits, chickens, cats, dogs, sheep, pigs, cattle, monkeys, baboons, and chimpanzees, they may be used in the conventional method.

For example, they may be used, as desired, orally as capsules and microcapsules, or parenterally in the form of sterile solutions with water or other pharmaceutically acceptable liquids or suspensions. For example, substances that inhibit binding between the TAB1 polypeptide and the TAK1 polypeptide are produced in unit dosage forms required for generally accepted formulations by mixing with pharmaceutically acceptable carriers, excipients, vehicles, antiseptics, stabilizers, and adhesion inhibitors. The amount of active ingredients in these formulations is designed to provide an indicated suitable range of doses. As additives that may be blended for tables or capsules, for example, gelatin, HSA (human serum albumin), crystalline cellulose, alginic acid, magnesium stearate, sucrose, and lactose may be used.

As aqueous solutions for injection, there may be mentioned, for example, isotonic liquids such as physiological saline, glucose and other adjuvants such as D-sorbitol, D-mannose, D-mannitol, and sodium chloride, and they may be used in combination with suitable solubilizing agents such as alcohols, specifically ethanol, polyalchohols including, for example, propylene glycol and polyethylene glycol, nonionic surfactants such as polysorbate 8OTM, HCO-50, benzyl benzoate, phosphate buffer, sodium acetate buffer, procaine hydrochloride, benzyl alchohol, and phenol.

The dosage of substances that inhibit binding between the TAB1 polypeptide and the TAK1 polypeptide for a human adult (assuming the body weight of 60 kg) is, when given orally, usually about 0.1 to 100 mg/day, preferably about 1.0 to 50 mg/day, and more preferably about 1.0 to 20 mg/day, though this may vary depending on the medical conditions.

When given parenterally, the dose per administration for a human adult (assuming the body weight of 60 kg) of usually about 0.01 to 30 mg/day, preferably about 0.1 to 20 mg/day, and more preferably about 0.1 to 10 mg/day in the case of injections is conveniently administered via intravenous injection, though this may vary depending on the subject organ, medical conditions, and the method of administration. For other animals, the amount converted in terms of the body weight of 60 kg may be administered.

EXAMPLES

The present invention will now be explained in more details with reference to the examples. It should be noted, however, that the present invention is not limited to them in any way.

Example 1

Construction of a Baculovirus Transfer Vector for Recombinant Human TAB1 and Recombinant Human TAK1

In order to express a full-length human TAB1 polypeptide and a full-length human TAK1 polypeptide by a baculovirus expression system, a baculovirus transfer vector was constructed. At this time, it was designed to add a peptide tag in order to facilitate purification and detection.

Thus, a FLAG tag comprising 8 amino acids (Asp-Tyr-Lys-Asp-Asp-Asp-Asp-Lys; SEQ ID NO: 5) was added to the carboxy terminal of human TAB1. Also, a 6×His tag (Janknecht, R. et al., Gene (1992) 121, 321–324) comprising 6 contiguous His residues (His-His-His-His-His-His; SEQ ID NO: 6) was added to the carboxy terminal of human TAK1. Each recombinant polypeptide is expressed as a fusion polypeptide, human TABL-FLAG or human TAK1-6×His.

In order to obtain a DNA fragment encoding human TAB1-FLAG, a PCR method was carried out with plasmid pBS-TAB1 (Shibuya, H. et al., Science (1996) 272, 1179–1182) as a template using a sense primer TABFS (SEQ ID NO: 7) and an antisense primer TAB1AS (SEQ ID NO: 8) that were synthesized using a primer synthesizer.

The sense primer TABFS comprises a nucleotide sequence from nucleotide A at position 30 to nucleotide G at position 47 of the region encoding a full-length human TAB1 polypeptide contained in plasmid PBS-TAB1 as set forth in SEQ ID NO: 1 or 2 after the recognition site of the restriction enzyme EcoRI. The antisense primer TAB1AS comprises a nucleotide sequence complementary to a series of nucleotide sequences comprising a nucleotide sequence encoding 5 amino acid sequence comprised of Gly-Thr-Gly-Gly-Ser (SEQ ID NO: 9), a nucleotide sequence encoding the FLAG tag, two stop codons, and a recognition site of the restriction enzyme XbaI, after a nucleotide sequence from nucleotide A at position 1524 to nucleotide G at position 1541 of the region encoding the human TAB1 polypeptide contained in the plasmid pBS-TAB1 as set forth in SEQ ID NO: 3 or 4 (FIG. 1).

The PCR method comprised a total of 25 cycles of 94° C. for 1 minute, 55° C. for 1 minute, and 72° C. for 2 minutes per cycle. PCR reaction products were separated and purified by a 1% low-melting point agarose gel (manufactured by Sigma), digested with the restriction enzymes EcoRI and XbaI, and then were inserted into the baculovirus transfer vector pBacPAK9 (manufactured by CLONTECH).

The nucleotide sequence of the inserted DNA fragment was determined by a DNA sequencer (Model 373A, manufactured by ABI) thereby to confirm that the correct nucleotide sequence had bee inserted.

The plasmid comprising a nucleotide sequence encoding human TAB1-FLAG was designated as pBacTABF. The nucleotide sequence and the amino acid sequence encoding human TAB1-FLAG are shown in SEQ ID NO: 10 and 11.

In order to obtain a DNA fragment encoding human TAK1-6×His, a PCR method was carried out with plasmid phTAK1 (Japanese Unexamined Patent Publication (Kokai) No. 9(1997)-163990) as a template using a sense primer TAKS (SEQ ID NO: 12) and an antisense primer TAKAS (SEQ ID NO: 13) that were synthesized using a primer synthesizer.

The sense primer TAKS comprises a nucleotide sequence from nucleotide A at position 183 to nucleotide C at position 200 of the region encoding a human TAB1 polypeptide contained in plasmid phTAK1 as set forth in SEQ ID NO: 3 after the recognition site of the restriction enzyme EcoRI. The antisense primer TAKAS comprises a nucleotide sequence complementary to a nucleotide sequence encoding 5 amino acid sequence comprised of Gly-Thr-Gly-Gly-Ser, a nucleotide sequence encoding the 6×His tag, two stop codons, and a recognition site of the restriction enzyme XbaI, after a nucleotide sequence from nucleotide A at position 1902 to nucleotide A at position 1919 of the region encoding the human TAK1 polypeptide contained in plasmid phTAK1 (FIG. 1).

The PCR method comprised a total of 25 cycles of 94° C. for 1 minute, 55° C. for 1 minute, and 72° C. for 2 minutes per cycle. PCR reaction products were separated and purified by a 1% low-melting point agarose gel (manufactured by Sigma), digested with the restriction enzymes EcoRI and XbaI, and then were inserted into the baculovirus transfer vector pBacPAK9 (manufactured by CLONTECH). The nucleotide sequence of the inserted DNA fragment was determined by a DNA sequencer (Model 373A, manufactured by ABI) thereby to confirm that the correct nucleotide sequence had been inserted. The plasmid comprising a nucleotide sequence encoding human TAK1-6×His was designated as pBacTAKF. The nucleotide sequence and the amino acid sequence encoding human TAK1-6×His are shown in SEQ ID NO: 14 and 15.

Example 2

Expression of Recombinant Human TAB1-FLAG and Human TAK1-6×His Polypeptides

Example 2-1

Construction of a Recombinant Baculovirus

A recombinant baculovirus was constructed in accordance with the instructions by CLONTECH.

Thus, for the construction of the recombinant human TAB1-FLAG baculovirus, 0.5 μg of the transfer vector pBacTABF of the above Example 1, 5 μl of the Bsu36 I digest of baculovirus BacPAK6 DNA (manufactured by CLONTECH), and 50 μl of a 0.1 mg/ml lipofectin solution (manufactured by CLONTECH) were diluted to a total of 100 μl in distilled water. The aqueous solution was mixed with 1.5 ml of serum-free medium and was added with $1 \times 10^6$ lined insect cells Sf9 (ATCC CRL 1711).

At 5 hours after the addition, 1.5 ml of the insect cell culture medium (containing a medium supplement for the Grace insect cells, manufactured by GIBCO BRL) supplemented with 10% fetal bovine serum was further added, incubated at 27° C. for 5 days, and then the supernatant was recovered. Using the culture supernatant, a plaque assay was carried out according to the instructions by the manufacturer to isolate a recombinant baculovirus that expresses recombinant TAB1-FLAG from a single plaque.

Using the transfer vector pBacTAKF described in the above Working Example 1 in a similar procedure, a recombinant baculovirus expressing the recombinant human TAK1-6×His was constructed.

Example 2-2

Expression of Each Recombinant Polypeptide Using a Recombinant Baculovirus

A 100 M.O.I. amount of a recombinant baculovirus was infected to $1 \times 10^9$ lined insect cells Sf9, and was incubated in 1000 ml of an insect cell culture medium supplemented with 2% fetal bovine serum at 27° C. for 5 days. Cells after incubation were washed three times in PBS (Dulbecco PBS, manufactured by Nissui), and were subjected to the following purification.

Example 3

Purification of Recombinant Human TAB1-FLAG and Human TAK1-6×His Polypeptide

Example 3-1

Purification of the Recombinant Human TAB1-FLAG Polypeptide (1) Preparation of a Cleared Lysate After the cells obtained in the above 2-2 were suspended in the TMN buffer (20 mM Tris-HCl, 3 mM MgCl$_2$, 150 mM NaCl, 0.1 mg/ml PMSF, 1 μg/ml leupeptin, 1 μg/ml aprotinin, pH 7.5) to a density of $4 \times 10^7$ cells/ml, the cells were treated by an ultrasonic disrupting instrument (SONIFIER 250, manufactured by BRANSON) until 90% of the cells were disrupted. The insoluble material in the disrupted solution was precipitated by centrifuging by a centrifuge (model MRX-150, manufactured by TOMY) at 14,000 rpm for 10 minutes. The supernatant thus obtained was filtered using a 0.45 μm filter (Sterivex™-HV, manufactured by MILLIOPORE), and the filtrate was used as the cleared lysate.

(2) Purification with an Anti-FLAG M2 Affinity Gel

In order to purify the recombinant human TAB1-FLAG polypeptide from the cleared lysate, affinity purification with anti-FLAG antibody was carried out as follows:

Two ml of the anti-FLAG antibody M2 affinity gel (manufactured by IBI) was equilibrated with a TBS buffer (50 mM Tris-HCl, 150 mM NaCl, pH 7.4) in the bed support (Poly-Prep Chromatography Column, manufactured by BIO-RAD). The above supernatant was added to the equilibrated anti-FLAG antibody M2 affinity gel, and the human TAB1-FLAG polypeptide was bound thereto. The column was washed with 30 ml of the TBS buffer, and the bound polypeptide was eluted with 2 ml each of the elution buffer (0.1 M glycine-HCl, pH 3.5) in six portions.

After the elution, the elution buffer was replaced with PBS using the gel filtration column PD-10 (manufactured by Pharmacia), which was used as a purified product of the recombinant human TAB1-FLAG polypeptide. The purity of the recombinant human TAB1-FLAG polypeptide was measured by the BCA* Protein Assay Reagent (manufactured by PIERCE) using BSA as a standard.

Example 3-2

Purification of the Recombinant Human TAK1-6× His Polypeptide (1) Preparation of the Cleared Lysate The cells obtained in the above 2-2 were suspended in the sonication buffer (20 mM Tris-HCl, 100 NaCl, 0.1 mg/ml PMSF, 1 μg/ml leupeptin, 1 μg/ml aprotinin, pH 8.0) to a density of $4 \times 10^7$ cells/ml, and then the cells were treated by an ultrasonic disrupting instrument (SONIFIER 250, manufactured by BRANSON) until 90% of the cells were disrupted. The insoluble material in the disrupted solution was precipitated by centrifuging by a centrifuge (model MRX-150, manufactured by TOMY) at 14000 rpm for 10 minutes. The supernatant thus obtained was filtered using a 0.45 μm filter (Sterivex™-HV, manufactured by MILLIOPORE), and the filtrate was used as the cleared lysate.

(2) Purification with TALON™ Metal Affinity Resin

In order to purify the recombinant human TAK1-6×His polypeptide from the cleared lysate, purification with affinity resin (TALON™ Metal Affinity Resin, manufactured by CLONTECH) was carried out as follows:

Two ml of the affinity resin equilibrated with the sonication buffer and the cleared lysate of the above working Example 3-2 (1) were mixed under shaking for 20 minutes, to which the recombinant human TAK1-6×His polypeptide was ligated. After removing the supernatant by centrifugation at 700×g, the affinity resin was mixed under shaking in 20 ml of the wash buffer (10 mM imidazole, 20 mM Tris-HCl, 100 mM NaCl, pH 8.0) at 4° C. for 10 minutes, followed by the removal of the supernatant by centrifugation at 700×g.

After the affinity resin was mixed under shaking in 20 ml of the wash buffer (10 mM imidazole, 20 mM Tris-HCl, 100 mM NaCl, pH 8.0) at 4° C. for 10 minutes, the resin was washed by removing the supernatant by centrifugation at 700×g. The affinity resin after washing was suspended in 2 ml of the wash buffer and was transferred to the bed support (Poly-Prep Chromatography Column, manufactured by BIO-RAD), and the affinity resin was further washed with 6 ml of the wash buffer.

The affinity resin was subjected to elution by the elution buffer (50 mM imidazole, 20 mM Tris-HCl, 100 mM NaCl, pH 8.0) in six portions of 2 ml each. After elution, the elution buffer was replaced with PBS using the gel filtration column PD-10 (manufactured by Pharmacia), which was used as a purified product of the recombinant human TAK1-6×His polypeptide. The purity of the recombinant human TAK1-6×His polypeptide was measured by the BCA* Protein Assay Reagent (manufactured by PIERCE) using BSA as a standard.

Example 4

Preparation of the Recombinant MBP-TAB1C-FLAG

Example 4-1

Construction of the Expression Vector

By an expression system using *Escherichia coli* (*E. coli*), an expression vector for expression in *E. coli* of a fusion polypeptide of a polypeptide comprising 81 amino acids at the carboxy terminal of the human TAB1 polypeptide and maltose-binding protein was constructed. At this time, a FLAG tag was added to the carboxy terminal of the above fusion polypeptide in order to facilitate purification and detection.

In order to obtain a DNA fragment encoding 81 amino acids at the carboxy terminal of the human TAB1 and the FLAG tag, a PCR method was carried out with plasmid pBacTABF as a template using a sense primer TABC1 (SEQ ID NO: 16) and an antisense primer TABC3 (SEQ ID NO: 17) that were synthesized using a primer synthesizer.

The sense primer TABC1 comprises a nucleotide sequence from nucleotide C at position 1281 to nucleotide T at position 1307 of the region encoding the human TAB1 polypeptide contained in plasmid pBacTABF as set forth in SEQ ID NO: 9 after the recognition site of the restriction enzyme XmnI.

The antisense primer TAB1AS comprises a nucleotide sequence complementary to a series of nucleotide sequences comprising a nucleotide sequence encoding a nucleotide sequence encoding the FLAG tag, two stop codons, and a recognition site of the restriction enzyme HindIII, after a nucleotide sequence from nucleotide C at position 1489 to nucleotide G at position 1518 of the region encoding the human TAB1 polypeptide contained in the plasmid pBacTABF as set forth in SEQ ID NO: 9.

The PCR method comprised a total of 25 cycles of 94° C. for 1 minute, 55° C. for 1 minute, and 72° C. for 1 minute per cycle. PCR reaction products were separated and purified by a 1% low-melting point agarose gel (manufactured by Sigma), digested with the restriction enzymes XmnI and HindIII, and then were inserted into a fusion polypeptide expression vector pMAL-p2 (manufactured by New England Biolabs).

Example 4-2

Expression of the Fusion Polypeptide

A fusion polypeptide was expressed according to the instructions by New England Biolabs. Thus, *E. coli* having the plasmid obtained as above was grown overnight and 2 ml thereof was inoculated into 200 ml of a rich broth (10 g tryptone, 5 g yeast extract, 5 g NaCl, 2 g glucose, 100 mg ampicillin/liter). It was incubated under shaking at 37° C. till the cell density reached $A_{600}=1$, at which time IPTG (isopropylthiogalactoside) was added to a final concentration of 0.3 mM. It was further incubated under shaking at 37° C. for 2 hours and then was centrifuged at 4000×g for 10 minutes to harvest the cells.

Example 4-3

Preparation of the Periplasm Fraction

The cells collected in the above Example 4-2 was resuspended in 25 ml of 30 mM Tris, 20% sucrose, pH 8.0, and 50 μl of 0.5 M EDTA, pH 8.0, was added thereto followed by incubation under shaking for 10 minutes. Subsequently, it was cetrifuged at 8000×g to remove the supernatant and the cells were resuspended in 25 ml of ice-cold 5 mM $MgSO_4$ and was further incubated under shaking in the ice. After centrifugation at 8000×g, the supernatant was recovered as the periplasm fraction.

Example 4-4

Purification with the Anti-FLAG M2 Affinity Gel

In order to purify recombinant MBP-TAB1C-FLAG polypeptide from the periplasm fraction, affinity purification with anti-FLAG M2 antibody was carried out in a similar manner to Example 3-1 (2) to obtain a purified product of the recombinant MBP-TAB1C-FLAG polypeptide.

Example 5

Construction of an ELISA System Using the Purified Product

Using the purified product obtained as above an ELISA system was constructed to detect in vitro an interaction between the recombinant human TAB1 polypeptide or the recombinant MBP-TAB1C-FLAG polypeptide and the recombinant human TAK1 polypeptide. In the ELISA system it is intended to contact the recombinant human TAB1-FLAG polypeptide or the human MBP-TABLC-FLAG polypeptide to a 96-well immunoplate to which the human TAK1-6×His polypeptide had been previously immobilized and thereby to detect the recombinant human TAB1-FLAG polypeptide or the recombinant MBP-TAB1C-FLAG polypeptide using a primary and secondary antibody.

Example 5-1

Construction of an In Vitro Binding-evaluation System (1) The purified product of human TAK1-6×His polypeptide was diluted in the immobilization buffer (0.1 M $NaHCO_3$, 0.02% $NaN_3$, pH 9.6). To each well of a 96-well immunoplate (manufactured by Nunc) was added 100 μl each of the diluted aqueous solution (equivalent to 100 ng of the human TAK1-6×His polypeptide), and the plate was incubated overnight at 4° C.

After each well was washed three times with the wash buffer (diluted to 0.05% Tween 20 in PBS), 200 μl of a 5% BSA (manufactured by SIMGA) solution dissolved in PBS was added thereto and was blocked overnight at 4° C.

Then each well was washed three times with the wash buffer, 100 μl of the human MBP-TAB1C-FLAG polypeptide diluted in the dilution buffer (1% BSA, 0.5% Tween 20, PBS) was added thereto and was incubated at room temperature for one hour. Then each well was washed three times with the wash buffer, 100 µl of rabbit anti-MBP antiserum (manufactured by New England Biolabs) diluted 5000-fold in the dilution buffer was added to each well and was incubated at room temperature for one hour. Then each well was washed three times with the wash buffer, 100 µl of alkaline phosphatase-labeled goat anti-rabbit antibody (manufactured by TAGO) diluted 5000-fold in the dilution buffer was added to each well and was incubated at room temperature for one hour.

After each well was washed five times with the wash buffer, 100 µl of the color development solution (the substrate buffer; p-nitrophenyl phosphate dissolved to 1 mg/ml in 50 mM NaHCO$_3$, 10 mM MgCl$_2$, pH 9.8, manufactured by Sigma) was added to each well and was incubated at room temperature, and then absorbance at 405 nm was determined using a microplate reader (Model 3550, manufactured by BIO-RAD).

The result confirmed that the absorbance increased depending on the concentration of the recombinant MBP-TAB1C-FLAG polypeptide. On the other hand, there were no increases in absorbance dependent on the concentration of the recombinant MBP-TAB1C-FLAG polypeptide in the group in which the human TAK1-6×His polypeptide was not immobilized (FIG. 2). This indicated that the contacted recombinant MBP-TAB1C-FLAG polypeptide specifically bound to the recombinant human TAK1-6×His polypeptide.

(2) The purified product of human TAK1-6×His polypeptide was diluted in the immobilization buffer (0.1 M NaHCO$_3$, 0.02% NaN$_3$, pH 9.6). To each well of a 96-well immunoplate (manufactured by Nunc) was added 100 µl each of the diluted aqueous solution (equivalent to 80 ng of the human TAK1-6×His polypeptide), and the plate was incubated overnight at 4° C.

After each well was washed three times with the wash buffer (diluted to 0.05% Tween 20 in PBS), 200 µl of a 5% BSA (manufactured by SIMGA) solution dissolved in PBS was added thereto and was blocked overnight at 4° C.

Then each well was washed three times with the wash buffer, and 100 µl of the human TAB1-FLAG polypeptide diluted in the dilution buffer (1% BSA, 0.5% Tween 20, PBS) was added and was incubated at room temperature for one hour. Then each well was washed three times with the wash buffer, 100 µl of mouse anti-FLAG antibody (manufactured by IBI) diluted to 3 µg/ml in the dilution buffer was added to each well, and was incubated at room temperature for one hour.

Then each well was washed three times with the wash buffer, 100 µl of alkaline phosphatase-labeled goat anti-mouse IgG antibody (manufactured by ZYMED) diluted 1000-fold in the dilution buffer was added to each well and was incubated at room temperature for one hour. After each well was washed five times with the wash buffer, 100 µl of the color development solution (the substrate buffer; p-nitrophenyl phosphate dissolved to 1 mg/ml in 50 mM NaHCO$_3$, 10 mM MgCl$_2$, pH 9.8, manufactured by Sigma) was added to each well and was incubated at room temperature, and then absorbance at 405 nm was determined using a microplate reader (Model 3550, manufactured by BIO-RAD).

Figure 3:
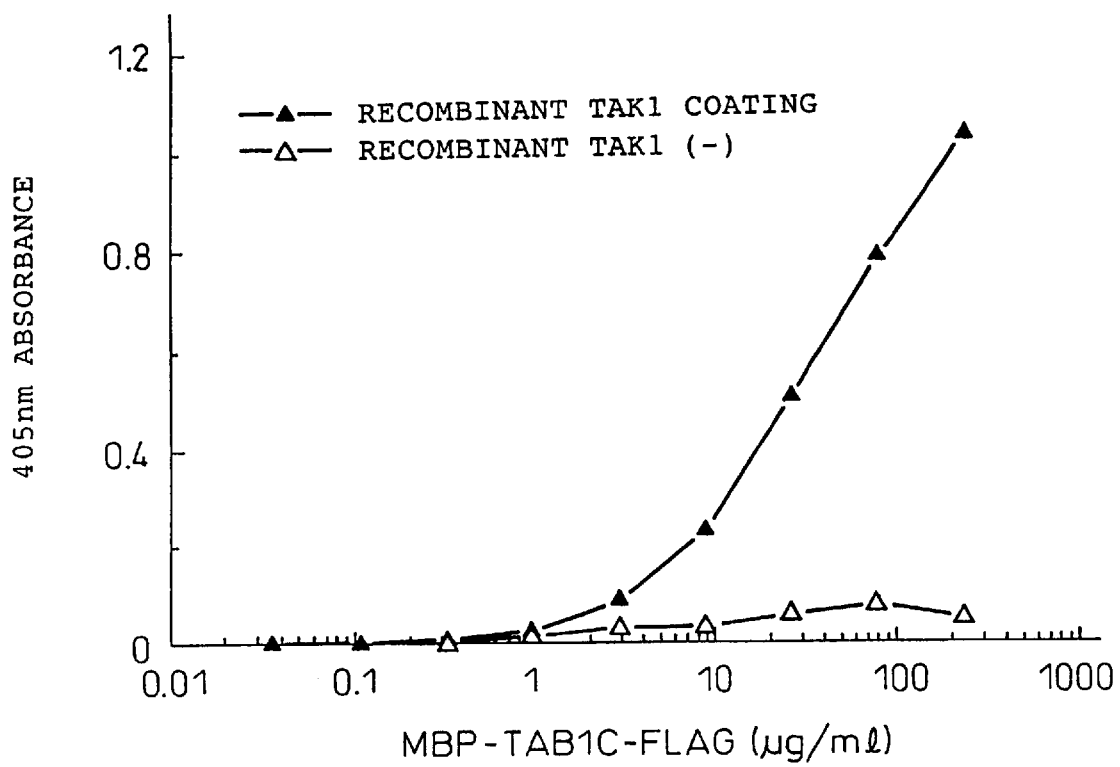
FIG. 3 is a graph showing binding between human TAB1-FLAG and human TAK1-6×His.

The result confirmed that the absorbance increased depending on the concentration of the recombinant human TAB1-FLAG polypeptide. On the other hand, there were no increases in absorbance dependent on the concentration of the human TAB1-FLAG polypeptide in the group in which the human TAK1-6×His polypeptide was not immobilized (FIG. 3).

This indicated that the recombinant human TAK1-6×His polypeptide that was prepared in the baculovirus expression system specifically bound to the human TAB1-FLAG polypeptide in vitro.

Example 5-2

A Binding-inhibition Study Using the Recombinant Human TAB1-FLAG Polypeptide

It was investigated whether the recombinant human TAB1-FLAG polypeptide used as an inhibiting substance inhibits binding between the recombinant MBP-TAB1C-FLAG polypeptide and the recombinant TAK1 polypeptide.

In a similar manner to that in the above 5-1 (2), the recombinant human TAK1-6×His polypeptide was immobilized and was blocked. Then the recombinant human TAB1-FLAG polypeptide that was serially diluted in the dilution buffer was added as a binding-inhibiting substance to each well together with 16.5 µl each of the recombinant MBP-TABLC-FLAG polypeptide and incubated.

Figure 4:
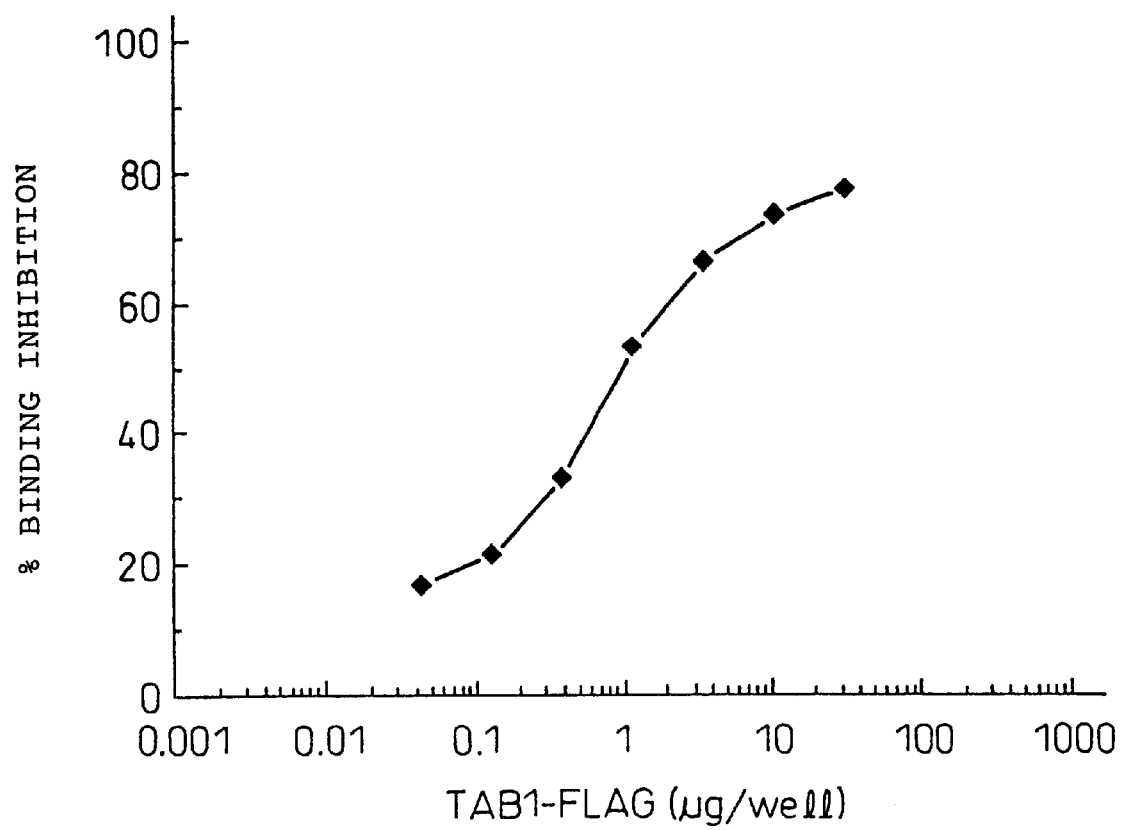
FIG. 4 is a graph showing the activity of inhibition of binding between human TAK1-6×His and human MBP-TAB1C-FLAG, determined using TAB1-FLAG as an inhibiting substance.

Thereafter, absorbance was determined as in the above, the result of which confirmed the decrease in absorbance dependent on the concentration of the recombinant human TAB1-FLAG polypeptide added as a binding-inhibiting substance (FIG. 4).

The foregoing has shown that the in vitro binding-evaluation system constructed in Example 2-1 is effective as a system for screening substances that inhibit binding between the TAK1 polypeptide and the MBP-TAB1C-FLAG polypeptide.

Example 6

Construction of the TAK1-DN Expression Vector and Establishment of the Recombinant In order to demonstrate that the signal transduction of TGF-β can be inhibited by inhibiting specific binding between the human TAK1 polypeptide and the human TAB1 polypeptide, TAK1-DN expression vector that acts as a dominant negative inhibitor was constructed, was introduced into various cells described below, and the reactivity to TGF-β was characterized.

TAK1-DN has an amino acid sequence comprising amino acid Glu at position 77 to amino acid Gln at position 303 of the amino acid sequence as set forth in SEQ ID NO: 4 which is the TAB1 binding site of the TAK1 polypeptide. The gene fragment encoding TAK1-DN was amplified using ph-TAK1 (Japanese Unexamined Patent Publication (Kokai) No. 9(1997)-163990) by the PCR method. Thus, using a sense primer TAK1S (SEQ ID NO: 18) containing the restriction enzyme EcoRI recognition site and the initiation codon ATG and an antisense primer TAKLAS (SEQ ID NO: 19) containing the restriction enzyme NotI recognition site and the stop codon, a DNA fragment encoding TAK1-DN was amplified.

The PCR products thus obtained were digested with restriction enzymes EcoRI and NotI, and then were inserted into an EcoRI recognition site of an animal cell expression vector pCOS1 containing EF1-α promoter and the neomycin resistant gene to produce an expression vector pTAK1DN. The expression vector pCOS1 was constructed by deleting the gene contained from plasmid HEF-PMh-gyl (see WO 92-19759) by digesting with EcoRI and Sam I and then ligating the EcoRI-NotI-bamHI Adaptor (manufactured by Takara Shuzo).

Then, pTAK1DN or pCOS1 that contains no inserted genes as a control vector was linearized by digesting with a restriction enzyme PvuI. These linearized vectors were introduced by electroporation into human fibroblast-derived HT-1080 (ATCC CCL 121), a mouse kidney mesangial cell line SV40MES13 (ATCC CRL 1927), and a mink pulmonary epithelial cell line Mv1Lu (ATCC CCL 64), and cells into which the gene was introduced were selected using G418 (manufactured by GIBCO-BRL).

Expression of each gene was confirmed by the RT-PCR method using primer TA5 (SEQ ID NO: 20) and primer HG1-R1 (SEQ ID NO: 21). Thus, mRNA was isolated from the gene-introduced cells using the Quick Prep mRNA Micro Purification kit (manufactured by Pharmacia). Then using the First Strand cDNA Synthesis kit (manufactured by Pharmacia), cDNA was synthesized from 150 ng of mRNA. The introduction of the gene was confirmed using 5 μl of cDNA reaction mixture as a template.

Example 7

The Action of TGF-β in Human Fibroblast-derived HT-1080

The human fibroblast-derived HT-1080 cells (HT/DN2 and HT/DN14) into which pTAK1DN had been introduced and the control cells (HT/NEO) into which pCOS1 containing no inserted genes had been introduced were incubated in a low-serum medium (Medium 199 containing 0.2% FBS; manufactured by GIBCO BRL) with or without 1 ng/ml TGF-β (manufactured by King Jozo) for 24 hours. The amount of fibronectin in the culture supernatant or the extracellular matrix extract prepared using 1 M urea solution (1 M urea, 1 mM DTT, 10 mM Tris-HCl, pH 7.4, 10 mM EDTA, Protease inhibitor cocktail (Complete™, manufactured by Boehringer Mannheim)) was determined by the EIA method.

Thus, 100 μl of the culture supernatant or the extracellular matrix extract prepared using 1 M urea solution was added to a 96-well microtiter plate (manufactured by Nunc), and the plate was incubated overnight at 4° C. After washing, it was blocked using a 1% BSA solution (50 mM Tris-HCl, pH 8.0, 1 mM $MgCl_2$, 150 mM NaCl, 0.05% Tween 20, 0.02% sodium azide), and then 10000 fold-diluted rabbit anti-human fibronectin antibody (manufactured by CALBIOCHEM) was added to the above 1% BSA solution, and was further incubated at room temperature for 2 hours.

After washing, alkaline phosphatase-labeled goat anti-rabbit Ig antibody (manufactured by TAGO) was added, and was further incubated at room temperature for one hour. Then the substrate solution (p-nitrophenyl phosphate; manufactured by Sigma) was added and absorbance at 450 nm was measured. As a standard, human fibronectin (manufactured by Cappel) was used.

Figure 5:
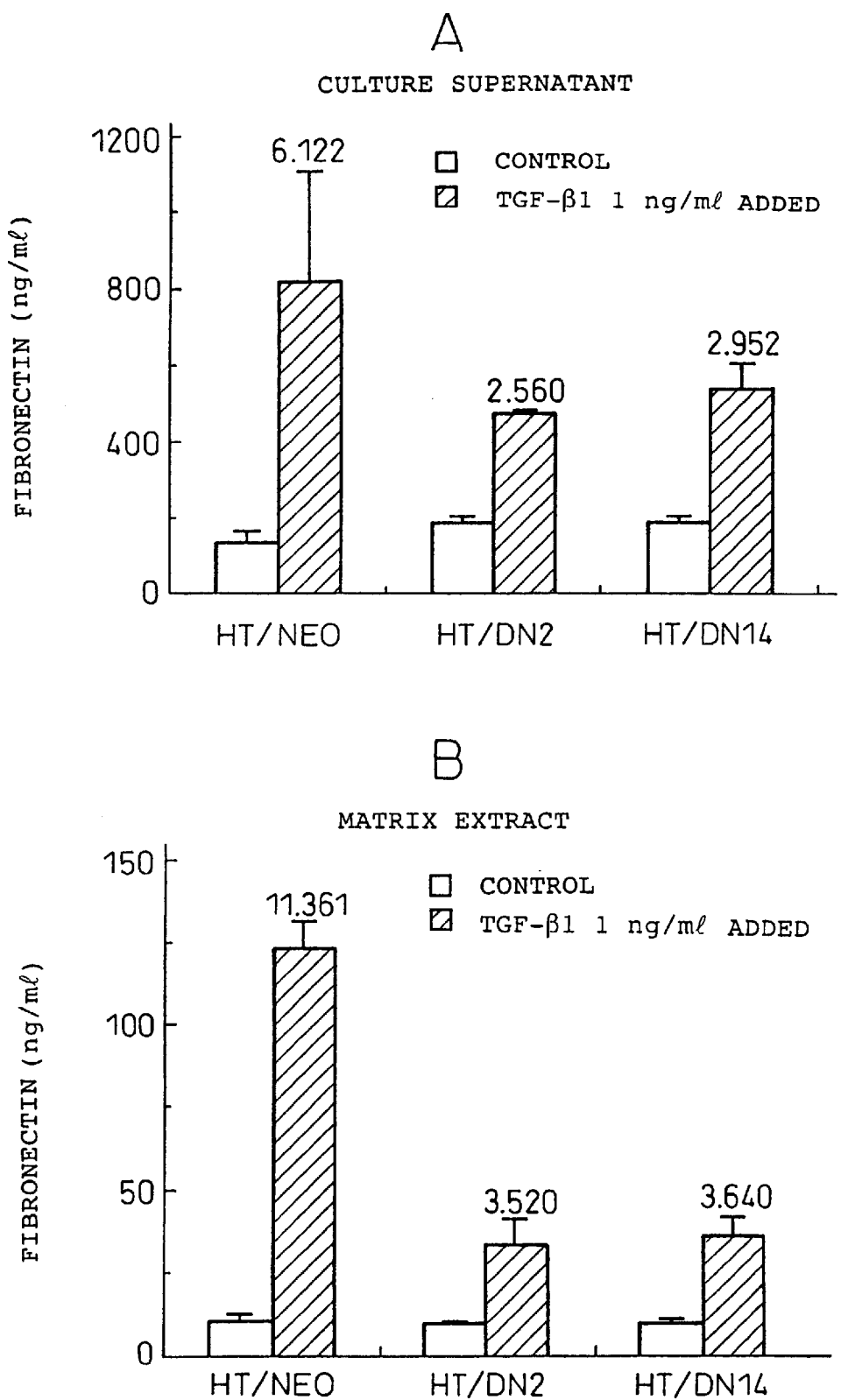
FIG. 5A is a graph showing the amount of fibronectin determined in the culture supernatant of the HT/NEO cells, the HT/DN2 cells and the HT/DN14 cells with and without the addition of TGF-β1. The values represent the mean+/−S.D. of the amount of fibronectin in the culture supernatant prepared from three different wells.
FIG. 5B is a graph showing the amount of fibronectin determined in the matrix extract of the HT/NEO cells, the HT/DN2 cells and the HT/DN14 cells with and without the addition of TGF-β1. The values represent the mean+/−S.D. of the amount of fibronectin in the matrix extract prepared from three different wells.

The results are shown in FIGS. 5A and B. In FIGS. 5A and B, the numerical values indicate the mean+/−SD of the culture supernatant and the extracellular matrix extracts prepared using 1 M urea, each prepared from 3 wells.

In the control cells HT/NEO, TGF-β addition increased fibronectin in the culture supernatant by about 6.1 fold, and that in the extracellular matrix extract by about 11.4 fold. On the other hand, in HT/DN2 and HT/DN14, cells that express TAK1-DN, fibronectin in the culture supernatant increased by about 2.6 and 3.0 fold, respectively, and that in the extracellular matrix extract increased by about 3.5 and 3.6 fold, respectively. These results indicated that the production of fibronectin by TGF-β and the incorporation of fibronectin into the matrix were suppressed by the expression of TAK1-DN.

Example 8

Effect of TGF-β on Mouse Kidney Mesangial Cell Line SV40MES13

The mouse mesangial cell line SV40MES13 (MES/DN3 and MES/DN6) into which pTAK1DN had been introduced and the control cells (MES/NEO) into which pCOS1 containing no inserted genes had been introduced were incubated in a low-serum medium (Medium 199 containing 0.2% FBS) with or without 2.5 ng/ml TGF-β for 24 hours. The amount of fibronectin in the culture supernatant or the extracellular matrix extract prepared using 1 M urea solution was determined by the EIA method as described in Example 7.

Figure 6:
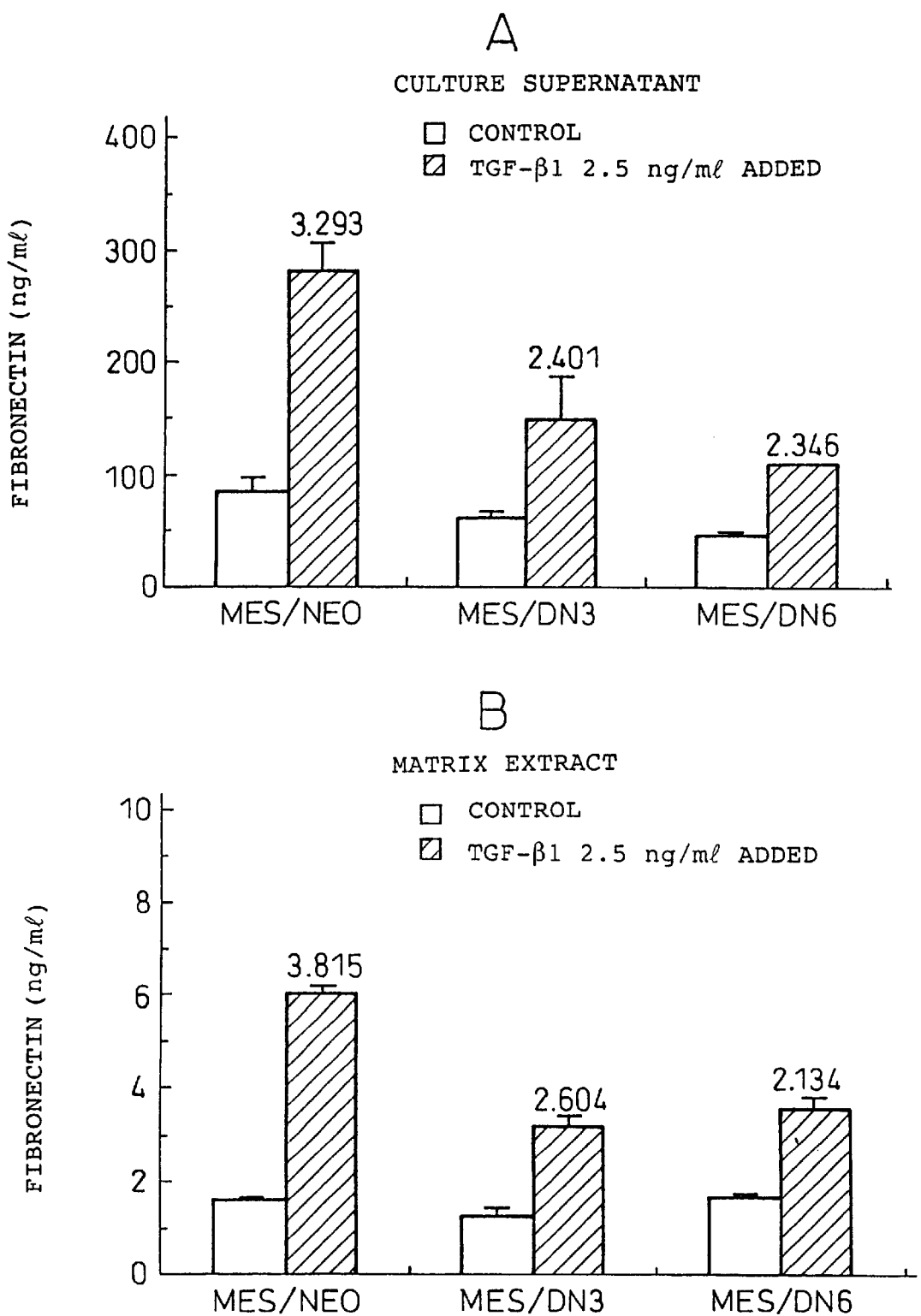
FIG. 6A is a graph showing the amount of fibronectin determined in the culture supernatant of the MES/NEO cells, the MES/DN3 cells and the MES/DN6 cells with and without the addition of TGF-β1. The values represent the mean+/−S.D. of the amount of fibronectin in the culture supernatant prepared from three different wells.
FIG. 6B is a graph showing the amount of fibronectin determined in the matrix extract of the MES/NEO cells, the MES/DN3 cells and the MES/DN6 cells with and without the addition of TGF-β1. The values represent the mean+/−S.D. of the amount of fibronectin in the matrix extract prepared from three different wells.

The results are shown in FIGS. 6A and B. In FIGS. 6A and B, the numerical values indicate the mean+/−SD of the culture supernatant and the extracellular matrix extracts prepared using 1 M urea, each prepared from 3 wells. In the control cells MES/NEO, TGF-β addition increased fibronectin in the culture supernatant by about 3.3 fold, and that in the extracellular matrix extract by about 3.8 fold. On the other hand, in MED/DN3 and MES/DN6, cells that express TAK1-DN, fibronectin in the culture supernatant increased by about 2.4 and 2.3 fold, respectively, and that in the extracellular matrix extract increased by about 2.6 and 2.1 fold, respectively. These results indicated that the production of fibronectin by TGF-β and the incorporation of fibronectin into the matrix were suppressed by the expression of TAK1-DN.

Furthermore, the amount of type I and type IV collagen in the culture supernatant was determined by the EIA method. Thus, 100 μl of the culture supernatant was added to a 96-well microtiter plate (manufactured by Nunc), and the plate was incubated overnight at 4° C. After washing, it was blocked using the above 1% BSA solution, and then 5000-fold diluted rabbit anti-mouse type I collagen antibody (manufactured by LSL) or rabbit anti-mouse type IV collagen antibody (manufactured by LSL) was added, and was further incubated at room temperature for 2 hours. After washing, alkaline phosphatase-labeled goat anti-rabbit Ig antibody (manufactured by TAGO) was added, and was further incubated at room temperature for one hour. Then the substrate solution (manufactured by Sigma) was added and absorbance at 450 nm was measured. As a standard, mouse type I collagen (manufactured by Chemicon) or mouse type IV collagen (manufactured by Cosmobio) was used.

Figure 7:
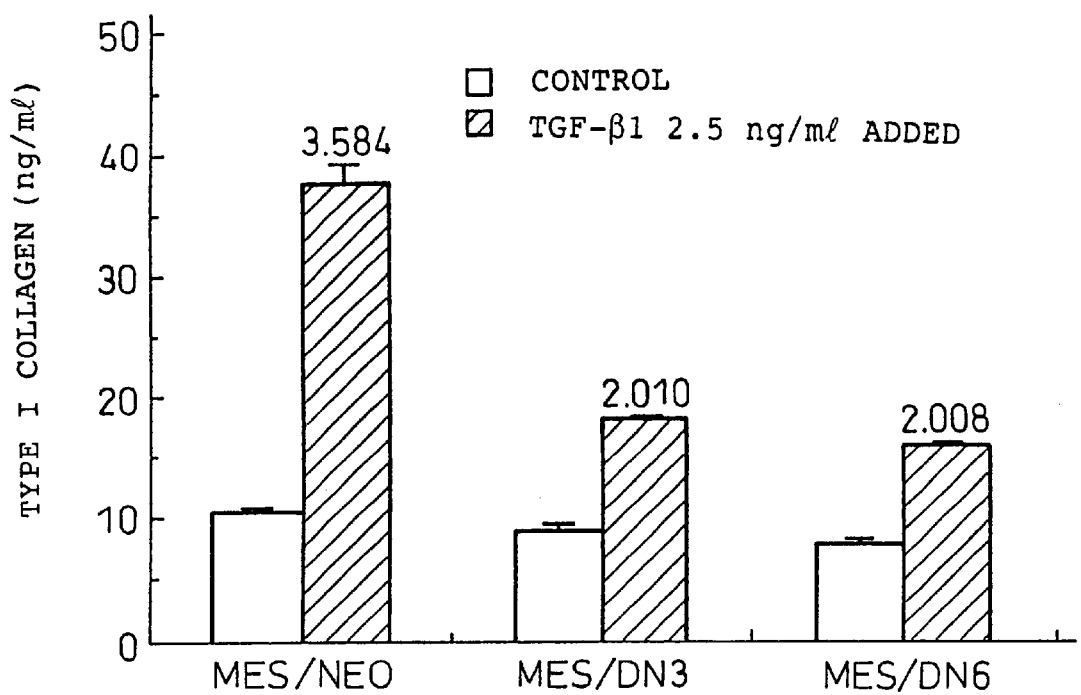
FIG. 7 is a graph showing the amount of type I collagen determined in the culture supernatant of the MES/NEO cells, the MES/DN3 cells and the MES/DN6 cells with and without the addition of TGF-β1. The values represent the mean+/−S.D. of the amount of type I collagen in the culture supernatant prepared from three different wells.
Figure 8:
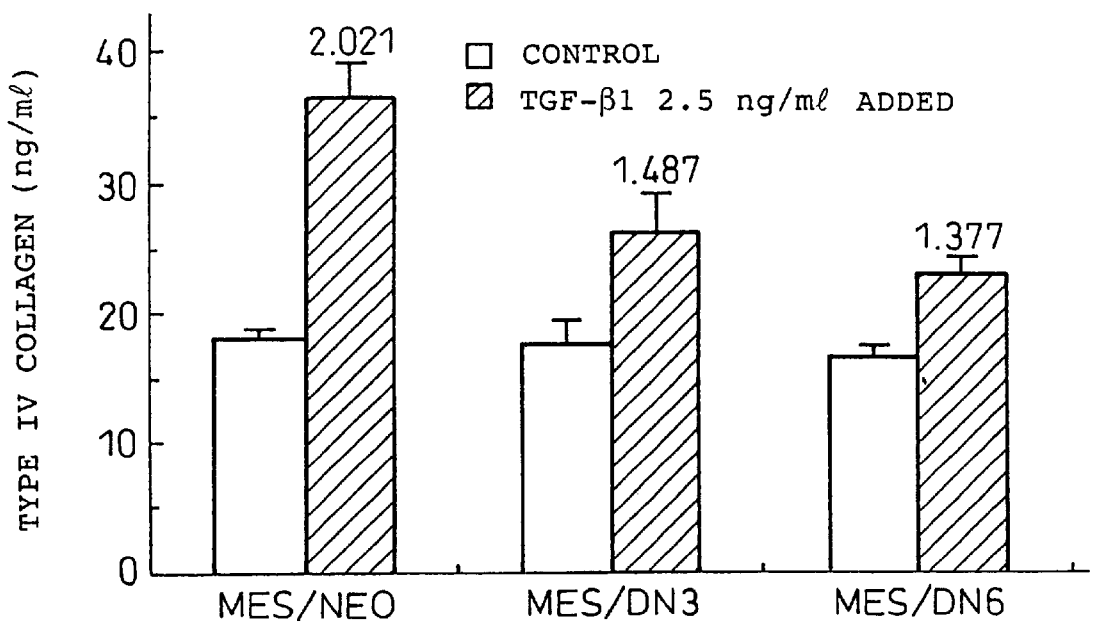
FIG. 8 is a graph showing the amount of type IV collagen determined in the culture supernatant of the MES/NEO cells, the MES/DN3 cells and the MES/DN6 cells with and without the addition of TGF-β1. The values represent the mean+/−S.D. of the amount of type IV collagen in the culture supernatant prepared from three different wells.

The results are shown in FIGS. 7 and 8. In FIGS. 7 and 8, the numerical values indicate the mean+/−SD of the culture supernatant and the extracellular matrix extracts prepared using 1 M urea, each prepared from 3 wells. In the control cells MES/NEO, TGF-β addition increased type I collagen in the culture supernatant by about 3.6 fold, and type IV collagen by about 2.0 fold. On the other hand, in MED/DN3 and MES/DN6, cells that express TAK1-DN, type I collagen in the culture supernatant increased by about 2.0 and 2.0 fold, respectively, and type IV collagen increased by about 1.5 and 1.4 fold, respectively. These results indicated that the production of type I collagen and type IV collagen by TGF-β was suppressed by the expression of TAK1-DN.

Example 9

Effect of TGF-β on Mink Epithelial Cell Line Mv1Lu

It is known that the cellular growth of mink epithelial cell line Mv1Lu is stopped at the G1 phase by stimulation with TGF-β. Accordingly, effects on the inhibition of cellular growth of TAK1-DN can be investigated using the mink epithelial cell line Mv1Lu.

The mink epithelial cell line Mv1Lu (Mv/DN1 and Mv/DN4) into which pTAK1DN had been introduced and the control cells (Mv/NEO) into which pCOS1 containing no inserted genes had been introduced were incubated in a low-serum medium (Medium 199 containing 0.2% FBS) with or without various concentrations of TGF-β for 24 hours. Then BrdU (manufactured by Boehringer Mannheim) was added to a final concentration of 1 mM and was further incubated for 4 hours. Cellular growth could be evaluated by determining the amount of BrdU incorporated into the cells according to the instructions by the manufacturer.

Example 10

Construction of TAB1 Deletion Mutant Expression Vector

In order to determine the region in the TAB1 polypeptide that is required for binding to the TAK1 polypeptide by the yeast 2-hybrid method, expression vectors for TAB1 deletion mutants were constructed. Thus, it was designed that the TAB1 partial polypeptide can be expressed as a fusion polypeptide with the GAL4 transcription activated domain polypeptide in yeast cells by constructing a gene fragment encoding a partial polypeptide of the TAB1 polypeptide, which is then inserted into a yeast 2-hybrid expression vector pGAD10 (manufactured by CLONTECH), and was so constructed.

Example 10-1

Construction of Deletion Mutants from the Amino Terminal

TAB1C45, TAB1C25, TAB1C24, TAB1C23, TAB1C22, TAB1C21 and TAB1C20 are polypeptides that comprise 45, 25, 24, 23, 22, 21 and 20 amino acids, respectively, of the carboxy terminal of TAB1 (FIG. 11). An expression vector that expresses each of TAB1C45, TAB1C25, TAB1C24, TAB1C23, TAB1C22, TAB1C21 and TAB1C20 as a fusion polypeptide with the GAL4 transcription activated domain polypeptide was constructed as follows:

The gene fragment that encodes TAB1C45 was amplified by the PCR method using pGAD-TAB1 (Shibuya H. et al., Science (1996) 272, 1179–1182) as a template. pGAD-TAB1 is a yeast 2-hybrid expression vector that expresses a fusion polypeptide of the 68 amino acids of the carboxy terminal of TAB1 and the GAL4 transcription activated domain polypeptide. Primers used are a sense primer TABC45 (SEQ ID NO: 24) that contains a restriction enzyme XhoI recognition sequence and an antisense primer TABCapEc (SEQ ID NO: 25) that contains a restriction enzyme EcoRI recognition sequence and 2 stop codons. The PCR method comprised a total of 15 cycles of 94° C. for 1 minute, 55° C. for 1 minute, and 72° C. for 1 minute per cycle.

PCR reaction products were separated and purified by a 1% low-melting point agarose gel (manufactured by Sigma), digested with restriction enzymes XhoI and EcoRI, and then were inserted into a yeast 2-hybrid expression vector pGAD-TAB1 (manufactured by CLONTECH) to obtain a plasmid pGAD-TAB1C45 that expresses a fusion polypeptide of TAB1C45 and the GAL4 transcription activated domain.

A gene fragment that encodes TAB1C25 was amplified using a sense primer C25X (SEQ ID NO: 26) containing a restriction enzyme XhoI recognition sequence and an antisense primer TABCapEc (SEQ ID NO: 25) by the PCR method with plasmid pGAD-TAB1C45 as a template, and plasmid pGAD-TAB1C25 that expresses a fusion polypeptide of TAB1C25 and the GAL4 transcription activated domain was obtained.

A gene fragment that encodes TAB1C24 was amplified using a sense primer C24X (SEQ ID NO: 27) containing a restriction enzyme XhoI recognition sequence and an antisense primer TABCapEc (SEQ ID NO: 25) by the PCR method with plasmid pGAD-TAB1C45 as a template, and plasmid pGAD-TAB1C24 that expresses a fusion polypeptide of TAB1C24 and the GAL4 transcription activated domain was obtained.

A gene fragment that encodes TAB1C23 was amplified using a sense primer C23X (SEQ ID NO: 28) containing a restriction enzyme XhoI recognition sequence and an antisense primer TABCapEc (SEQ ID NO: 25) by the PCR method with plasmid pGAD-TAB1C45 as a template, and plasmid pGAD-TAB1C23 that expresses a fusion polypeptide of TAB1C23 and the GAL4 transcription activated domain was obtained.

A gene fragment that encodes TAB1C22 was amplified using a sense primer C22X (SEQ ID NO: 29) containing a restriction enzyme XhoI recognition sequence and an antisense primer TABCapEc (SEQ ID NO: 25) by the PCR method with plasmid pGAD-TAB1C45 as a template, and plasmid pGAD-TAB1C22 that expresses a fusion polypeptide of TAB1C22 and the GAL4 transcription activated domain was obtained.

A gene fragment that encodes TAB1C21 was amplified using a sense primer C21X (SEQ ID NO: 30) containing a restriction enzyme XhoI recognition sequence and an antisense primer TABCapEc (SEQ ID NO: 25) by the PCR method with plasmid pGAD-TAB1C45 as a template, and plasmid pGAD-TAB1C21 that expresses a fusion polypeptide of TAB1C21 and the GAL4 transcription activated domain was obtained.

A gene fragment that encodes TAB1C20 was amplified using a sense primer C20X (SEQ ID NO: 31) containing a restriction enzyme XhoI recognition sequence and an antisense primer TABCapEc (SEQ ID NO: 25) by the PCR method with plasmid pGAD-TAB1C45 as a template, and plasmid pGAD-TAB1C20 that expresses a fusion polypeptide of TAB1C20 and the GAL4 transcription activated domain was obtained.

Example 10-2

Deletion from the Carboxy Terminal

Polypeptides that further lack polypeptides sequentially from the carboxy terminal of the polypeptide comprising 45 amino acids of the carboxy terminal portion of TAB1, i. e. TAB1C45 Δ14, TAB1C45 Δ19, TAB1C45 Δ20, TAB1C45 Δ21, TAB1C45 Δ22, TAB1C45 Δ23, TAB1C45 Δ24 and TAB1C45 Δ25 (FIG. 12), were designed as follows:

Thus, TAB1C45 Δ14 is a polypeptide that lacks 14 amino acids from the carboxy terminal of the polypeptide comprising 45 amino acids of the carboxy terminal portion of TAB1. Similarly, TAB1C45 Δ19, TAB1C45 Δ20, TAB1C45

Δ21, TAB1C45 Δ22, TAB1C45 Δ23, TAB1C45 Δ24 and TAB1C45 Δ25 are polypeptides that lack 19, 20, 21, 22, 23, 24 and 25 amino acids, respectively, from the carboxy terminal of the polypeptide comprising 45 amino acids of the carboxy terminal portion of TAB1.

Plasmids that express these polypeptides as fusion polypeptides with the GAL4 transcription activated domain were constructed as follows:

The gene fragment that encodes TAB1C45 Δ14 polypeptide was amplified by the PCR method using PGAD-TAB1C45 as a template. Thus, PCR was carried out using a sense primer TABC45 (SEQ ID NO: 24) that contains a restriction enzyme XhoI recognition sequence and an antisense primer TABCD14A (SEQ ID NO: 32) that contains a restriction enzyme EcoRI recognition sequence and 2 stop codons. The PCR method comprised a total of 15 cycles of 94° C. for 1 minute, 55° C. for 1 minute, and 72° C. for 1 minute per cycle.

PCR reaction products were separated and purified by a 1% low-melting point agarose gel (manufactured by Sigma), digested with restriction enzymes XhoI and EcoRI, and then were inserted into a yeast 2-hybrid expression vector pGAD10 (manufactured by CLONTECH) to obtain a plasmid pGAD-TAB1C45D14 that expresses a fusion polypeptide of TAB1C45 Δ14 polypeptide and the GAL4 transcription activated domain.

A gene fragment that encodes TAB1C45 Δ19 was amplified using a sense primer TABC45 (SEQ ID NO: 24) and an antisense primer TABCD19A (SEQ ID NO: 33) containing a restriction enzyme EcoRI recognition sequence and 2 stop codons by the PCR method with plasmid pGAD-TAB1C45 as a template, and thereby plasmid pGAD-TAB1C45D19 that expresses a fusion polypeptide of TAB1C45 Δ19 and the GAL4 transcription activated domain was obtained.

A gene fragment that encodes TAB1C45 Δ20 was amplified using a sense primer TABC45 (SEQ ID NO: 24) and an antisense primer TABCD20 (SEQ ID NO: 34) containing a restriction enzyme EcoRI recognition sequence and 2 stop codons by the PCR method with plasmid pGAD-TAB1C45 as a template, and thereby plasmid pGAD-TAB1C45D20 that expresses a fusion polypeptide of TAB1C45 Δ20 and the GAL4 transcription activated domain was obtained.

A gene fragment that encodes TAB1C45 Δ21 was amplified using a sense primer TABC45 (SEQ ID NO: 24) and an antisense primer TABCD21 (SEQ ID NO: 35) containing a restriction enzyme EcoRI recognition sequence and 2 stop codons by the PCR method with plasmid pGAD-TAB1C45 as a template, and thereby plasmid pGAD-TAB1C45D21 that expresses a fusion polypeptide of TAB1C45 Δ21 and the GAL4 transcription activated domain was obtained.

A gene fragment that encodes TAB1C45 Δ22 was amplified using a sense primer TABC45 (SEQ ID NO: 24) and an antisense primer TABCD22 (SEQ ID NO: 36) containing a restriction enzyme EcoRI recognition sequence and 2 stop codons by the PCR method with plasmid pGAD-TAB1C45 as a template, and thereby plasmid pGAD-TAB1C45D22 that expresses a fusion polypeptide of TAB1C45 Δ22 and the GAL4 transcription activated domain was obtained.

A gene fragment that encodes TAB1C45 Δ23 was amplified using a sense primer TABC45 (SEQ ID NO: 24) and an antisense primer TABCD23 (SEQ ID NO: 37) containing a restriction enzyme EcoRI recognition sequence and 2 stop codons by the PCR method with plasmid pGAD-TAB1C45 as a template, and thereby plasmid pGAD-TAB1C45D23 that expresses a fusion polypeptide of TAB1C45 Δ23 and the GAL4 transcription activated domain was obtained.

A gene fragment that encodes TAB1C45 Δ24 was amplified using a sense primer TABC45 (SEQ ID NO: 24) and an antisense primer TABCD24 (SEQ ID NO: 38) containing a restriction enzyme EcoRI recognition sequence and 2 stop codons by the PCR method with plasmid pGAD-TAB1C45 as a template, and thereby plasmid pGAD-TAB1C45D24 that expresses a fusion polypeptide of TAB1C45 Δ24 and the GAL4 transcription activated domain was obtained.

A gene fragment that encodes TAB1C45 Δ25 was amplified using a sense primer TABC45 (SEQ ID NO: 24) and an antisense primer TABCD25 (SEQ ID NO: 39) containing a restriction enzyme EcoRI recognition sequence and 2 stop codons by the PCR method with plasmid pGAD-TAB1C45 as a template, and thereby plasmid pGAD-TAB1C45D25 that expresses a fusion polypeptide of TAB1C45 Δ25 and the GAL4 transcription activated domain was obtained.

Example 11

Transformation of Yeast

In order to evaluate each TAB1 deletion mutant constructed in Example 10, a yeast 2-hybrid expression vector of each TAB1 deletion mutant and a yeast 2-hybrid expression vector pBTMHu11F (shibuya H. et al., Science (1996) 272, 1179–1182) that expresses TAK1 were co-transformed into a yeast strain L40 (Shibuya H. et al., Science (1996) 272, 1179–1182). One mg each of a TAB1 deletion mutant expression vector (pGAD-TAB1C45 to pGAD-TAB1C45 in Working Example 10-1 and pGAD-TAB1C45D14 to pGAD-TAB1C45D25 in Working Example 10-2) or pGAD-TAB1 (Shibuya H. et al., Science (1996) 272, 1179–1182) as a control and pBTMHu11F were introduced into the L40 strain according to the instructions (MATCHMAKER™ Two-Hybrid System, manufactured by CLONTECH), and were incubated on a selection agar medium SD-ULW (glucose 20 g, agar (manufactured by DIFCO) 20 g, Yeast Nitrogen Base w/o amino acids (manufactured by DIFCO) 6.7 g, adenine 100 mg, isoleucine 30 mg, valine 150 mg, arginine 20 mg, lysine 30 mg, methionine 20 mg, phenylalanine 50 mg, threonine 200 mg, tyrosine 30 mg, histidine 100 mg per liter of medium) at 30° C. for 3 days to obtain each transformant.

Example 12

Evaluation of the Binding Ability of TAB1 Deletion Mutants to TAK1

In order to evaluate the binding ability to TAK1 of each TAB1 deletion mutant constructed in Example 10, activity was determined by the yeast 2-hybrid method. Since a reporter gene lacz having the LexA binding sequence upstream thereof has been integrated on the chromosome of the yeast strain L40, the binding ability to TAK1 of each TAB1 deletion mutant can be evaluated in relative terms by measuring the activity of β-galactosidase that is a reporter gene product.

Example 12-1

Evaluation of Deletion Mutants (TAB1C45 to TAB1C20) from the Amino Terminal

The β-galactosidase activity of each transformant obtained in Example 11 was determined according to the instructions (MATCHMAKER™ Two-Hybrid System, manufactured by CLONTECH), and the activity was calculated using Miller Unit (Miller, J. H. (1972) Experiments in Molecular Genetics, Cold Spring Harbor Laboratory, Cold Spring Harbor, N.Y.).

The results are shown in FIG. 11. In FIG. 11, the β-galactosidase activity of each TAB1 deletion mutant and the yeast L40 transformed by the yeast 2-hybrid expression plasmid of TAK1 was expressed in terms of Miller Units. Measurement was carried out three times and the mean+/−SD is shown. The value indicates a ratio based on the β-galactosidase activity of the yeast L40 transformed by TAB1C68 and the yeast 2-hybrid expression plasmid of TAK1.

Since specific activities of TAB1C25 and TAB1C24 are 0.28 and 0.35, respectively, whereas those of TAB1C23, TAB1C22, TAB1C21 and TAB1C20 markedly decrease to 0.05, 0.03, 0.03 and 0.03, respectively, the amino terminal of the region required for binding of TAB1 to TAK1 is believed to be the amino terminal Tyr residue (amino acid position 481 in the amino acid sequence as set forth in SEQ ID NO: 2) of TAB1C24.

Example 12-2

Evaluation of Deletion Mutants (TAB1C45 Δ14 to TAB1C45 Δ25) from the Carboxy Terminal The β-galactosidase activity of each transformant obtained in Example 11 was determined according to the instructions (MATCHMAKER™ Two-Hybrid System, manufactured by CLONTECH), and the activity was calculated using Miller Units (Miller, J. H. (1972) Experiments in Molecular Genetics, Cold Spring Harbor Laboratory, Cold Spring Harbor, N.Y.).

Figure 12:
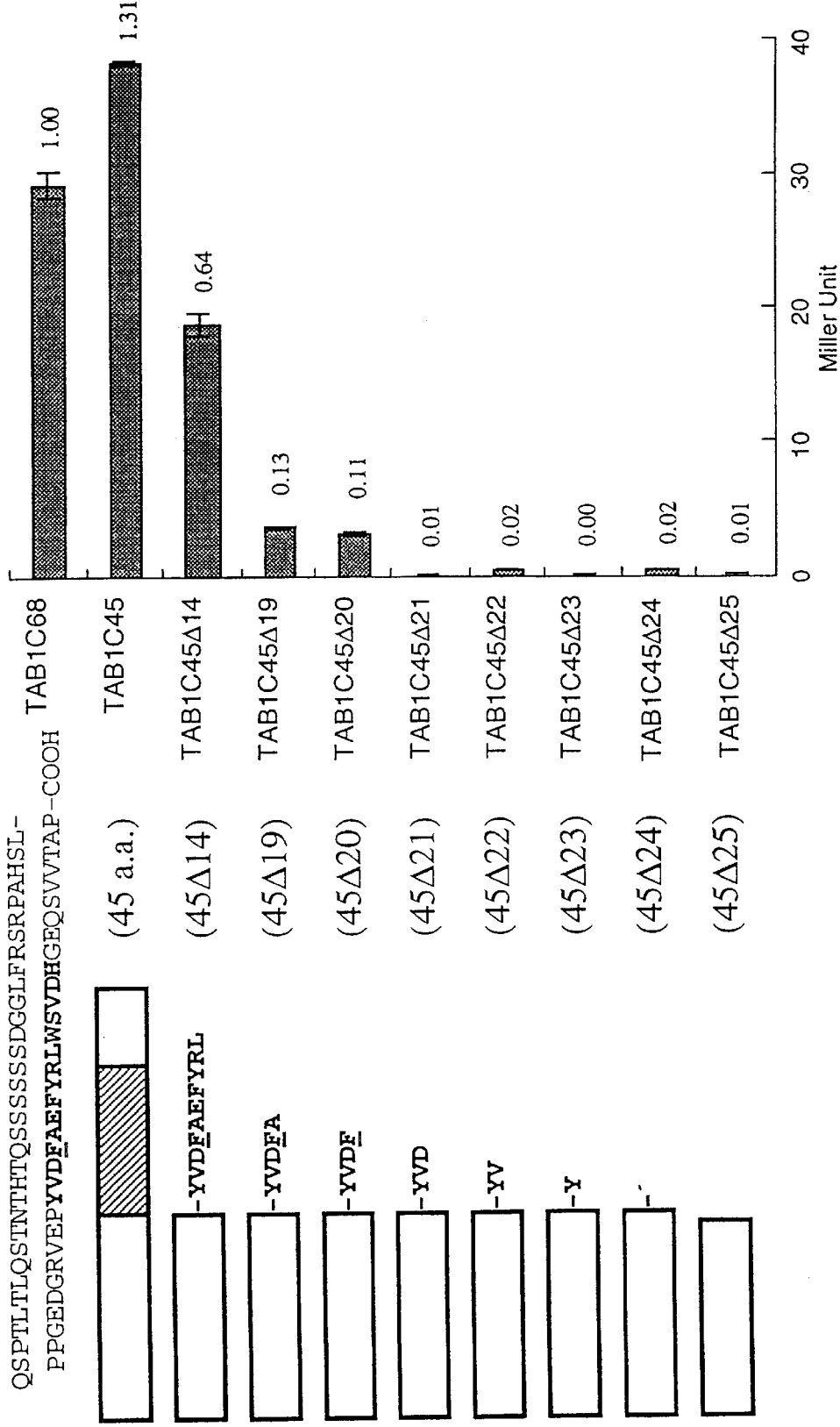
FIG. 12 (encompassed by positions 437–504 of SEQ ID NO: 2) is the activity in Miller Units of β-galactosidase of a yeast L40 that was transformed with a carboxy terminal-truncated TAB1 mutants (TAB1C45 Δ14–TAB1C45 Δ25) and a yeast 2-hybrid expression plasmid of TAK1. The measurement was conducted three times and the result is expressed in the mean+/−S.D. The values represent a ratio to the β-galactosidase activity of the yeast L40 that was transformed with TAB1C68 and the yeast 2-hybrid expression plasmid of TAK1.

The results are shown in FIG. 12. In FIG. 12, the β-galactosidase activity of the yeast L40 transformed by each TAB1 deletion mutant and the yeast 2-hybrid expression plasmid of TAK1 was expressed in terms of Miller Units. Measurement was carried out three times and the mean+/−SD is shown. The value indicates a ratio based on the β-galactosidase activity of the yeast L40 transformed by the TAB1C68 and yeast 2-hybrid expression plasmid of TAK1.

Since specific activities of TAB1C45 Δ19 and TAB1C45 Δ20 are 0.13 and 0.11, respectively, whereas those of TAB1C45 Δ21, TAB1C45 Δ22, TAB1C45 Δ23, TAB1C45 Δ24 and TAB1C45 Δ25 markedly decrease to 0.01, 0.02, 0.00, 0.02 and 0.01, respectively, the carboxy terminal of the region required for binding of TAB1 to TAK1 is believed to be the carboxy terminal Phe residue (amino acid position 484 in the amino acid sequence as set forth in SEQ ID NO: 2) of TAB1C45 Δ20.

From the foregoing, the region required for binding of TAB1 to TAK1 is believed to be the region from Tyr at amino acid position 481 to Phe at amino acid position 484 of the amino acid sequence as set forth in SEQ ID NO: 2.

Example 13

Binding-inhibition Study Using Synthetic Peptides

The fact that a synthetic peptide containing the amino acid sequence identified as the TAK1 binding region can inhibit binding between TAK1 and TAB1 was confirmed by the following experiment. Thus, a peptide TAB1C-1 (SEQ ID NO: 40) comprising 16 amino acid residues containing the TAK1 binding region of TAB1 described in the above Example and a control peptide TAB1C-2 (SEQ ID NO: 41) containing an amino acid sequence from Gln at position 437 to Gln at position 451 of TAB1 were each synthesized, and were evaluated for their effects on the binding between TAK1 and TAB1. The TAK1 and TAB1 used in the present invention were prepared in the following manner. Thus, the TAK1 expression vector or the TAB1 expression vector, was introduced into COS-7 cells using LIPOFECTOAMINE (manufactured by GIBCO-BRL) by a standard method. After incubating for 72 hours, the cells were harvested and washed with PBS. Subsequently, they were suspended in the lysis buffer (10 mM Tris-HCl, pH 7.4, 150 mM NaCl, 1 mM EDTA, 1% NP-40, Complete Protease Inhibitor Cocktail (Boehringer Mannheim)), incubated at 4° C. for 1 hour, and the insoluble components were removed by centrifugation to prepare each cell extract.

The TAK1 expression vector pCOS-TAK1 was constructed as described below. Thus, plasmid pBacTABF having a nucleotide sequence encoding TAK1-6×His was digested with restriction enzymes EcoRI and NotI, and a gene fragment containing a nucleotide sequence encoding TAK1-6×His was purified using a 1.5% low-melting point agarose gel (manufactured by Sigma) and was inserted to an expression vector pCOS1 to construct pCOS-TAK1. The TAB1 expression vector pCOS-FTAKB1 was constructed as described below. Thus, a gene fragment encoding RLAG-TAB1 (SEQ ID NO: 42) to which was added a FLAG tag comprising 8 amino acids to the amino terminal of TAB1 was amplified by the PCR method using pBacTABF as a template DNA. The PCR method was carried out as described above using Eco-MetFTAB (SEQ ID NO: 44) as a sense primer that was designed to contain a nucleotide sequence encoding a restriction enzyme EcoRI recognition site, ATG initiation codon, and a FLAG tag and TABC-Not (SEQ ID NO: 45) as an antisense primer that was designed to contain a stop codon and a restriction enzyme NotI recognition site. The PCR product was digested with restriction enzymes EcoRI and NotI, inserted into pCOS1, and the plasmid that has the correct base sequence was used as the expression vector pCOS-FTAB1.

Subsequently, cell extracts each containing TAK1-6×His or FLAG-TAB1 and a 5 mM synthetic peptide were mixed to a final concentration of 50 or 500 mM, respectively, and then incubated overnight at 4° C. It was then immunoprecipitated using anti-TAK1 antibody, and the amount of bound TAK1 and TAB1 was evaluated by determining the amount of TAB1 that coprecipitated by Western analysis. Thus, 2 mg each of anti-TAK1 polyclonal antibody (manufactured by SantaCruz) was added to each reaction mixture, and further incubated at 4° C. for 1 hour. Then 40 μl (50% v/v) of Protein-G Sepharose (manufactured by Pharmacia) was added thereto, and was further incubated for 1 hour. After the immunoprecipitate was washed three times with TBS containing 0.05% Tween 20, it was subjected to SDS-PAGE. The immunoprecipitate separated by SDS-PAGE was transferred to a nitrocellulose membrane (manufactured by Schleicher & Schuell) and was subjected to a Western analysis. After it was blocked using a TBS solution containing 5% BSA, TAK1 in the immunoprecipitate was detected using anti-TAK1 antibody (manufactured by SantaCruz) and the coprecipitataed FLAG-TAB1 was detected using anti-FLAG M2 antibody (manufactured by Kodak). The amount of TAK1 and FLAG-TAB1 was each determined by quantifying each band using an analysis software Quantity One (manufactured by PDI), and the amount of the coprecipitated FLAG-TAB1 was corrected with the amount of TAK1 to obtain the amount bound of TAK1 and TAB1.

Figure 13:
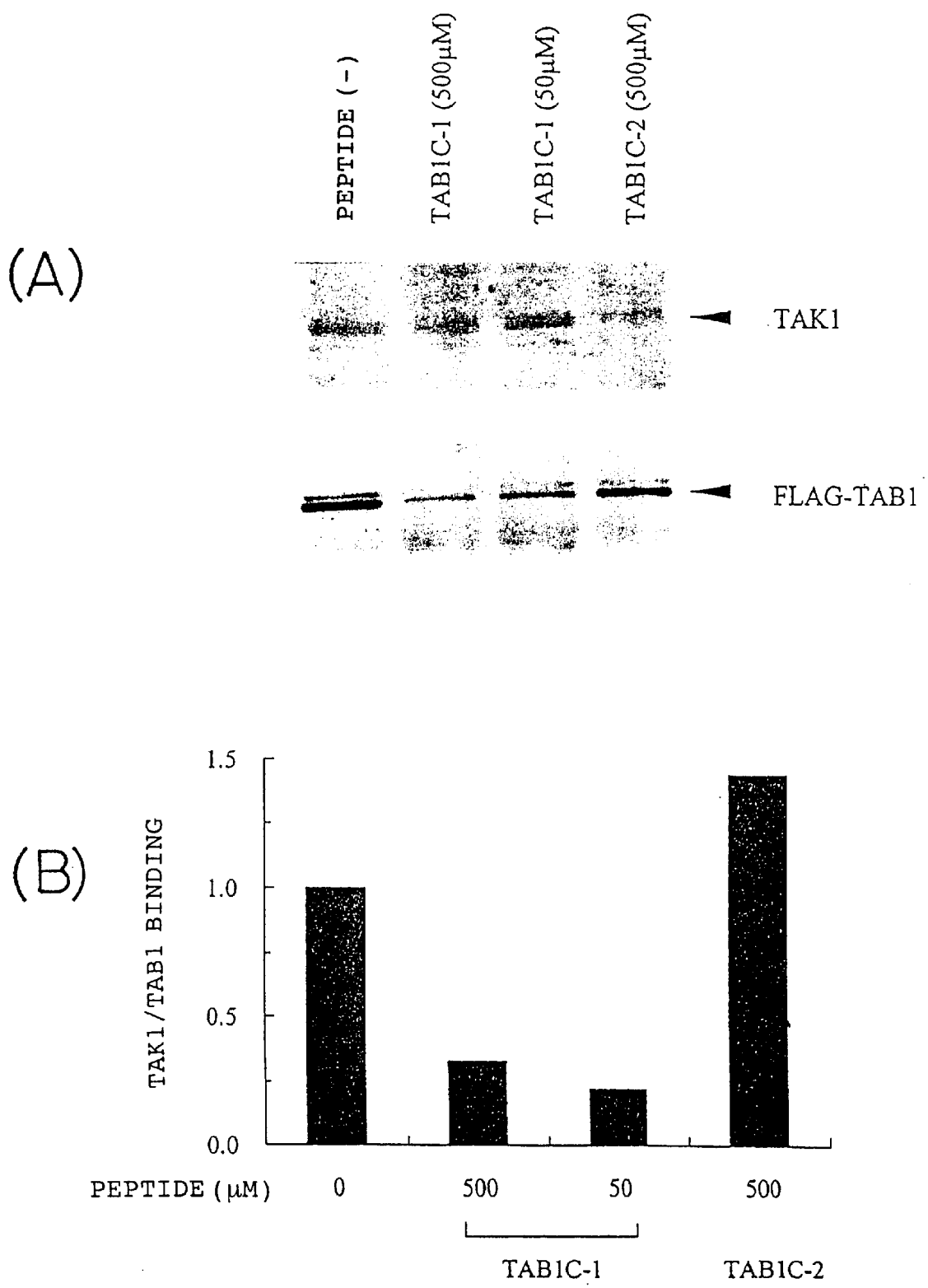
FIG. 13A is the result of Western analysis of TAK1 and FLAG-TAB1 contained in the immunoprecipitate obtained using anti-TAK1 antibody in the presence or absence of each peptide.
FIG. 13B is the result obtained by quantifying the density of bands each obtained by Western analysis and then by correcting the amount of the co-precipitated FLAG-TAB1 with the amount of TAK1. The values represent values relative to that obtained in the absence of the peptide which was set as 1.

The result is shown in FIG. 13. Compared to the case wherein no synthetic peptides were added, no decrease in binding between TAK1 and TAB1 was observed when the control peptide TAB1C-2 was added, whereas a decrease in the amount of coprecipitated FLAG-TAB1 was observed when TAB1C-1 was added. The above result indicates that a synthetic peptide containing the TAK1 binding region has an activity of inhibiting binding between TAK1 and TAB1. Accordingly, it is believed that synthetic peptides containing the amino acid sequence identified as the TAK1 binding region or derivatives thereof and substances that act on that region act on binding between TAK1 and TAB1 and activate or inhibit signal transduction from TAK1.

Example 14

Identification of the TAB1 Region Essential for the Induction of TAK1 Activation The region of TAB1 required to induce the kinase activity after binding to TAK1 was identified using TAB1 deletion mutants.

Expression vectors for the 40, 35 and 30 amino acid regions (FIG. 14) in the carboxy terminal of TAB1 were constructed as described below. Thus, genes encoding 40, 35 and 30 amino acid regions respectively in the carboxy terminal of TAB1 were amplified by the PCR method as described above, digested with restriction enzymes XhoI and EcoRI, and inserted to the GAL4 transcription activated domain expression vector pGAD10 to construct pGAD-TAB1C40, pGAD-TAB1C35 and pGAD-TAB1C30, respectively. Furthermore, expression vectors for the TAB1 deletion mutants (FIG. 14) comprising 68, 45 and 25 amino acid regions in the carboxy terminal of TAB1 used were pGAD-TAB1, pGAD-TAB1C45 and pGAD-TAB1C25.

The gene encoding the 40 amino acid region of the carboxy terminal of TAB1 was amplified using a sense primer TABC40 (SEQ ID NO: 46) containing a restriction enzyme XhoI recognition sequence and an antisense primer TABCapEc (SEQ ID NO: 25) by the PCR method with plasmid pGAD-TAB1C45 as a template DNA.

The gene encoding the 35 amino acid region of the carboxy terminal of TAB1 was amplified using a sense primer TABC35 (SEQ ID NO: 47) containing a restriction enzyme XhoI recognition sequence and an antisense primer TABCapEc (SEQ ID NO: 25) by the PCR method with plasmid pGAD-TAB1C45 as a template DNA.

The gene encoding the 30 amino acid region of the carboxy terminal of TAB1 was amplified using a sense primer TABC30 (SEQ ID NO: 48) containing a restriction enzyme XhoI recognition sequence and an antisense primer TABCapEc (SEQ ID NO: 25) by the PCR method with plasmid pGAD-TAB1C45 as a template DNA.

First, binding between the 68, 45, 40, 35, 30 and 25 amino acid regions of the carboxy terminal of TAB1 and TAK1 was evaluated by the yeast 2-hybrid method mentioned above.

Subsequently, it was investigated whether each TAB1 deletion mutant can induce the kinase activity of TAK1 using the method described in Japanese Unexamined Patent Publication (Kokai) 9(1997)-163990. Thus, the above TAB1 deletion mutant expression vector and TAK1 expression vector pNV11-HU11 (Yamaguchi, K. et al., Science (1995) 270, 2008–2011) were introduced into *Saccharomyces cereviceae* SY1984-P strain (his3Δ, stellΔ, FUS1p::HIS3, STE7$^{P368}$) to obtain deletion mutants. In this yeast strain, the original his3 is lacking, and hence it can only grow when foreign histidine is present in the medium or when the lacking Stell activity is complemented by mutation. These transformants were plated onto a SC-His (glucose 20 g, agar (manufactured by DIFCO) 20 g, Yeast Nitrogen Base w/o amino acids (manufactured by DIFCO) 6.7 g, adenine 100 mg, isoleucine 30 mg, valine 150 mg, arginine 20 mg, lysine 30 mg, methionine 20 mg, phenylalanine 50 mg, threonine 200 mg, tyrosine 30 mg per liter of medium) plate containing no histidine, incubated at 30° C., and the growth of yeast transformed with each expression vector was confirmed in order to evaluate the ability of each TAB1 deletion mutant to activate TAK1.

These results are shown in FIG. 14. Binding to TAK1 was observed for all TAB1 deletion mutants whereas the ability to activate TAK1 for each TAB1 mutant was observed for TAB1C68, 45, 40, 35 and 30 but not for TAB1C25. From these results, it is believed that the region important for TAK1 activation is present in between No. 30 and No. 26 (corresponding to Asp at position 475 to Glu at position 479 in the amino acid sequence of SEQ ID NO: 2) from the carboxy terminal. Thus, peptides that lack an amino acid sequence of this region, or peptides that contain this amino acid sequence or derivatives thereof as well as substances that act on this region can serve as an inhibitor or inducer or a stimulator of TAK1 activation.

Reference Example 1

It was analyzed whether a polypeptide (TAK1-DN) comprising Glu at position 77 to Gln at position 303 of the TAK1 polypeptide as set forth in SEQ ID NO: 4 inhibits binding between the TAK1 polypeptide and the TAB1 polypeptide and whether it can inhibit the activation of the TAK1 polypeptide in animal cells by an animal cell 2-hybrid system (Dang et al., (1991) Mol. Cell. Biol. 11, 954–962) using the TAB1 polypeptide and the TAK1 polypeptide.

First, a gene encoding a full-length TAK1 and TAK1-DN and a gene encoding the GAL4 DNA-binding domain (GAL4-BD) were ligated to construct an expression vector. A gene encoding a full-length TAK1 was prepared by digesting yeast 2-hybrid expression plasmid pBTMHu11F (Shibuya H. et al., (1996) 272, 1179–1182) with restriction enzymes EcoRI and PstI, and was then linked to the EcoRI/Pst site of an expression vector pM (manufactured by CLONTECH) containing the GAL4-BD gene, which was termed an animal cell 2-hybrid expression plasmid pM-TAK1.

Subsequently, a gene encoding TAK1-DN was amplified using a sense primer DNTAK5' (SEQ ID NO: 22) to which a restriction enzyme EcoRI recognition site had been added and an antisense primer DNTAK3' (SEQ ID NO: 23) to which a restriction enzyme PstI recognition site had been added by PCR with plasmid pBTMHu11F as a template DNA. After digestion with restriction enzymes EcoRI and PstI, it was ligated to the pM vector to obtain an animal cell 2-hybrid expression plasmid pM-TAK1DN.

Then, a gene encoding TAB1C68 comprising 68 amino acid residues of the carboxy terminal of the TAB1 polypeptide and a gene encoding VP16 protein-derived transcription activated domain (VP16-AD) of herpes simplex virus were ligated to construct an expression vector. A gene encoding TAB1C68 was prepared by digesting yeast 2-hybrid expression plasmid pGAD-TAB1 (Shibuya H. et al., (1996) 272, 1179–1182) with a restriction enzyme EcoRI, and was then linked to the EcoRI site of an expression vector pVP16 (manufactured by CLONTECH) containing a gene encoding VP16-AD, which was termed an animal cell 2-hybrid expression plasmid pVP16-C68.

The reporter plasmid used was pG-Luc in which a gene encoding CAT of pG5CAT (manufactured by CLONTECH)

having five contiguous GAL4 binding sites and the chloramphenicol asetyltransferase (CAT) gene downstream thereof replaced with the luciferase gene.

After incubating overnight CHO cells ($5 \times 10^4$ cells/well), they were washed with PBS. Then a mixture comprising 500 ng of a GAL4-BD fusion protein expression plasmid (either of pM, pM-TAK1, and pM-TAK1DN), 500 ng of a VP16-AD fusion protein expression plasmid (either of pVp16 and pVp16-C68), 100 ng of the reporter plasmid pG5-Luc and 50 ng of pRL-SV40 (containing the luciferase gene of Renilla downstream of SV40 promoter: manufactured by Promega) and 10 ml of LIPOFECTOAMINE (manufactured by GIBCO-BRL) was added thereto and was incubated for 5 hours to introduce genes.

Figure 9:
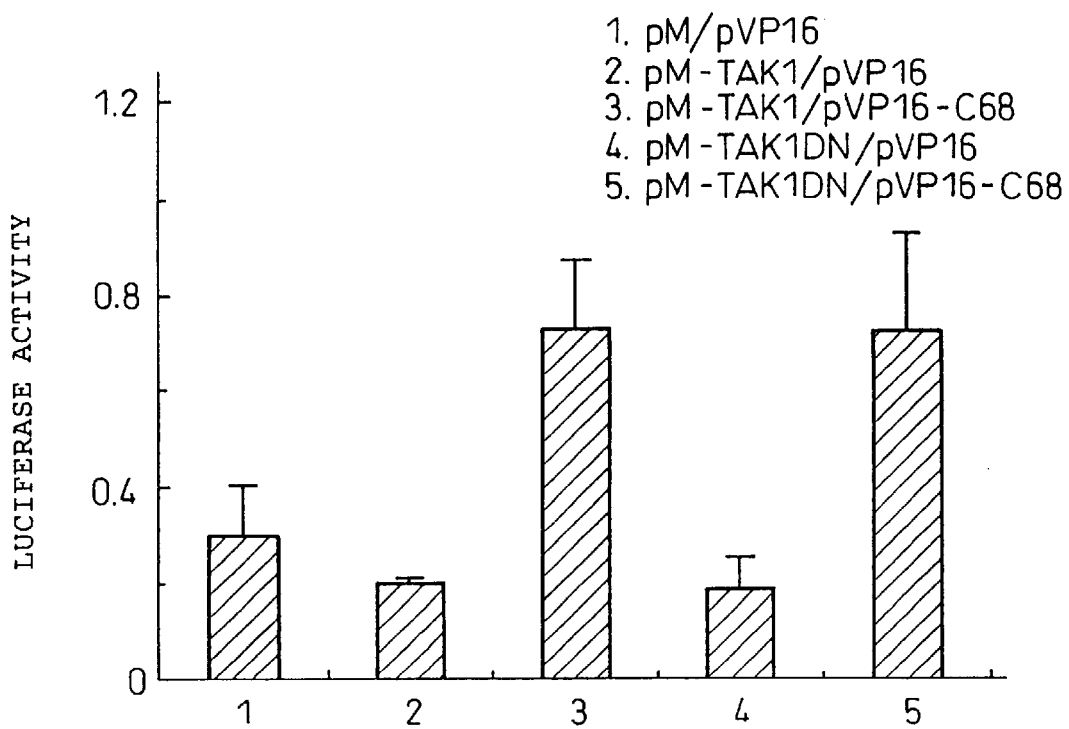
FIG. 9 is a graph showing the result of a two-hybrid assay using the CHO cells. The values represent the mean+/−S.D. of the luciferase activity in the culture supernatant prepared from three different wells.

After further incubating for 72 hours, luciferase activity in each cell extract was determined using the Dual-Luciferase™ Assay System (manufactured by Promega). Thus, after the cells were washed with PBS, 250 ml of the Passive Lysis Buffer was added thereto, incubated at room temperature for 15 minutes, and 20 µl of each was used as the cell extract for the assay. The efficiency of gene introduction was corrected with the measured value of luciferase activity of Renilla by pRL-SV40. The result is shown in FIG. 9.

Similarly to the combination of pM-TAK1 and pVP16-C68, increases in luciferase activity was confirmed for the combination of pM-TAK1DN and pVP16-C68, revealing that TAK1DN, as the full-length TAK1, binds to TAB1.

Reference Example 2

Since TAK1DN does not contain lysine at position 63 of SEQ ID NO: 2 that is an amino acid residue essential for ATP binding for the TAK1 polypeptide to exhibit kinase activity, it is expected to exhibit no kinase activity by itself. It is also expected to inhibit the activation of endogenous TAK1 polypeptide through inhibition of binding between the full-length TAK1 polypeptide and the TAB1 polypeptide by binding to the TAB1 polypeptide in the cell.

It has been demonstrated that PAI-1 (plasminogen activator inhibitor type 1) expression is increased due to stimulation by TGF-β in the Mv1Lu cell and that PAI-1 expression is inhibited by forced expression of a catalytically inactive TAK1 polypeptide mutant TAK1-K63W (Yamaguchi K. et al., (1995) Science 270, 2008–2011).

Accordingly, TAK1DN was subjected to forced expression in the Mv1Lu cell to investigate the effects of TGF-β stimulation on PAI-1 expression. The TAK1DN expression vector used was the above-mentioned TAK1DN, and the TAK1 polypeptide mutant TAK1-K63W expression vector was constructed by inserting a gene (Yamaguchi K. et al., (1995) Science 270, 2008–2011) encoding the TAK1 polypeptide mutant TAK1-K63W in which the lysine residue at position 63 has been replaced with the tryptophan residue at the EcoRI and NotI restriction enzyme site of pCOS1 to give pTAK1K63W.

Figure 10:
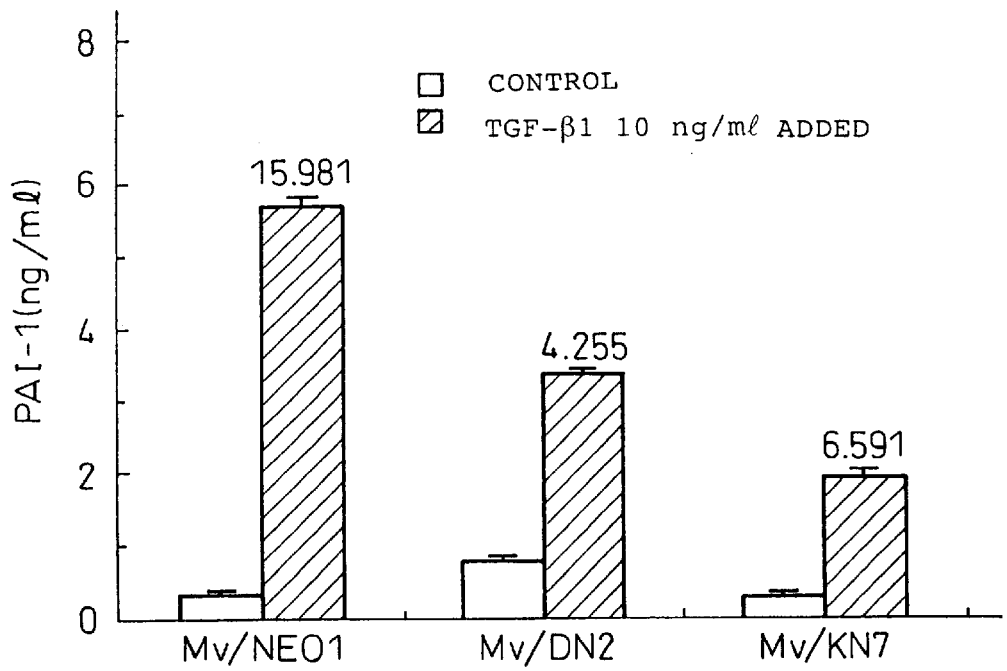
FIG. 10 is a graph showing the amount of PAI-1 in the culture supernatant when TGF-β1 was added to the Mv1Lu cells. The values represent the mean+/−S.D. of the amount of PAI-1 in the culture supernatant prepared from three different wells.

The Mv1Lu cells into which pTAK1Dn had been introduced (Mv/DN2), the cells into which pTAK1K63W had been introduced (Mv/KN7), and the control cells into which pCOS1 containing no inserted genes (Mv/NEO) had been introduced were each incubated in a low-serum medium (MEM medium containing 0.2% FBS; manufactured by GIBCO-BRL) with or without 10 ng/ml of TGF-β1 for 24 hours. The amount of PAI-1 in the culture supernatant was determined using the PAI-1 Quantative ELISA (manufactured by CALBIOCHEM). The results are shown in FIG. 10.

In the control cells there was an about 16-fold increase in PAI-1 by TGF-β1 addition in the culture supernatant, whereas in the MV/KN6 cells that express the TAK1 polypeptide mutant TAK1-K63W an increase in PAI-1 was about 6.5 fold and in the Mv/DN2 cells the increase was up to about 4.3 fold. Thus, TAK1DN inhibited the effect of enhancing expression of PAI-1 by TGF-β1 stimulation in a similar manner to the TAK1 polypeptide mutant TAK1-K63W.

The forgoing has shown that TAK1DN inhibits signal transduction via the TAK1 polypeptide and the TAB1 polypeptide by TGF-β1 stimulation, by inhibiting binding between the endogenous TAK1 polypeptide and the TAB1 polypeptide.

Industrial Applicability

It was revealed that substances that inhibit binding between the TAB1 polypeptide and the TAK1 polypeptide can be screened by the screening method of the present invention. The screening method of the present invention is useful for screening substances that inhibit binding between the TAB1 polypeptide and the TAK1 polypeptide. Substances obtained by the screening method of the present invention that inhibit binding between the TAB1 polypeptide and the TAK1 polypeptide are useful as pharmaceutical agents.

Reference to the microorganisms deposited under the Patent Cooperation Treaty, Rule 13-2, and the name of the Depository Institute Depository Institute Name: the National Institute of Bioscience and Human Technology, Agency of Industrial Science and Technology Address: 1–3, Higashi 1-chome, Tsukuba-shi, Ibaraki, Japan Organism (1)

Indication: *Escherichia coli* MC1061/P3 (pEF-TAK1DN)

Accession number: FERM BP-5245

Date deposited: Sep. 28, 1995

Organism (2)

Indication: *Escherichia coli* MC1061/P3 (pEF-TAK1)

Accession number: FERM BP-5246

Date deposited: Sep. 28, 1995

Organism (3)

Indication: *Escherichia coli* HB101 (pBS-TAB1)

Accession number: FERM BP-5508

Date deposited: Apr. 19, 1996

Organism (4)

Indication: *Escherichia coli* JM109 (phTAK1)

Accession number: FERM BP-5598

Date deposited: Jul. 19, 1996

Organism (5)

Indication: *Escherichia coli* DH5a (TAB1-f-4)

Accession number: FERM BP-5599

Date deposited: Jul. 19, 1996

What is claimed is:

1. A method for screening substances that inhibit binding between a transforming growth factor-β-activated kinase 1 (TAB1) polypeptide and TAK-1-binding (TAB1) polypeptide, wherein the TAK1 polypeptide has the amino acid sequence comprising Val at amino acid position 76 to Gln at amino acid position 303 as set forth in SEQ ID NO: 4 and the TAB 1 polypeptide has the amino acid sequence comprising Gln at amino acid position 437 to Pro at amino acid position 504 as set forth in SEQ ID NO: 2, which method comprises:

(1)(a) contacting the TAK1 polypeptide and the TAB1 polypeptide with a test sample, and detecting or determining the amount of the TAK1 polypeptide that is bound to the TAB1 polypeptide, (b) contacting the TAK1 polypeptide with the TAB1 polypeptide in the absence of a test sample, and detecting or determining the amount of the TAK1 polypeptide that is bound to the TAB1 polypeptide; and then (2) comparing the amount of bound TAK1 polypeptide obtained in the step (1)(a) to the amount of bound TAK1 polypeptide obtained in the step (1)(b).

2. The screening method according to claim 1, wherein the TAK1 polypeptide is fused to another peptide or polypeptide.

3. The screening method according to claim 1, wherein the TAB1 polypeptide is bound to a support.

4. The screening method according to claim 3, wherein the support is beads or a plate.

5. The screening method according to claim 1, wherein the TAK1 polypeptide is a labeled TAK1 polypeptide.

6. The screening method according to claim 5, wherein the labeled TAK1 polypeptide is labeled with a radioisotope, an enzyme or a fluorescent substance.

7. The screening method according to claim 1, wherein the TAK1 polypeptide bound to the TAB1 polypeptide is detected or determined by a primary antibody against the TAK1 polypeptide or a primary antibody against another peptide or polypeptide that is fused to the TAK1 polypeptide.

8. The screening method according to claim 7, wherein the TAK1 polypeptide bound to the TAB1 polypeptide is detected or determined by a primary antibody against the TAK1 polypeptide or a primary antibody against another peptide or polypeptide that is fused to the TAK1 polypeptide, and a secondary antibody against the primary antibody.

9. The screening method according to claim 7, wherein the primary antibody is labeled with a radioisotope, an enzyme or a fluorescent substance.

10. The screening method according to claim 8, wherein the secondary antibody is labeled with a radioisotope, an enzyme or a fluorescent substance.

11. A method for screening substances that inhibit binding between a TAK1 polypeptide and TAB1 polypeptide, wherein the TAK1 polypeptide has the amino acid sequence comprising Val at amino acid position 76 to Gln at amino acid position 303 as set forth in SEQ ID NO: 4 and the TAB1 polypeptide has the amino acid sequence comprising Gln at amino acid position 437 to Pro at amino acid position 504 as set forth in SEQ ID NO: 2, which method comprises:

(1)(a) contacting the TAB1 polypeptide and the TAK1 polypeptide with a test sample, and detecting or determining the amount of the TAB1 polypeptide that is bound to the TAK1 polypeptide, (b) contacting the TAB1 polypeptide to the TAK1 polypeptide in the absence of a test sample, and detecting or determining the amount of the TAB1 polypeptide that is bound to the TAK1 polypeptide; and then (2) comparing the amount of bound TAB1 polypeptide with the test sample to the amount of bound TAB1 polypeptide without the test sample.

12. The screening method according to claim 11, wherein the TAB1 polypeptide is fused to another peptide or polypeptide.

13. The screening method according to claim 11, wherein the TAK1 polypeptide is bound to a support.

14. The screening method according to claim 13, wherein the support is beads or plate.

15. The screening method according to claim 11, wherein the TAB1 polypeptide is a labeled TAB1 polypeptide.

16. The screening method according to claim 15, wherein the labeled TAB1 polypeptide is labeled with a radioisotope, an enzyme or a fluorescent substance.

17. The screening method according to claim 11, wherein the TAB1 polypeptide bound to the TAK1 polypeptide is detected or determined by a primary antibody against the TAB1 polypeptide or a primary antibody against another peptide or polypeptide that is fused to the TAB1 polypeptide.

18. The screening method according to claim 17, wherein the TAB1 polypeptide bound to the TAK1 polypeptide is detected or determined by a primary antibody against the TAB1 polypeptide or a primary antibody against another peptide or polypeptide that is fused to the TAB1 polypeptide, and a secondary antibody against the primary antibody.

19. The screening method according to claim 17, wherein the primary antibody is labeled with a radioisotope, an enzyme or a fluorescent substance.

20. The screening method according to claim 18, wherein the secondary antibody is labeled with a radioisotope, an enzyme or a fluorescent substance.

21. A method for screening substances that inhibit binding between a transforming growth factor-β-activated kinase 1 (TAK1) polypeptide and TAK-1-binding (TAB1) polypeptide, wherein the TAK1 polypeptide has the amino acid sequence comprising Met at amino acid position 1 to Gln at amino acid position 303 as set forth in SEQ ID NO: 4 and the TAB1 polypeptide has the amino acid sequence comprising Gln at amino acid position 437 to Pro at amino acid position 504 as set forth in SEQ ID NO: 2, which method comprises:
  (1)(a) contacting the TAK1 polypeptide and the TAB1 polypeptide with a test sample, and detecting or determining the amount of the TAK1 polypeptide that is bound to the TAB1 polypeptide,
  (b) contacting the TAK1 polypeptide with the TAB1 polypeptide in the absence of a test sample, and detecting or determining the amount of the TAK1 polypeptide that is bound to the TAB1 polypeptide; and then
  (2) comparing the amount of bound TAK1 polypeptide obtained in the step (1)(a) to the amount of bound TAK1 polypeptide obtained in the step (1)(b).

22. The screening method according to claim 21, wherein the TAK1 polypeptide is fused to another peptide or polypeptide.

23. The screening method according to claim 21, wherein the TAB 1 polypeptide is bound to a support.

24. The screening method according to claim 21, wherein the TAK1 polypeptide bound to the TAB1 polypeptide is detected or determined by a primary antibody against the TAK1 polypeptide or a primary antibody against another peptide or polypeptide that is fused to the TAK1 polypeptide.

25. The screening method according to claim 24, wherein the TAK1 polypeptide bound to the TAB1 polypeptide is detected or determined by a primary antibody against the TAK1 polypeptide or a primary antibody against another peptide or polypeptide that is fused to the TAK1 polypeptide, and a secondary antibody against the primary antibody.

26. A method for screening substances that inhibit binding between a transforming growth factor-β-activated kinase 1 (TAB1) polypeptide and TAK-1-binding (TAB 1) polypeptide, wherein the TAK1 polypeptide has the amino acid sequence comprising Met at amino acid position 1 to Ser at amino acid position 579 as set forth in SEQ ID NO: 4 and the TAB1 polypeptide has the amino acid sequence comprising Gln at amino acid position 437 to Pro at amino acid position 504 as set forth in SEQ ID NO: 2, which method comprises:
  (1)(a) contacting the TAK1 polypeptide and the TAB1 polypeptide with a test sample, and detecting or determining the amount of the TAK1 polypeptide that is bound to the TAB1 polypeptide,
  (b) contacting the TAK1 polypeptide with the TAB1 polypeptide in the absence of a test sample, and detecting or determining the amount of the TAK1 polypeptide that is bound to the TAB1 polypeptide; and then
  (2) comparing the amount of bound TAK1 polypeptide obtained in the step (1)(a) to the amount of bound TAK1 polypeptide obtained in the step (1)(b).

27. The screening method according to claim 26, wherein the TAK1 polypeptide is fused to another peptide or polypeptide.

28. The screening method according to claim 26, wherein the TAB1 polypeptide is bound to a support.

29. The screening method according to claim 26, wherein the TAK1 polypeptide bound to the TAB 1 polypeptide is detected or determined by a primary antibody against the TAK1 polypeptide or a primary antibody against another peptide or polypeptide that is fused to the TAK1 polypeptide.

30. The screening method according to claim 29, wherein the TAK1 polypeptide bound to the TAB1 polypeptide is detected or determined by a primary antibody against the TAK1 polypeptide or a primary antibody against another peptide or polypeptide that is fused to the TAK1 polypeptide, and a secondary antibody against the primary antibody.

31. A method for screening substances that inhibit binding between a transforming growth factor-β-activated kinase 1 (TAK1) polypeptide and TAK-1-binding (TAB1) polypeptide, wherein the TAK1 polypeptide has the amino acid sequence comprising Val at amino acid position 76 to Gln at amino acid position 303 as set forth in SEQ ID NO: 4 and the TAB1 polypeptide has the amino acid sequence comprising Met at amino acid position 1 to Pro at amino acid position 504 as set forth in SEQ ID NO: 2, which method comprises:
  (1)(a) contacting the TAK1 polypeptide and the TAB1 polypeptide with a test sample, and detecting or determining the amount of the TAK1 polypeptide that is bound to the TAB 1 polypeptide,
  (b) contacting the TAK1 polypeptide with the TAB1 polypeptide in the absence of a test sample, and detecting or determining the amount of the TAK1 polypeptide that is bound to the TAB1 polypeptide; and then
  (2) comparing the amount of bound TAK1 polypeptide obtained in the step (1)(a) to the amount of bound TAK1 polypeptide obtained in the step (1)(b).

32. The screening method according to claim 31, wherein the TAK1 polypeptide is fused to another peptide or polypeptide.

33. The screening method according to claim 31, wherein the TAB1 polypeptide is bound to a support.

34. The screening method according to claim 31, wherein the TAK1 polypeptide bound to the TAB1 polypeptide is detected or determined by a primary antibody against the TAK1 polypeptide or a primary antibody against another peptide or polypeptide that is fused to the TAK1 polypeptide.

35. The screening method according to claim 34, wherein the TAB1 polypeptide bound to the TAB1 polypeptide is detected or determined by a primary antibody against the TAK1 polypeptide or a primary antibody against another peptide or polypeptide that is fused to the TAK1 polypeptide, and a secondary antibody against the primary antibody.

36. A method for screening substances that inhibit binding between a TAK1 polypeptide and TAB1 polypeptide, wherein the TAK1 polypeptide has the amino acid sequence comprising Met at amino acid position 1 to Gln at amino acid position 303 as set forth in SEQ ID NO: 4 and the TAB1 polypeptide has the amino acid sequence comprising Gln at amino acid position 437 to Pro at amino acid position 504 as set forth in SEQ ID NO: 2, which method comprises:

(1)(a) contacting the TAB1 polypeptide and the TAK1 polypeptide with a test sample, and detecting or determining the amount of the TAB1 polypeptide that is bound to the TAK1 polypeptide, (b) contacting the TAB1 polypeptide to the TAK1 polypeptide in the absence of a test sample, and detecting or determining the amount of the TAB1 polypeptide that is bound to the TAK1 polypeptide; and then (2) comparing the amount of bound TAB 1 polypeptide with the test sample to the amount of bound TAB1 polypeptide without the test sample.

37. The screening method according to claim 36, wherein the TAB1 polypeptide is fused to another peptide or polypeptide.

38. The screening method according to claim 36, wherein the TAK1 polypeptide is bound to a support.

39. The screening method according to claim 36, wherein the TAB1 polypeptide bound to the TAK1 polypeptide is detected or determined by a primary antibody against the TAB1 polypeptide or a primary antibody against another peptide or polypeptide that is fused to the TAB1 polypeptide.

40. The screening method according to claim 39, wherein the TAB1 polypeptide bound to the TAK1 polypeptide is detected or determined by a primary antibody against the TAB 1 polypeptide or a primary antibody against another peptide or polypeptide that is fused to the TAB1 polypeptide, and a secondary antibody against the primary antibody.

41. A method for screening substances that inhibit binding between a TAK1 polypeptide and TAB1 polypeptide, wherein the TAK1 polypeptide has the amino acid sequence comprising Met at amino acid position 1 to Ser at amino acid position 579 as set forth in SEQ ID NO: 4 and the TAB1 polypeptide has the amino acid sequence comprising Gln at amino acid position 437 to Pro at amino acid position 504 as set forth in SEQ ID NO: 2, which method comprises:

(1)(a) contacting the TAB1 polypeptide and the TAK1 polypeptide with a test sample, and detecting or determining the amount of the TAB1 polypeptide that is bound to the TAK1 polypeptide, (b) contacting the TAB1 polypeptide to the TAK1 polypeptide in the absence of a test sample, and detecting or determining the amount of the TAB1 polypeptide that is bound to the TAK1 polypeptide; and then (2) comparing the amount of bound TAB 1 polypeptide with the test sample to the amount of bound TAB1 polypeptide without the test sample.

42. The screening method according to claim 41, wherein the TAB 1 polypeptide is fused to another peptide or polypeptide.

43. The screening method according to claim 41, wherein the TAK1 polypeptide is bound to a support.

44. The screening method according to claim 41, wherein the TAB1 polypeptide bound to the TAK1 polypeptide is detected or determined by a primary antibody against the TAB1 polypeptide or a primary antibody against another peptide or polypeptide that is fused to the TAB1 polypeptide.

45. The screening method according to claim 44, wherein the TAB1 polypeptide bound to the TAK1 polypeptide is detected or determined by a primary antibody against the TAB1 polypeptide or a primary antibody against another peptide or polypeptide that is fused to the TAB1 polypeptide, and a secondary antibody against the primary antibody.

46. A method for screening substances that inhibit binding between a TAK1 polypeptide and TAB1 polypeptide, wherein the TAK1 polypeptide has the amino acid sequence comprising Val at amino acid position 76 to Gln at amino acid position 303 as set forth in SEQ ID NO: 4 and the TAB1 polypeptide has the amino acid sequence comprising Met at amino acid position 1 to Pro at amino acid position 504 as set forth in SEQ ID NO: 2, which method comprises:

(1)(a) contacting the TAB1 polypeptide and the TAK1 polypeptide with a test sample, and detecting or determining the amount of the TAB1 polypeptide that is bound to the TAK1 polypeptide, (b) contacting the TAB1 polypeptide to the TAK1 polypeptide in the absence of a test sample, and detecting or determining the amount of the TAB1 polypeptide that is bound to the TAK1 polypeptide; and then (2) comparing the amount of bound TAB1 polypeptide with the test sample to the amount of bound TAB1 polypeptide without the test sample.

47. The screening method according to claim 46, wherein the TAB1 polypeptide is fused to another peptide or polypeptide.

48. The screening method according to claim 46, wherein the TAK1 polypeptide is bound to a support.

49. The screening method according to claim 46, wherein the TAB1 polypeptide bound to the TAK1 polypeptide is detected or determined by a primary antibody against the TAB1 polypeptide or a primary antibody against another peptide or polypeptide that is fused to the TAB1 polypeptide.

50. The screening method according to claim 49, wherein the TAB1 polypeptide bound to the TAK1 polypeptide is detected or determined by a primary antibody against the TAB1 polypeptide or a primary antibody against another peptide or polypeptide that is fused to the TAB1 polypeptide, and a secondary antibody against the primary antibody.

* * * * *